United States Patent
Bedian et al.

(10) Patent No.: US 12,404,335 B2
(45) Date of Patent: *Sep. 2, 2025

(54) COMPOSITIONS AND METHODS FOR TREATMENT OF THYROID EYE DISEASE

(71) Applicant: Viridian Therapeutics, Inc., Waltham, MA (US)

(72) Inventors: Vahe Bedian, Waltham, MA (US); Peter Harwin, Dorado, PR (US); Tomas Kiselak, Dorado, PR (US); Angela She, Waltham, MA (US); Jonathan Violin, Waltham, MA (US); Yang Zhao, Waltham, MA (US)

(73) Assignee: Viridian Therapeutics, Inc., Waltham, MA (US)

( * ) Notice: Subject to any disclaimer, the term of this patent is extended or adjusted under 35 U.S.C. 154(b) by 360 days.

This patent is subject to a terminal disclaimer.

(21) Appl. No.: 18/150,514

(22) Filed: Jan. 5, 2023

(65) Prior Publication Data

US 2023/0279122 A1 Sep. 7, 2023

Related U.S. Application Data

(63) Continuation of application No. 17/822,978, filed on Aug. 29, 2022, now Pat. No. 11,548,951, which is a continuation of application No. 17/501,362, filed on Oct. 14, 2021, now abandoned.

(60) Provisional application No. 63/261,742, filed on Sep. 28, 2021, provisional application No. 63/260,130, filed on Aug. 10, 2021, provisional application No. 63/201,978, filed on May 21, 2021, provisional application No. 63/091,839, filed on Oct. 14, 2020.

(51) Int. Cl.
| | |
|---|---|
| *A61P 27/02* | (2006.01) |
| A61K 9/00 | (2006.01) |
| C07K 16/28 | (2006.01) |
| *A61K 39/00* | (2006.01) |

(52) U.S. Cl.
CPC ........ *C07K 16/2863* (2013.01); *A61K 9/0019* (2013.01); *A61P 27/02* (2018.01); *A61K 2039/505* (2013.01); *A61K 2039/545* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search
CPC . C07K 16/2863; C07K 2317/94; A61P 27/02; A61K 2039/505
USPC ..................................................... 424/133.1
See application file for complete search history.

(56) References Cited

U.S. PATENT DOCUMENTS

| | | |
|---|---|---|
| 4,439,196 A | 3/1984 | Higuchi |
| 4,447,224 A | 5/1984 | DeCant, Jr. et al. |
| 4,447,233 A | 5/1984 | Mayfield |
| 4,487,603 A | 12/1984 | Harris |
| 4,596,556 A | 6/1986 | Morrow et al. |
| 4,790,824 A | 12/1988 | Morrow et al. |
| 4,816,567 A | 3/1989 | Cabilly et al. |
| 4,941,880 A | 7/1990 | Burns |
| 4,949,778 A | 8/1990 | Saito et al. |
| 5,064,413 A | 11/1991 | McKinnon et al. |
| 5,260,203 A | 11/1993 | Ladner et al. |
| 5,312,335 A | 5/1994 | Mckinnon et al. |
| 5,383,851 A | 1/1995 | Mckinnon, Jr. et al. |
| 5,399,163 A | 3/1995 | Peterson et al. |
| 5,475,096 A | 12/1995 | Gold et al. |
| 5,831,012 A | 11/1998 | Nilsson et al. |
| 6,004,746 A | 12/1999 | Brent et al. |
| 6,005,079 A | 12/1999 | Casterman et al. |
| 6,096,002 A | 8/2000 | Landau |
| 6,620,135 B1 | 9/2003 | Weston et al. |
| 6,794,144 B1 | 9/2004 | Saksela et al. |
| 6,818,418 B1 | 11/2004 | Lipovsek et al. |
| 6,994,982 B1 | 2/2006 | Watt et al. |
| 7,083,784 B2 | 8/2006 | Dall'Acqua et al. |
| 7,166,697 B1 | 1/2007 | Galanis et al. |
| 7,186,524 B2 | 3/2007 | Kolmar et al. |
| 7,250,297 B1 | 7/2007 | Beste et al. |
| 7,417,130 B2 | 8/2008 | Stumpp et al. |
| 7,572,897 B2 | 8/2009 | Graus et al. |
| 7,670,600 B2 | 3/2010 | Dall'Acqua et al. |
| 7,803,907 B2 | 9/2010 | Stemmer et al. |
| 7,838,629 B2 | 11/2010 | Fiedler et al. |
| 7,998,681 B2 | 8/2011 | Smith et al. |

(Continued)

FOREIGN PATENT DOCUMENTS

| | | |
|---|---|---|
| CN | 101229371 A | 7/2008 |
| CN | 101292036 A | 10/2008 |

(Continued)

OTHER PUBLICATIONS

Guelberto et al (Oncogene 28(34):3008-3021 (Aug. 27, 2009)).*

(Continued)

*Primary Examiner* — Lynn A Bristol

(74) *Attorney, Agent, or Firm* — Proskauer Rose LLP

(57) ABSTRACT

Antibodies and compositions against Insulin-Like Growth Factor-1 Receptor (IGF-1R) and uses thereof for treating thyroid eye disease (TED) are provided herein. Anti-IGF-1R antibodies and compositions described herein can be used in methods of treating or reducing the severity of thyroid eye disease (TED) in subjects in need thereof, by inhibiting the activity of IGF-1R with such antibodies and compositions.

9 Claims, 14 Drawing Sheets

Specification includes a Sequence Listing.

(56) References Cited

U.S. PATENT DOCUMENTS

| | | |
|---|---|---|
| 8,137,933 B2 | 3/2012 | Saha |
| 8,153,121 B2 | 4/2012 | Smith et al. |
| 8,394,925 B2 | 3/2013 | Chamberlain et al. |
| 8,951,790 B2 | 2/2015 | Saha |
| 9,045,536 B2 | 6/2015 | Merchant et al. |
| 9,982,036 B2 | 5/2018 | Bossenmaier et al. |
| 10,093,741 B1 | 10/2018 | Burak et al. |
| 10,519,245 B2 | 12/2019 | Gastwirt et al. |
| 10,611,825 B2 | 4/2020 | Bossenmaier et al. |
| 11,548,951 B1* | 1/2023 | Bedian ............... A61P 27/02 |
| 2004/0023334 A1 | 2/2004 | Prior |
| 2004/0132094 A1 | 7/2004 | Etzerodt et al. |
| 2004/0146938 A1 | 7/2004 | Nguyen et al. |
| 2004/0157209 A1 | 8/2004 | Yilmaz et al. |
| 2004/0202651 A1 | 10/2004 | Cohen et al. |
| 2004/0209243 A1 | 10/2004 | Nixon et al. |
| 2004/0265307 A1 | 12/2004 | Singh et al. |
| 2005/0084906 A1 | 4/2005 | Goetsch et al. |
| 2005/0136063 A1 | 6/2005 | Wang et al. |
| 2006/0140960 A1 | 6/2006 | Wang et al. |
| 2006/0286103 A1 | 12/2006 | Kolhe et al. |
| 2007/0041972 A1 | 2/2007 | Rother et al. |
| 2007/0071675 A1 | 3/2007 | Wu et al. |
| 2008/0014203 A1 | 1/2008 | Hansen et al. |
| 2008/0112888 A1 | 5/2008 | Wang |
| 2008/0226635 A1 | 9/2008 | Koll et al. |
| 2009/0275126 A1 | 11/2009 | Graus et al. |
| 2009/0285824 A1 | 11/2009 | Calzone et al. |
| 2010/0047239 A1 | 2/2010 | Wu et al. |
| 2010/0074900 A1 | 3/2010 | Ghayur et al. |
| 2010/0104645 A1 | 4/2010 | Ali et al. |
| 2010/0119446 A1 | 5/2010 | Grabulovski et al. |
| 2010/0143340 A1 | 6/2010 | Kolhe et al. |
| 2010/0239633 A1 | 9/2010 | Strome et al. |
| 2010/0260668 A1 | 10/2010 | Ghayur et al. |
| 2011/0014117 A1 | 1/2011 | Wang et al. |
| 2011/0014207 A1 | 1/2011 | Gualberto et al. |
| 2011/0044980 A1 | 2/2011 | Ghayur et al. |
| 2011/0229933 A1 | 9/2011 | Krishnan et al. |
| 2011/0263827 A1 | 10/2011 | Ghayur et al. |
| 2012/0014957 A1 | 1/2012 | Ghayur et al. |
| 2012/0027757 A1 | 2/2012 | Sathyanarayanan et al. |
| 2012/0065380 A1 | 3/2012 | Yoo et al. |
| 2012/0076778 A1 | 3/2012 | Koll et al. |
| 2012/0100166 A1 | 4/2012 | Roschke et al. |
| 2012/0201746 A1 | 8/2012 | Liu et al. |
| 2012/0237507 A1 | 9/2012 | Bossenmaier et al. |
| 2012/0263722 A1 | 10/2012 | Ghayur et al. |
| 2013/0004416 A1 | 1/2013 | Wu et al. |
| 2013/0195871 A1 | 8/2013 | Ghayur et al. |
| 2013/0259868 A1 | 10/2013 | Roschke et al. |
| 2013/0330323 A1 | 12/2013 | Dunn et al. |
| 2014/0050729 A1 | 2/2014 | Yao |
| 2014/0079665 A1 | 3/2014 | Goetsch et al. |
| 2015/0017168 A1 | 1/2015 | Ghayur et al. |
| 2015/0056191 A1 | 2/2015 | Sathyanarayanan et al. |
| 2015/0168424 A1 | 6/2015 | Wang |
| 2015/0274829 A1 | 10/2015 | Calzone et al. |
| 2016/0060299 A1 | 3/2016 | Luesch |
| 2016/0096894 A1 | 4/2016 | Cohen et al. |
| 2016/0151487 A1 | 6/2016 | Hartmann et al. |
| 2016/0159894 A1* | 6/2016 | Hartmann ............... C07K 16/22 |
| | | 530/387.3 |
| 2016/0289341 A1 | 10/2016 | Wu |
| 2016/0289343 A1 | 10/2016 | Wu |
| 2017/0218091 A1 | 8/2017 | Ambrosi |
| 2018/0243432 A1 | 8/2018 | Poma et al. |
| 2018/0280527 A1 | 10/2018 | Silacci Melkko et al. |
| 2018/0312573 A1 | 11/2018 | Bossenmaier et al. |
| 2019/0083662 A1 | 3/2019 | Burak et al. |
| 2019/0153071 A1 | 5/2019 | Klein et al. |
| 2019/0153471 A1 | 5/2019 | Paul et al. |
| 2019/0194713 A1 | 6/2019 | Mandell et al. |
| 2019/0225696 A1 | 7/2019 | Madden et al. |
| 2019/0270820 A1 | 9/2019 | Madden et al. |
| 2019/0293656 A1 | 9/2019 | Chaudhary |
| 2020/0023076 A1 | 1/2020 | Fotin-Mleczek et al. |
| 2020/0115460 A1 | 4/2020 | Eguchi et al. |
| 2021/0253719 A1 | 8/2021 | Sherman et al. |
| 2021/0284741 A1 | 9/2021 | Madden et al. |
| 2022/0088231 A1* | 3/2022 | Burak ............... A61K 51/1093 |
| 2022/0235137 A1 | 7/2022 | Bedian et al. |
| 2022/0267450 A1 | 8/2022 | Bedian et al. |
| 2022/0267451 A1 | 8/2022 | Bedian et al. |
| 2022/0275096 A1 | 9/2022 | Bedian et al. |
| 2023/0002495 A1 | 1/2023 | Bedian et al. |
| 2023/0084477 A1 | 3/2023 | O'Shaughnessy et al. |
| 2023/0279122 A1 | 9/2023 | Bedian et al. |
| 2024/0043546 A1* | 2/2024 | Bedian ............... A61K 9/0019 |
| 2024/0343812 A1 | 10/2024 | O'shaughnessy et al. |
| 2024/0343814 A1 | 10/2024 | Bedian et al. |
| 2024/0352133 A1* | 10/2024 | Bedian ............... A61P 27/02 |
| 2024/0360227 A1 | 10/2024 | Bedian et al. |
| 2024/0368282 A1 | 11/2024 | Schlegel et al. |
| 2025/0059287 A1* | 2/2025 | Bedian ............... A61K 9/0019 |
| 2025/0099583 A1 | 3/2025 | Huyghe et al. |

FOREIGN PATENT DOCUMENTS

| | | |
|---|---|---|
| CN | 113402602 A | 9/2021 |
| EP | 0404097 A2 | 12/1990 |
| EP | 1399483 B1 | 4/2010 |
| EP | 1689782 B1 | 4/2010 |
| EP | 2235059 A1 | 10/2010 |
| EP | 1959014 B1 | 3/2011 |
| EP | 2230254 B1 | 5/2013 |
| EP | 2681239 B1 | 7/2015 |
| EP | 2032989 B2 | 10/2015 |
| EP | 2681240 B1 | 8/2017 |
| EP | 2194067 B1 | 12/2017 |
| EP | 2863947 B1 | 3/2018 |
| EP | 2714733 B1 | 1/2019 |
| EP | 1469879 B1 | 3/2019 |
| EP | 2970433 B1 | 9/2019 |
| EP | 2814500 B1 | 1/2020 |
| EP | 2322550 B1 | 4/2020 |
| EP | 3458101 B1 | 12/2020 |
| KR | 20210094669 | * 7/2021 |
| TW | 202228775 A | 8/2022 |
| WO | 1988001649 A1 | 3/1988 |
| WO | 1993011161 A1 | 6/1993 |
| WO | 1994004678 | 3/1994 |
| WO | 1994004678 A1 | 3/1994 |
| WO | 1994025591 | 11/1994 |
| WO | 1994025591 A1 | 11/1994 |
| WO | 03100008 A2 | 12/2003 |
| WO | 03106621 A2 | 12/2003 |
| WO | 2006060419 A2 | 6/2006 |
| WO | 2007062037 A2 | 5/2007 |
| WO | 2008005469 A2 | 1/2008 |
| WO | 2008076278 A2 | 6/2008 |
| WO | 2008079849 A2 | 7/2008 |
| WO | 2011028811 A2 | 3/2011 |
| WO | 2011161119 A1 | 12/2011 |
| WO | 2014177459 A2 | 11/2014 |
| WO | 2016064716 A1 | 4/2016 |
| WO | 2017011773 A2 | 1/2017 |
| WO | 2019084026 A1 | 5/2019 |
| WO | 2019084030 A1 | 5/2019 |
| WO | 2019173352 A1 | 9/2019 |
| WO | 2019183523 A1 | 9/2019 |
| WO | 2020006486 A1 | 1/2020 |
| WO | 2020132091 A2 | 6/2020 |
| WO | 2021041773 | * 3/2021 |
| WO | 2021041773 A1 | 3/2021 |
| WO | 2021243014 A1 | 12/2021 |
| WO | 2022081799 A1 | 4/2022 |
| WO | 2022081804 A1 | 4/2022 |
| WO | 2022187510 A1 | 9/2022 |
| WO | 202301917 A1 | 1/2023 |
| WO | 2023019171 A1 | 2/2023 |
| WO | 2023122714 A2 | 6/2023 |
| WO | 2023133485 A2 | 7/2023 |

(56) References Cited

FOREIGN PATENT DOCUMENTS

| | | |
|---|---|---|
| WO | 2023133486 A2 | 7/2023 |
| WO | 2023133561 A1 | 7/2023 |
| WO | 2025014774 A1 | 1/2025 |

OTHER PUBLICATIONS

Final Office Action dated Sep. 19, 2023 for U.S. Appl. No. 17/450,872, 10 pages.
International Preliminary Report on Patentability received in PCT Appl. No. PCT/US2022/074764 mailed Feb. 13, 2024.
International Search Report and Written Opinion for Appl. No. PCT/US2022/082214 mailed Jul. 3, 2023.
International Search Report and Written Opinion for Appl. No. PCT/US2023/060206 mailed Jun. 21, 2023.
International Search Report and Written Opinion for Appl. No. PCT/US2023/060207 mailed Jun. 30, 2023.
Non-Final Office Action dated Nov. 4, 2022 for U.S. Appl. No. 17/822,978, 18 pages.
Non-Final Office Action dated Nov. 7, 2022 for U.S. Appl. No. 17/501,362, 17 pages.
Notice of Allowance dated Nov. 30, 2022 for U.S. Appl. No. 17/822,978, 12 pages.
Allen et al., "A Perspective on the Current Role of Teprotumumab in Treatment of Thyroid Eye Disease". Ophthalmology. (2021) S0161-6420(21)00167-6. doi: 10.1016/j.ophtha.2021.03.006. Epub ahead of print. PMID: 33823982.
Baert, et al. "Influence of Immunogenicity on the Long-Term Efficacy of Infliximab in Crohn's Disease" New Engl. J. Med. (2003) 348:601-608.
Beniaminovitz et al. "Prevention of Rejection in Cardiac Transplantation by Blockade of the Interleukin-2 Receptor With a Monoclonal Antibody", New Engl. J. Med. (2000) vol. 342: No. 9, pp. 613-619.
Chen et al., "Teprotumumab, an IGF-1R Blocking Monoclonal Antibody Ingibits TSH and IGF-1 Action in Fibrocytes", J Clin Endocrinol Metab (2014) 99(9):E1635-E1640.
Chiou et al., "Teprotumumab for the treatment of mild compressive optic neuropathy in thyroid eye disease: A report of two cases." American Journal of Ophthalmology Case Reports (2021): 101075.
Chothia, et al., "Canonical Structures for the Hypervariable Regions of Immunoglobulis", J Mol. Biol. (1987) 196:901-917.
Chothia, et al., "Conformations of Immunoglobulin hypervariable regions", Nature (1989) 342:877-883.
ClinicalTrials.gov Identifier: NCT01868997—Teprotumumab (RV 001) Treatment in Patients With Active Thyroid Eye Disease, 9 pages.
ClinicalTrials.gov Identifier: NCT03298867—Treatment of Graves' Orbitopathy (Thyroid Eye Disease) to Reduce Proptosis With Teprotumumab Infusions in a Randomized, Placebo-Controlled, Clinical Study (Optic), 11 pages.
ClinicalTrials.gov Identifier: NCT03461211—Treatment of Graves' Orbitopathy to Reduce Proptosis With Teprotumumab Infusions in an Open-Label Clinical Extension Study (OPTIC-X), 8 pages.
ClinicalTrials.gov Identifier: NCT03498417—Anti-insulin-like Growth Factor-1 Receptor (IGF-1 R) Antibodies in Graves' Disease and Graves' Orbitopathy (IGF1 RAbsGO), 7 pages.
ClinicalTrials.gov Identifier: NCT04040894—Expanded Access Protocol of Teprotumumab (HZN-001) for Patients With Active Thyroid Eye Disease (EAP), 7 pages.
ClinicalTrials.gov Identifier: NCT04583735—A Study Evaluating TEPEZZA® Treatment in Patients With Chronic (Inactive) Thyroid Eye Disease, 9 pages.
Diniz et al., "Early Experience With the Clinical Use of Teprotumumab in a Heterogenous Thyroid Eye Disease Population". Ophthalmic Plast Reconstr Surg. (2021) doi: 10.1097/IOP.0000000000001959. Epub ahead of print. PMID: 33710036.
Dolgin, "IGF-1R drugs travel from cancer cradle to Graves'. Nat Biotechnol". (2020) 38(4):385-388. doi: 10.1038/s41587-020-0481-8. PMID: 32265558.
Dosiou et al, "Thyroid Eye Disease: Navigating The New Treatment Landscape." Journal of the Endocrine Society (2021).
Douglas et al., "Aberrant expression of the insulin-like growth factor-1 receptor by T cells from patients with Graves' disease may carry functional consequences for disease pathogenesis". J Immunol. (2007) 178(5):3281-7. doi: 10.4049/jimmunol.178.5.3281. PMID: 17312178.
Douglas et al., "B cells from patients with Graves' disease aberrantly express the IGF-1 receptor: implications for disease pathogenesis". J Immunol. (2008) 181(8):5768-74. doi: 10.4049/jimmunol.181.8.5768. PMID: 18832736; PMCID: PMC2562248.
Douglas et al., "Teprotumumab for the Treatment of Active Thyroid Eye Disease". N Engl J Med. (2020) 382(4):341-352. doi: 10.1056/NEJMoa1910434. PMID: 31971679.
Douglas, "Teprotumumab, an insulin-lik growth factor-1 receptor antagonist antibody, in the treatment of active thyroid eye disease: a focus on proptosis", Spring Nature (2019) 33:13-190.
Edmunds et al., "Investigation of candidate biomarkers in Graves' disease and thyroid-associated ophthalmopathy". Diss. University of Birmingham, (2016).
Ghosh et al., "Natalizumab for Active Chrohn's Disease", New Engl. J. Med. (2003) 348:24-32.
Herold, et al., "ANTI-CD3 Monoclonal Antibody in New-Onset Type 1 Diabetes Mellitus", New Engl. J. Med. (2002) vol. 346, No. 22, pp. 1692-1698.
Hoa et al., "Nuclear targeting of IGF-1 receptor in orbital fibroblasts from Graves' disease: apparent role of ADAM17". PLoS One. (2012) 7(4):e34173. doi: 10.1371/journal.pone.0034173. Epub Apr. 10, 2012. PMID: 22506015; PMCID: PMC3323600.
Holliger et al., ""Diabodies": Small bivalent and bispecific antibody fragments", Proc. Natl. Acad. Sci. USA (1993) vol. 90 pp. 6444-6448.
Holliger et al., "Engineered Antibody Fragments and the Rise of Single Domains", Nat. Biotechnol. (2005) vol. 23, No. 9, pp. 1126-1136.
International Preliminary Report on Patentability received in PCT Appl. No. PCT/US2021/054907 mailed Apr. 13, 2023.
International Preliminary Report on Patentability received in PCT Appl. No. PCT/US2021/054914 mailed Apr. 13, 2023.
International Search Report and Written Opinion for International PCT Application No. PCT/US2022/074764 dated Nov. 4, 2022.
International Search Report and Written Opinion received in Appl. No. PCT/US2021/054907 mailled Feb. 23, 2022.
International Search Report and Written Opinion received in PCT Appl. No. PCT/US2021/054914 mailed Feb. 23, 2022 .
Jain et al., "Teprotumumab reduces extraocular muscle and orbital fat vol. in thyroid eye disease". Br J Ophthalmol. (2020) bjophthalmol-2020-317806. doi: 10.1136/bjophthalmol-2020-317806. Epub ahead of print. PMID: 33172865.
Janssen et al., "Lessons Learned from Targeting IGF-I Receptor in Thyroid-Associated Ophthalmopathy. Cells". (2021) 10(2):383. doi: 10.3390/cells10020383. PMID: 33673340; PMCID: PMC7917650.
Kabat, et al., "Unusual Distributions of Amino Acids in Complementarity-determining (Hypervariable) Segments of Heavy and Light Chains of Immunoglobulins and Their Possible Roles in Specificity of Antibody-combininb Sites*", J Biol Chem (1977) vol. 252, No. 19, pp. 6609-6616.
Kahaly et al., "Management of Graves Thyroidal and Extrathyroidal Disease: An Update". J Clin Endocrinol Metab. (2020) 105(12):3704-20. doi: 10.1210/clinem/dgaa646. PMID: 32929476; PMCID: PMC7543578.
Keenan et al., "A First-in-Human Phase 1 Randomized, Single-Ascending Dose Study of Lonigutamab, an Anti-IGF-1R Monoclonal Antibody, in Healthy Volunteers", Presented at the 49th North American Neuro-Ophthalmology Society Annual Meeting, Mar. 11-16, 2023, Orlando, FL.
Krieger et al., "Bidirectional TSH and IGF-1 receptor cross talk mediates stimulation of hyaluronan secretion by Graves' disease immunoglobins". J Clin Endocrinol Metab. (2015( (3):1071-7. doi: 10.1210/jc.2014-3566. Epub Dec. 8, 2014. PMID: 25485727; PMCID: PMC4333041.

(56) References Cited

OTHER PUBLICATIONS

Krieger et al., "Is There Evidence for IGF1R-Stimulating Abs in Graves' Orbitopathy Pathogenesis?" Int J Mol Sci. (2020) 21(18):6561. doi: 10.3390/ijms21186561. PMID: 32911689; PMCID: PMC7555308.

Krieger et al., "Thyrotropin/IGF-1 Receptor Cross Talk in Graves' Ophthalmopathy Pathogenesis". J Clin Endocrinol Metab. (2016) 101(6):2340-7. doi: 10.1210/jc.2016-1315. Epub Apr. 4, 2016. PMID: 27043163; PMCID: PMC4891793.

Kumar et al., "A stimulatory thyrotropin receptor antibody enhances hyaluronic acid synthesis in graves' orbital fibroblasts: inhibition by an IGF-I receptor blocking antibody". J Clin Endocrinol Metab. (2012) 97(5):1681-7. doi: 10.1210/jc.2011-2890. Epub May 7, 2012. PMID: 22399503; PMCID: PMC3339886.

Lanzolla et al., "Putative protective role of autoantibodies against the insulin-like growth factor-1 receptor in Graves' Disease: results of a pilot study". J Endocrinol Invest. (2020) 3(12):1759-1768. doi: 10.1007/s40618-020-01341.2. Epub Jun. 25, 2020. PMID: 32583374.

Lathe, et al., "Synthetic Oligonucleotide Probes Deduced from Amino Acid Sequence Data Theoretical and Practical Considerations", J. Molec. Biol. (1985) 183:1 12.

Lipsky et al., "Infliximab and Methotrexate in the Treatment of Rheumatoid Arthritis", New Engl. J. Med. (2000) 343:1594-1602).

Liu et al. "Chimeric mouse-human IgG1 antibody that can mediate lysis of cancer cells", Proc. Natl. Acad. Sci., USA (1987) vol. 84, pp. 3439-3443.

Liu et al., "Production of a mouse-human chimeric monoclonal antibody to CD20 with potent Fc-dependent biologic activity.", J Immunology (1987) 139:3521-3526.

Liu, et al., "Randomised, double blind, placebo controlled study of interferon ß-1a in a relapsing-remitting multiple sclerosis analysed by area under disability/time curves" J. Neurol. Neurosurg. Psych. (1999) 67:451-456.

Marinò et al., "Serum antibodies against the insulin-like growth factor-1 receptor (IGF-1R) in Graves' disease and Graves' orbitopathy". J Endocrinol Invest. (2019) 42(4):471-480. doi: 10.1007/s40618-018-0943-8. Epub Aug. 21, 2018. PMID: 30132285.

Markham, "Teprotumumab: First Approval. Drugs". (2020) 80(5):509-512. doi: 10.1007/s40265-020-01287-y. PMID: 32157641.

Marks et al., "By-passign Immunization Human Antibodies from V-gene Libraries Displayed on Phage", J. Mol. Biol. (1991) 222:pp. 581-597.

Milgrom et al., "Treatment of Allergic Asthma with Monoclonal Anti-IgE Antibody," New Engl. J. Med. (1999) 341:1966-1973.

Morgan et al., "Thyrotropin and Insulin-Like Growth Factor 1 Receptor Crosstalk Upregulates Sodium-Iodide Symporter Expression in Primary Cultures of Human Thyrocytes". Thyroid. (2016) (12):1794-1803. doi: 10.1089/thy.2016.0323. Epub Oct. 18, 2016. PMID: 27638195; PMCID: PMC5175432.

Morrison et al., "Chimeric human antibody molecules: Mouse antigen-binding domains with human constant region domains", Proc. Natl. Acad. Sci. USA (1984) vol. 81: pp. 6851-6855.

Mueller et al,. "Humanized Porcine VCAM-Specific Monoclonal Antibodies With Chimeric IgG2/G4 Constant Regions Block Human Leukocyte Binding to Porcine Endothelial Cells", Mol Immunol (1997) vol. 34, No. 6. pp. 441-452.

Muyldermans et al., "Recognition of antigens by single-domain fragments: the superfluous luxury of paired domains", Trends Biochem. Sci. (2001) vol. 26, No. 4, pp. 230-235.

Neumann et al., "Targeting TSH and IGF-1 Receptors to Treat Thyroid Eye Disease". Eur Thyroid J. (2020) (Suppl 1):59-65. doi: 10.1159/000511538. Epub Nov. 2, 2020. PMID: 33511086; PMCID: PMC7802449.

Non-Final Office Action for U.S. Appl. No. 17/724,639 dated Aug. 19, 2022.

Non-Final Office Action for U.S. Appl. No. 17/818,798 dated Jun. 27, 2023.

Non-Final Office Action from U.S. Appl. No. 17/450,872 dated Jan. 26, 2023.

Osher et al., "Therapeutic Targeting of the IGF Axis. Cells". (2019) 8(8):895. doi: 10.3390/cells8080895. PMID: 31416218; PMCID: PMC6721736.

Ozzello et al., "Early experience with teprotumumab for chronic thyroid eye disease". Am J Ophthalmol Case Rep. (2020) 19:100744. doi: 10.1016/j.ajoc.2020.100744. PMID: 32462101; PMCID: PMC7243051.

Place et al., "Inhibiting thyrotropin/insulin-like growth factor 1 receptor crosstalk to treat Graves' ophthalmopathy: studies in orbital fibroblasts in vitro". Br J Pharmacol. (2017) 174(4):328-340. doi: 10.1111/bph.13693. Epub Jan. 2, 20177. PMID: 27987211; PMCID: PMC5289943.

Pluckthun (1994) The Pharmacology of Monoclonal Antibodies, vol. 113, Rosenburg and Moore eds. Springer-Verlag, New York, pp. 269-315.

Portielji et al., "IL-12: A Promising Adjuvant for Cancer Vaccination," Cancer Immunol. Immunother. (2003) 52:133-144.

Presta, "Molecular mechanisms in allergy and clinical immunology, Selection, design, and engineering of therapeutic antibodies", J. Allergy Clin. Immunol. (2005) 116:731-736.

Pritchard et al., "Immunoglobulin activation of T cell chemoattractant expression in fibroblasts from patients with Graves' disease is mediated through the insulin-like growth factor I receptor pathway". J Immunol. (2003) 170 (12):6348-54. doi: 10.4049/jimmunol.170.12.6348. PMID: 12794168.

Reichmann et al., "Single domain antibodies: comparison of camel VH and camelised human VH domains", J. Immunol. Methods (1999) pp. 231:25.

Riechmann et al., "Reshaping human antibodies for therapy". Nature (1988). 332 (6162): 332-323.

Safo et al., "A case of ulcerative colitis associated with teprotumumab treatment for thyroid eye disease". Am J Ophthalmol Case Rep. (2021) 22:101069. doi: 10.1016/j.ajoc.2021.101069. PMID: 33817409; PMCID: PMC8008157.

Salvi el al., "Medical Treatment of Graves' Orbitophathy", Horm Metab Res (2015) 47:779-788.

Salvi, "Immunotherapy for Graves' ophthalmopathy", curr Opin Endocrinol Diabetes Obes. (2014) 21 (5):409-14.

Slamon et al., "Use of Chemotherapy Plus a Monoclonal Antibodty Against HER2 for Metastatic Breast Cancer That Overexpresses HER2", N Engl. J. Med. (2001) vol. 344, No. 11, pp. 783-792.

Slentz et al., "Teprotumumab: a novel therapeutic monoclonal antibody for thyroid-associated ophthalmopathy". Expert Opin Investig Drugs. (2020) (7):645-649. doi: 10.1080/13543784.2020.1772752. Epub Jun. 10, 2020. PMID: 32429706; PMCID: PMC7529924.

Smith et al. "Immunoglobulins from patients with Graves' disease induce hyaluronan synthesis in their orbital fibroblasts through the self-antigen, insulin-like growth factor-I receptor.", J Clin Endocrinol Metab. (2004) 89 (10):5076-80. doi: 10.1210/jc.2004-0716. PMID: 15472208.

Smith et al., "Teprotumumab for Thyroid-Associated Ophthalmopathy". N Engl J Med. (2017) 376(18): 1748-1761. doi: 10.1056/NEJMoa1614949. PMID: 28467880; PMCID: PMC5718164.

Smith, "Teprotumumab as a Novel Therapy for Thyroid-Associated Ophthalmopathy". Front Endocrinol (Lausanne). (2020) 11:610337. doi: 10.3389/fendo.2020.610337. PMID: 33391187; PMCID: PMC7774640.

Smith, T. J., "Teprotumumab for Thyroid-Associated Ophthalmopathy", N Engl J Med (2017) 376:18, pp. 1748-1761.

Storz et al., "Intellectual property protection", MAbs. (2011) 3(3): 15530, pp. 310-317.

Taylor et al., "New insights into the pathogenesis and nonsurgical management of Graves orbitopathy". Nat Rev Endocrinol. (2020) 16(2):104-116. doi: 10.1038/s41574-019-0305-4. Epub Dec. 30, 2019. PMID: 31889140.

Tsui et al., "Evidence for an association between thyroid-stimulating hormone and insulin-like growth factor 1 receptors: a tale of two antigens implicated in Graves' disease". J Immunol. (2008) 181(6):4397-405. doi: 10.4049/jimmunol.181.6.4397. PMID: 18768899; PMCID: PMC2775538.

Tsurushita et al., "Humanization of a chicken anti-IL-12 monoclonal antibody" Journal of Immunological Methods (2004) 295, pp. 9-19.

(56) References Cited

OTHER PUBLICATIONS

Ugradar et al., "Improvement of asymmetric thyroid eye disease with teprotumumab", Br J Ophthalmol. (2021): bjophthalmol-2020-318314. doi: 10.1136/bjophthalmol-2020-318314. Epub ahead of print. PMID: 33579690.
Ugradar et al., "Teprotumumab for non-inflammatory thyroid eye disease (TED): evidence for increased IGF-1R expression. Eye", Lond (2020) doi: 10.1038/s41433-020-01297-w. Epub ahead of print. PMID: 33221815.
Ugrader et al., "A Paradigm Shift in the Management of Thyroid Eye Disease How Teprotumumab Has Changed the Therapeutic Interface," J. Neuroophthalmol. (Mar. 2022) 42(1), pp. 26-34. (Abstract Only).
Ugrader et al., "Teprotumumab for the Treatment of Chronic Thyroid Eye Disease," Eye (Aug. 2022) 36(8), pp. 1553-1559.
Weightman el al., "Autoantibodies to IGF-1 binding sites in thyroid associated ophthalmopathy. Autoimmunity". (1993) 16(4):251-7. doi: 10.3109/08916939309014643. PMID: 7517705.
Xin Y, Xu F, Gao Y, Bhatt N, Chamberlain J, Sile S, Hammel S, Holt RJ, Ramanathan S. Pharmacokinetics and Exposure-Response Relationship of Teprotumumab, an Insulin-Like Growth Factor-1 Receptor-Blocking Antibody, in Thyroid Eye Disease. Clin Pharmacokinet. Mar. 26, 2021. doi: 10.1007/s40262-021-01003-3. Epub ahead of print. PMID: 33768488.
Yang, et al., "A Randomized Trial of Bevacizumab, an Anti-Vascular Endothelial Groth Factor Antibody, for Metastatic Renal Cancer", New Engl. J. Med. (2003) 349:427-434.
Yu R. Thyroid function suppression after initiation of teprotumumab treatment. Endocrine. Mar. 15, 2021. doi: 10.1007/s12020-021-02676-3. Epub ahead of print. PMID: 33721204.
NANOS2023_Keenan Poster # 293 "A First-in-Human Phase 1 Randomized, Single-Ascending Dose Study of Lonigutamab, an Anti-IGF-1R Monoclonal Antibody, in Healthy Volunteers", 1 page.
International Search Report for PCT/US2024/036800 dated Jan. 16, 2025 (7 pages).
International Search Report for PCT/US2024/036803 dated Dec. 12, 2024 (8 pages).
International Search Report for PCT/US2024/045630 dated Jan. 27, 2025 (5 pages).
International Search Report for PCT/US2024/060579 dated Apr. 3, 2025 (6 pages).
International Search Report for PCT/US2025/010700 dated Apr. 24, 2025 (5 pages).
Partial Search Report for PCT/US2024/036800 dated Oct. 21, 2024 (13 pages).
Partial Search Report for PCT/US2024/036803 dated Oct. 21, 2024 (30 pages).
Partial Search Report for PCT/US2025/010706 dated May 13, 2025 (11 pages).
Partial Search Report for PCT/US2025/010718 dated May 12, 2025 (34 pages).
"A Randomized, Active Controlled, Safety and Tolerability Study of VRDN-001 in Participants With Thyroid Eye Disease (TED)", ClinicalTrials.gov, U.S. National Library of Medicine, May 23, 2024, NCT06384547 (8 pages).
"A Safety, Tolerability and Efficacy Study of Veligrotug (VRDN 001) in Healthy Volunteers and Participants with Thyroid Eye Disease (TED) (Thrive)", ClinicalTrials.gov, U.S. National Library of Medicine, Dec. 3, 2021, NCT05176639 (12 pages).
"An Efficacy, Safety, and Tolerability Study of Veligrotug (VRDN-001), in Participants with Chronic Thyroid Eye Disease (TED)", ClinicalTrials.gov, U.S. National Library of Medicine, Nov. 14, 2023, NCT06021054 (9 pages).
"International Nonproprietary Names for Pharmaceutical Substances (INN)", Who Drug Information, vol. 22, No. 4, Jan. 1, 2008 URL: https://cdn.who.int/media/docs/default-source/international-nonproprietary-names-(inn)/pl100.pdf?sfvrsn=acdb5b98_7 (57 pages).
Cui, Xuejiao, et al., "A review of TSHR- and IGF-1R-related pathogenesis and treatment of Graves; orbitopathy", Frontiers in Immunology, vol. 19, Jan. 19, 2023 (12 pages).
Dall'Acqua, William F., et al., "Properties of human IgG1 s engineered for enhanced binding to the neonatal Fc receptor (FcRn)", Journal of Biological Chemistry, vol. 281, No. 33, Jun. 21, 2006 (pp. 23514-23524).
Foster, Kelly, et al., "6461 VRDN-003, A Full Antagonist Antibody To The IGF-1 Receptor For Thyroid Eye Disease (TED): Safety And Pharmacokinetic Results Of Subcutaneous Administration In Healthy Volunteers", Abstract, Journal of the Endocrine Society, vol. 8, Issue Supplement_1, https://pmc.ncbi.nlm.nih.gov/articles/ PMC10554431/, Nov. 1, 2024 (2 pages).
Foster, Kelly, et al., "Thyroid FRI546 VRDN-001, A Full Antagonist Antibody To IGF-1 Receptor In Development For Thyroid Eye Disease (TED): Pharmacodynamic Responses In Healthy Volunteers And Patients With Active TED", Abstract, Journal of the Endocrine Society, vol. 7, Issue Supplement_1, https://pmc.ncbi.nlm.nih.gov/articles/ PMC10554431/, Nov. 1, 2023 (2 pages).
Kamboj, et al., "Emerging Therapies in the Medical Management of Thyroid Eye Disease", Frontiers in Ophthalmology, vol. 3, 1295902, Dec. 12, 2023, DOI:10.3389/fopht.2023.1295902 (5 pages).
Ludgate, Marian, "Fibrosis in dysthyroid eye disease", Eye, vol. 34, No. 2, Dec. 16, 2019 (pp. 279-284).
Patel, Amy, et al., "A New Era in the Treatment of Thyroid Eye Disease", American Journal of Ophthalmology, vol. 208, Aug. 1, 2019 (pp. 281-288).
Robbie, Gabriel J., et al., "A Novel Investigational Fc-Modified Humanized Monoclonal Antibody, Motavizumab-YTE, Has an Extended Half-Life in Healthy Adults", Antimicrobial Agents and Chemotherapy, vol. 57, No. 12, Sep. 30, 2013 (pp. 6147-6153).

\* cited by examiner

| Compound | Dose and ROA | AUC$_{inf}$ (µg*day/mL) | Relative Exposure | t$_{1/2}$ |
|---|---|---|---|---|
| VRDN-2700 (YTE) | 10 mg/kg, IV | 2300 ± 312 | 2.9X | 14.4 ± 4.07 |
| VRDN-2700 (YTE) | 10 mg/kg, SC | 1420 ± 62.4 | 1.8X | 12.6 ± 1.87 |
| Teprotumumab | 10 mg/kg, IV | 779 ± 79.4 | 1.0X | 6.35 ± 0.322 |

```
                              SEQUENCE LISTING

Sequence total quantity: 99
SEQ ID NO: 1              moltype = AA  length = 215
FEATURE                   Location/Qualifiers
REGION                    1..215
                          note = synthetic sequence
source                    1..215
                          mol_type = protein
                          organism = synthetic construct
SEQUENCE: 1
EIVLTQSPAT LSLSPGERAT LSCRASQSVS SYLAWYQQKP GQAPRLLIYD ASKRATGIPA   60
RFSGSGSGTD FTLTISSLEP EDFAVYYCQQ RSKWPPWTFG QGTKVESKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 2              moltype = AA  length = 448
FEATURE                   Location/Qualifiers
REGION                    1..448
                          note = synthetic sequence
source                    1..448
                          mol_type = protein
                          organism = synthetic construct
SEQUENCE: 2
QVELVESGGG VVQPGRSQRL SCAASGFTFS SYGMHWVRQA PGKGLEWVAI IWFDGSSTYY   60
ADSVRGRFTI SRDNSKNTLY LQMNSLRAED TAVYFCAREL GRRYFDLWGR GTLVSVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448
```

```
SEQ ID NO: 3            moltype = AA   length = 219
FEATURE                 Location/Qualifiers
REGION                  1..219
                        note = synthetic sequence
source                  1..219
                        mol_type = protein
                        organism = synthetic construct
SEQUENCE: 3
DIVMTQSPLS LPVTPGEPAS ISCRSSQSIV HSNGNTYLQW YLQKPGQSPQ LLIYKVSNRL   60
YGVPDRFSGS GSGTDFTLKI SRVEAEDVGV YYCFQGSHVP WTFGQGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 4            moltype = AA   length = 447
FEATURE                 Location/Qualifiers
REGION                  1..447
                        note = synthetic sequence
source                  1..447
                        mol_type = protein
                        organism = synthetic construct
SEQUENCE: 4
QVQLQESGPG LVKPSETLSL TCTVSGYSIT GGYLWNWIRQ PPGKGLEWIG YISYDGTNNY   60
KPSLKDRVTI SRDTSKNQFS LKLSSVTAAD TAVYYCARYG RVFFDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 5            moltype = AA   length = 214
FEATURE                 Location/Qualifiers
REGION                  1..214
                        note = synthetic sequence
source                  1..214
                        mol_type = protein
                        organism = synthetic construct
SEQUENCE: 5
SSELTQDPAV SVALGQTVRI TCQGDSLRSY YATWYQQKPG QAPILVIYGE NKRPSGIPDR   60
FSGSSSGNTA SLTITGAQAE DEADYYCKSR DGSGQHLVFG GGTKLTVLGQ PKAAPSVTLF  120
PPSSEELQAN KATLVCLISD FYPGAVTVAW KADSSPVKAG VETTTPSKQS NNKYAASSYL  180
SLTPEQWKSH RSYSCQVTHE GSTVEKTVAP AECS                              214

SEQ ID NO: 6            moltype = AA   length = 460
FEATURE                 Location/Qualifiers
REGION                  1..460
                        note = synthetic sequence
source                  1..460
                        mol_type = protein
                        organism = synthetic construct
SEQUENCE: 6
EVQLVQSGAE VKKPGSSVKV SCKASGGTFS SYAISWVRQA PGQGLEWMGG IIPIFGTANY   60
AQKFQGRVTI TADKSTSTAY MELSSLRSED TAVYYCARAP LRFLEWSTQD HYYYYMDVW  120
GKGTTVTVSS ASTKGPSVFP LAPSSKSTSG GTAALGCLVK DYFPEPVTVS WNSGALTSGV  180
HTFPAVLQSS GLYSLSSVVT VPSSSLGTQT YICNVNHKPS NTKVDKKVEP KSCDKTHTCP  240
PCPAPELLGG PSVFLFPPKP KDTLMISRTP EVTCVVVDVS HEDPEVKFNW YVDGVEVHNA  300
KTKPREEQYN STYRVVSVLT VLHQDWLNGK EYKCKVSNKA LPAPIEKTIS KAKGQPREPQ  360
VYTLPPSREE MTKNQVSLTC LVKGFYPSDI AVEWESNGQP ENNYKTTPPV LDSDGSFFLY  420
SKLTVDKSRW QQGNVFSCSV MHEALHNHYT QKSLSLSPGK                        460

SEQ ID NO: 7            moltype = AA   length = 214
FEATURE                 Location/Qualifiers
REGION                  1..214
                        note = synthetic sequence
source                  1..214
                        mol_type = protein
                        organism = synthetic construct
SEQUENCE: 7
DIQMTQFPSS LSASVGDRVT ITCRASQGIR NDLGWYQQKP GKAPKRLIYA ASRLHRGVPS   60
RFSGSGSGTE FTLTISSLQP EDFATYYCLQ HNSYPCSFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 8            moltype = AA   length = 450
FEATURE                 Location/Qualifiers
REGION                  1..450
                        note = synthetic sequence
source                  1..450
                        mol_type = protein
```

```
                        organism = synthetic construct
SEQUENCE: 8
EVQLLESGGG  LVQPGGSLRL  SCTASGFTFS  SYAMNWVRQA  PGKGLEWVSA  ISGSGGTTFY   60
ADSVKGRFTI  SRDNSRTTLY  LQMNSLRAED  TAVYYCAKDL  GWSDSYYYYY  GMDVWGQGTT  120
VTVSSASTKG  PSVFPLAPCS  RSTSESTAAL  GCLVKDYFPE  PVTVSWNSGA  LTSGVHTFPA  180
VLQSSGLYSL  SSVVTVPSSN  FGTQTYTCNV  DHKPSNTKVD  KTVERKCCVE  CPPCPAPPVA  240
GPSVFLFPPK  PKDTLMISRT  PEVTCVVVDV  SHEDPEVQFN  WYVDGVEVHN  AKTKPREEQF  300
NSTFRVVSVL  TVVHQDWLNG  KEYKCKVSNK  GLPAPIEKTI  SKTKGQPREP  QVYTLPPSRE  360
EMTKNQVSLT  CLVKGFYPSD  IAVEWESNGQ  PENNYKTTPP  MLDSDGSFFL  YSKLTVDKSR  420
WQQGNVFSCS  VMHEALHNHY  TQKSLSLSPG                                     450

SEQ ID NO: 9            moltype = AA  length = 219
FEATURE                 Location/Qualifiers
REGION                  1..219
                        note = synthetic sequence
source                  1..219
                        mol_type = protein
                        organism = synthetic construct
SEQUENCE: 9
DVVMTQSPLS  LPVTPGEPAS  ISCRSSQSLL  HSNGYNYLDW  YLQKPGQSPQ  LLIYLGSNRA   60
SGVPDRFSGS  GSGTDFTLKI  SRVEAEDVGV  YYCMQGTHWP  LTFGQGTKVE  IKRTVAAPSV  120
FIFPPSDEQL  KSGTASVVCL  LNNFYPREAK  VQWKVDNALQ  SGNSQESVTE  QDSKDSTYSL  180
SSTLTLSKAD  YEKHKVYACE  VTHQGLSSPV  TKSFNRGEC                          219

SEQ ID NO: 10           moltype = AA  length = 449
FEATURE                 Location/Qualifiers
REGION                  1..449
                        note = synthetic sequence
source                  1..449
                        mol_type = protein
                        organism = synthetic construct
SEQUENCE: 10
QVQLQESGPG  LVKPSGTLSL  TCAVSGGSIS  SSNWWSWVRQ  PPGKGLEWIG  EIYHSGSTNY   60
NPSLKSRVTI  SVDKSKNQFS  LKLSSVTAAD  TAVYYCARWT  GRTDAFDIWG  QGTMVTVSSA  120
STKGPSVFPL  APSSKSTSGG  TAALGCLVKD  YFPEPVTVSW  NSGALTSGVH  TFPAVLQSSG  180
LYSLSSVVTV  PSSSLGTQTY  ICNVNHKPSN  TKVDKKVEPK  SCDKTHTCPP  CPAPELLGGP  240
SVFLFPPKPK  DTLMISRTPE  VTCVVVDVSH  EDPEVKFNWY  VDGVEVHNAK  TKPREEQYNS  300
TYRVVSVLTV  LHQDWLNGKE  YKCKVSNKAL  PAPIEKTISK  AKGQPREPQV  YTLPPSRDEL  360
TKNQVSLTCL  VKGFYPSDIA  VEWESNGQPE  NNYKTTPPVL  DSDGSFFLYS  KLTVDKSRWQ  420
QGNVFSCSVM  HEALHNHYTQ  KSLSLSPGK                                      449

SEQ ID NO: 11           moltype = AA  length = 214
FEATURE                 Location/Qualifiers
REGION                  1..214
                        note = synthetic sequence
source                  1..214
                        mol_type = protein
                        organism = synthetic construct
SEQUENCE: 11
EIVLTQSPGT  LSVSPGERAT  LSCRASQSIG  SSLHWYQQKP  GQAPRLLIKY  ASQSLSGIPD   60
RFSGSGSGTD  FTLTISRLEP  EDFAVYYCHQ  SSRLPHTFGQ  GTKVEIKRTV  AAPSVFIFPP  120
SDEQLKSGTA  SVVCLLNNFY  PREAKVQWKV  DNALQSGNSQ  ESVTEQDSKD  STYSLSSTLT  180
LSKADYEKHK  VYACEVTHQG  LSSPVTKSFN  RGEC                               214

SEQ ID NO: 12           moltype = AA  length = 448
FEATURE                 Location/Qualifiers
REGION                  1..448
                        note = synthetic sequence
source                  1..448
                        mol_type = protein
                        organism = synthetic construct
SEQUENCE: 12
EVQLVQSGGG  LVKPGGSLRL  SCAASGFTFS  SFAMHWVRQA  PGKGLEWISV  IDTRGATYYA   60
DSVKGRFTIS  RDNAKNSLYL  QMNSLRAEDT  AVYYCARLGN  FYYGMDVWGQ  GTTVTVSSAS  120
TKGPSVFPLA  PSSKSTSGGT  AALGCLVKDY  FPEPVTVSWN  SGALTSGVHT  FPAVLQSSGL  180
YSLSSVVTVP  SSSLGTQTYI  CNVNHKPSNT  KVDKKVEPKS  CDKTHTCPPC  PAPELLGGPS  240
VFLFPPKPKD  TLMISRTPEV  TCVVVDVSHE  DPEVKFNWYV  DGVEVHNAKT  KPREEQYNST  300
YRVVSVLTVL  HQDWLNGKEY  KCKVSNKALP  APIEKTISKA  KGQPREPQVY  TLPPSRDELT  360
KNQVSLTCLV  KGFYPSDIAV  EWESNGQPEN  NYKTTPPVLD  SDGSFFLYSK  LTVDKSRWQQ  420
GNVFSCSVMH  EALHNHYTQK  SLSLSPGK                                       448

SEQ ID NO: 13           moltype = AA  length = 113
FEATURE                 Location/Qualifiers
REGION                  1..113
                        note = synthetic sequence
source                  1..113
                        mol_type = protein
                        organism = synthetic construct
SEQUENCE: 13
```

```
DVVMTQTPLS LPVSLGDPAS ISCRSSQSIV HSNVNTYLEW YLQKPGQSPR LLIYKVSNRF   60
SGVPDRFSGS GAGTDFTLRI SRVEAEDLGI YYCFQGSHVP PTFGGGTKLE IKR         113

SEQ ID NO: 14           moltype = AA  length = 124
FEATURE                 Location/Qualifiers
REGION                  1..124
                        note = synthetic sequence
source                  1..124
                        mol_type = protein
                        organism = synthetic construct
SEQUENCE: 14
QVQLVQSGAE VVKPGASVKL SCKASGYTFT SYWMHWVKQR PGQGLEWIGE INPSNGRTNY   60
NQKFQGKATL TVDKSSSTAY MQLSSLTSED SAVYYFARGR PDYYGSSKWY FDVWGQGTTV  120
TVSS                                                              124

SEQ ID NO: 15           moltype = AA  length = 107
FEATURE                 Location/Qualifiers
REGION                  1..107
                        note = synthetic sequence
source                  1..107
                        mol_type = protein
                        organism = synthetic construct
SEQUENCE: 15
DIQMTQSPLS LSASVGDRVT ITCQASRDIR NYLNWYQQKP GKAPKLLIYD ASSLQTGVPS   60
RFGGSGSGTD FSFTIGSLQP EDIATYYCQQ FDSLPHTFGQ GTKLEIK                107

SEQ ID NO: 16           moltype = AA  length = 120
FEATURE                 Location/Qualifiers
REGION                  1..120
                        note = synthetic sequence
source                  1..120
                        mol_type = protein
                        organism = synthetic construct
SEQUENCE: 16
EVQLLESGGG LVQPGGSLRL SCAASGFTFS IYRMQWVRQA PGKGLEWVSG ISPSGGTTWY   60
ADSVKGRFTI SRDNSKNTLY LQMNSLRAED TAVYYCARWS GGSGYAFDIW GQGTMVTVSS  120

SEQ ID NO: 17           moltype = AA  length = 11
FEATURE                 Location/Qualifiers
REGION                  1..11
                        note = synthetic sequence
source                  1..11
                        mol_type = protein
                        organism = synthetic construct
SEQUENCE: 17
RASQSVSSYL A                                                       11

SEQ ID NO: 18           moltype = AA  length = 7
FEATURE                 Location/Qualifiers
REGION                  1..7
                        note = synthetic sequence
source                  1..7
                        mol_type = protein
                        organism = synthetic construct
SEQUENCE: 18
DASKRAT                                                            7

SEQ ID NO: 19           moltype = AA  length = 10
FEATURE                 Location/Qualifiers
REGION                  1..10
                        note = synthetic sequence
source                  1..10
                        mol_type = protein
                        organism = synthetic construct
SEQUENCE: 19
QQRSKWPPWT                                                         10

SEQ ID NO: 20           moltype = AA  length = 5
FEATURE                 Location/Qualifiers
REGION                  1..5
                        note = synthetic sequence
source                  1..5
                        mol_type = protein
                        organism = synthetic construct
SEQUENCE: 20
SYGMH                                                              5

SEQ ID NO: 21           moltype = AA  length = 17
FEATURE                 Location/Qualifiers
```

```
REGION                    1..17
                          note = synthetic sequence
source                    1..17
                          mol_type = protein
                          organism = synthetic construct
SEQUENCE: 21
IIWFDGSSTY YADSVRG                                                         17

SEQ ID NO: 22             moltype = AA  length = 9
FEATURE                   Location/Qualifiers
REGION                    1..9
                          note = synthetic sequence
source                    1..9
                          mol_type = protein
                          organism = synthetic construct
SEQUENCE: 22
ELGRRYFDL                                                                   9

SEQ ID NO: 23             moltype = AA  length = 20
FEATURE                   Location/Qualifiers
REGION                    1..20
                          note = synthetic sequence
source                    1..20
                          mol_type = protein
                          organism = synthetic construct
SEQUENCE: 23
RSSQSIVHSN GNTYLQWYLQ                                                      20

SEQ ID NO: 24             moltype = AA  length = 7
FEATURE                   Location/Qualifiers
REGION                    1..7
                          note = synthetic sequence
source                    1..7
                          mol_type = protein
                          organism = synthetic construct
SEQUENCE: 24
KVSNRLY                                                                     7

SEQ ID NO: 25             moltype = AA  length = 9
FEATURE                   Location/Qualifiers
REGION                    1..9
                          note = synthetic sequence
source                    1..9
                          mol_type = protein
                          organism = synthetic construct
SEQUENCE: 25
FQGSHVPWT                                                                   9

SEQ ID NO: 26             moltype = AA  length = 6
FEATURE                   Location/Qualifiers
REGION                    1..6
                          note = synthetic sequence
source                    1..6
                          mol_type = protein
                          organism = synthetic construct
SEQUENCE: 26
GGYLWN                                                                      6

SEQ ID NO: 27             moltype = AA  length = 16
FEATURE                   Location/Qualifiers
REGION                    1..16
                          note = synthetic sequence
source                    1..16
                          mol_type = protein
                          organism = synthetic construct
SEQUENCE: 27
YISYDGTNNY KPSLKD                                                          16

SEQ ID NO: 28             moltype = AA  length = 8
FEATURE                   Location/Qualifiers
REGION                    1..8
                          note = synthetic sequence
source                    1..8
                          mol_type = protein
                          organism = synthetic construct
SEQUENCE: 28
YGRVFFDY                                                                    8

SEQ ID NO: 29             moltype = AA  length = 11
```

```
FEATURE                 Location/Qualifiers
REGION                  1..11
                        note = synthetic sequence
source                  1..11
                        mol_type = protein
                        organism = synthetic construct
SEQUENCE: 29
QGDSLRSYYA T                                                              11

SEQ ID NO: 30           moltype = AA  length = 7
FEATURE                 Location/Qualifiers
REGION                  1..7
                        note = synthetic sequence
source                  1..7
                        mol_type = protein
                        organism = synthetic construct
SEQUENCE: 30
GENKRPS                                                                   7

SEQ ID NO: 31           moltype = AA  length = 11
FEATURE                 Location/Qualifiers
REGION                  1..11
                        note = synthetic sequence
source                  1..11
                        mol_type = protein
                        organism = synthetic construct
SEQUENCE: 31
KSRDGSGQHL V                                                              11

SEQ ID NO: 32           moltype = AA  length = 5
FEATURE                 Location/Qualifiers
REGION                  1..5
                        note = synthetic sequence
source                  1..5
                        mol_type = protein
                        organism = synthetic construct
SEQUENCE: 32
SYAIS                                                                     5

SEQ ID NO: 33           moltype = AA  length = 17
FEATURE                 Location/Qualifiers
REGION                  1..17
                        note = synthetic sequence
source                  1..17
                        mol_type = protein
                        organism = synthetic construct
SEQUENCE: 33
GIIPIFGTAN YAQKFQG                                                        17

SEQ ID NO: 34           moltype = AA  length = 21
FEATURE                 Location/Qualifiers
REGION                  1..21
                        note = synthetic sequence
source                  1..21
                        mol_type = protein
                        organism = synthetic construct
SEQUENCE: 34
APLRFLEWST QDHYYYYMD V                                                    21

SEQ ID NO: 35           moltype = AA  length = 11
FEATURE                 Location/Qualifiers
REGION                  1..11
                        note = synthetic sequence
source                  1..11
                        mol_type = protein
                        organism = synthetic construct
SEQUENCE: 35
RASQGIRNDL G                                                              11

SEQ ID NO: 36           moltype = AA  length = 7
FEATURE                 Location/Qualifiers
REGION                  1..7
                        note = synthetic sequence
source                  1..7
                        mol_type = protein
                        organism = synthetic construct
SEQUENCE: 36
AASRLHR                                                                   7
```

```
SEQ ID NO: 37              moltype = AA  length = 9
FEATURE                    Location/Qualifiers
REGION                     1..9
                           note = synthetic sequence
source                     1..9
                           mol_type = protein
                           organism = synthetic construct
SEQUENCE: 37
LQHNSYPCS                                                                9

SEQ ID NO: 38              moltype = AA  length = 5
FEATURE                    Location/Qualifiers
REGION                     1..5
                           note = synthetic sequence
source                     1..5
                           mol_type = protein
                           organism = synthetic construct
SEQUENCE: 38
SYAMN                                                                    5

SEQ ID NO: 39              moltype = AA  length = 17
FEATURE                    Location/Qualifiers
REGION                     1..17
                           note = synthetic sequence
source                     1..17
                           mol_type = protein
                           organism = synthetic construct
SEQUENCE: 39
AISGSGGTTF YADSVKG                                                      17

SEQ ID NO: 40              moltype = AA  length = 16
FEATURE                    Location/Qualifiers
REGION                     1..16
                           note = synthetic sequence
source                     1..16
                           mol_type = protein
                           organism = synthetic construct
SEQUENCE: 40
DLGWSDSYYY YYGMDV                                                       16

SEQ ID NO: 41              moltype = AA  length = 16
FEATURE                    Location/Qualifiers
REGION                     1..16
                           note = synthetic sequence
source                     1..16
                           mol_type = protein
                           organism = synthetic construct
SEQUENCE: 41
RSSQSLLHSN GYNYLD                                                       16

SEQ ID NO: 42              moltype = AA  length = 6
FEATURE                    Location/Qualifiers
REGION                     1..6
                           note = synthetic sequence
source                     1..6
                           mol_type = protein
                           organism = synthetic construct
SEQUENCE: 42
LGSNRA                                                                   6

SEQ ID NO: 43              moltype = AA  length = 9
FEATURE                    Location/Qualifiers
REGION                     1..9
                           note = synthetic sequence
source                     1..9
                           mol_type = protein
                           organism = synthetic construct
SEQUENCE: 43
MQGTHWPLT                                                                9

SEQ ID NO: 44              moltype = AA  length = 7
FEATURE                    Location/Qualifiers
REGION                     1..7
                           note = synthetic sequence
source                     1..7
                           mol_type = protein
                           organism = synthetic construct
SEQUENCE: 44
SSSNWWS                                                                  7
```

```
SEQ ID NO: 45          moltype = AA   length = 16
FEATURE                Location/Qualifiers
REGION                 1..16
                       note = synthetic sequence
source                 1..16
                       mol_type = protein
                       organism = synthetic construct
SEQUENCE: 45
EIYHSGSTNY NPSLKS                                                           16

SEQ ID NO: 46          moltype = AA   length = 10
FEATURE                Location/Qualifiers
REGION                 1..10
                       note = synthetic sequence
source                 1..10
                       mol_type = protein
                       organism = synthetic construct
SEQUENCE: 46
WTGRTDAFDI                                                                  10

SEQ ID NO: 47          moltype = AA   length = 11
FEATURE                Location/Qualifiers
REGION                 1..11
                       note = synthetic sequence
source                 1..11
                       mol_type = protein
                       organism = synthetic construct
SEQUENCE: 47
RASQSIGSSL H                                                                11

SEQ ID NO: 48          moltype = AA   length = 7
FEATURE                Location/Qualifiers
REGION                 1..7
                       note = synthetic sequence
source                 1..7
                       mol_type = protein
                       organism = synthetic construct
SEQUENCE: 48
YASQSLS                                                                      7

SEQ ID NO: 49          moltype = AA   length = 9
FEATURE                Location/Qualifiers
REGION                 1..9
                       note = synthetic sequence
source                 1..9
                       mol_type = protein
                       organism = synthetic construct
SEQUENCE: 49
HQSSRLPHT                                                                    9

SEQ ID NO: 50          moltype = AA   length = 5
FEATURE                Location/Qualifiers
REGION                 1..5
                       note = synthetic sequence
source                 1..5
                       mol_type = protein
                       organism = synthetic construct
SEQUENCE: 50
SFAMH                                                                        5

SEQ ID NO: 51          moltype = AA   length = 16
FEATURE                Location/Qualifiers
REGION                 1..16
                       note = synthetic sequence
source                 1..16
                       mol_type = protein
                       organism = synthetic construct
SEQUENCE: 51
VIDTRGATYY ADSVKG                                                           16

SEQ ID NO: 52          moltype = AA   length = 10
FEATURE                Location/Qualifiers
REGION                 1..10
                       note = synthetic sequence
source                 1..10
                       mol_type = protein
                       organism = synthetic construct
SEQUENCE: 52
```

```
LGNFYYGMDV                                                                      10

SEQ ID NO: 53           moltype = AA  length = 16
FEATURE                 Location/Qualifiers
REGION                  1..16
                        note = synthetic sequence
source                  1..16
                        mol_type = protein
                        organism = synthetic construct
SEQUENCE: 53
RSSQSIVHSN VNTYLE                                                               16

SEQ ID NO: 54           moltype = AA  length = 7
FEATURE                 Location/Qualifiers
REGION                  1..7
                        note = synthetic sequence
source                  1..7
                        mol_type = protein
                        organism = synthetic construct
SEQUENCE: 54
KVSNRFS                                                                          7

SEQ ID NO: 55           moltype = AA  length = 9
FEATURE                 Location/Qualifiers
REGION                  1..9
                        note = synthetic sequence
source                  1..9
                        mol_type = protein
                        organism = synthetic construct
SEQUENCE: 55
FQGSHVPPT                                                                        9

SEQ ID NO: 56           moltype = AA  length = 5
FEATURE                 Location/Qualifiers
REGION                  1..5
                        note = synthetic sequence
source                  1..5
                        mol_type = protein
                        organism = synthetic construct
SEQUENCE: 56
SYWMH                                                                            5

SEQ ID NO: 57           moltype = AA  length = 18
FEATURE                 Location/Qualifiers
REGION                  1..18
                        note = synthetic sequence
source                  1..18
                        mol_type = protein
                        organism = synthetic construct
SEQUENCE: 57
GEINPSNGRT NYNQKFQG                                                             18

SEQ ID NO: 58           moltype = AA  length = 15
FEATURE                 Location/Qualifiers
REGION                  1..15
                        note = synthetic sequence
source                  1..15
                        mol_type = protein
                        organism = synthetic construct
SEQUENCE: 58
GRPDYYGSSK WYFDV                                                                15

SEQ ID NO: 59           moltype = AA  length = 11
FEATURE                 Location/Qualifiers
REGION                  1..11
                        note = synthetic sequence
source                  1..11
                        mol_type = protein
                        organism = synthetic construct
SEQUENCE: 59
QASRDIRNYL N                                                                    11

SEQ ID NO: 60           moltype = AA  length = 7
FEATURE                 Location/Qualifiers
REGION                  1..7
                        note = synthetic sequence
source                  1..7
                        mol_type = protein
                        organism = synthetic construct
```

```
SEQUENCE: 60
DASSLQT                                                                7

SEQ ID NO: 61           moltype = AA  length = 9
FEATURE                 Location/Qualifiers
REGION                  1..9
                        note = synthetic sequence
source                  1..9
                        mol_type = protein
                        organism = synthetic construct
SEQUENCE: 61
QQFDSLPHT                                                              9

SEQ ID NO: 62           moltype = AA  length = 5
FEATURE                 Location/Qualifiers
REGION                  1..5
                        note = synthetic sequence
source                  1..5
                        mol_type = protein
                        organism = synthetic construct
SEQUENCE: 62
IYRMQ                                                                  5

SEQ ID NO: 63           moltype = AA  length = 16
FEATURE                 Location/Qualifiers
REGION                  1..16
                        note = synthetic sequence
source                  1..16
                        mol_type = protein
                        organism = synthetic construct
SEQUENCE: 63
GISPSGGTTW YADSVK                                                     16

SEQ ID NO: 64           moltype = AA  length = 11
FEATURE                 Location/Qualifiers
REGION                  1..11
                        note = synthetic sequence
source                  1..11
                        mol_type = protein
                        organism = synthetic construct
SEQUENCE: 64
WSGGSGYAFD I                                                          11

SEQ ID NO: 65           moltype = AA  length = 663
FEATURE                 Location/Qualifiers
REGION                  1..663
                        note = synthetic sequence
source                  1..663
                        mol_type = protein
                        organism = synthetic construct
SEQUENCE: 65
EIVLTQSPAT LSLSPGERAT LSCRASQSVS SYLAWYQQKP GQAPRLLIYD ASKRATGIPA     60
RFSGSGSGTD FTLTISSLEP EDFAVYYCQQ RSKWPPWTFG QGTKVESKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGECQVELV ESGGGVVQPG RSQRLSCAAS    240
GFTFSSYGMH WVRQAPGKGL EWVAIIWFDG SSTYYADSVR GRFTISRDNS KNTLYLQMNS    300
LRAEDTAVYF CARELGRRYF DLWGRGTLVS VSSASTKGPS VFPLAPSSKS TSGGTAALGC    360
LVKDYFPEPV TVSWNSGALT SGVHTFPAVL QSSGLYSLSS VVTVPSSSLG TQTYICNVNH    420
KPSNTKVDKK VEPKSCDKTH TCPPCPAPEL LGGPSVFLFP PKPKDTLMIS RTPEVTCVVV    480
DVSHEDPEVK FNWYVDGVEV HNAKTKPREE QYNSTYRVVS VLTVLHQDWL NGKEYKCKVS    540
NKALPAPIEK TISKAKGQPR EPQVYTLPPS RDELTKNQVS LTCLVKGFYP SDIAVEWESN    600
GQPENNYKTT PPVLDSDGSF FLYSKLTVDK SRWQQGNVFS CSVMHEALHN HYTQKSLSLS    660
PGK                                                                  663

SEQ ID NO: 66           moltype = AA  length = 666
FEATURE                 Location/Qualifiers
REGION                  1..666
                        note = synthetic sequence
source                  1..666
                        mol_type = protein
                        organism = synthetic construct
SEQUENCE: 66
DIVMTQSPLS LPVTPGEPAS ISCRSSQSIV HSNGNTYLQW YLQKPGQSPQ LLIYKVSNRL     60
YGVPDRFSGS GSGTDFTLKI SRVEAEDVGV YYCFQGSHVP WTFGQGTKVE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGECQ VQLQESGPGL VKPSETLSLT    240
CTVSGYSITG GYLWNWIRQP PGKGLEWIGY ISYDGTNNYK PSLKDRVTIS RDTSKNQFSL    300
KLSSVTAADT AVYYCARYGR VFFDYWGQGT LVTVSSASTK GPSVFPLAPS SKSTSGGTAA    360
LGCLVKDYFP EPVTVSWNSG ALTSGVHTFP AVLQSSGLYS LSSVVTVPSS SLGTQTYICN    420
```

```
VNHKPSNTKV DKRVEPKSCD KTHTCPPCPA PELLGGPSVF LFPPKPKDTL MISRTPEVTC   480
VVVDVSHEDP EVKFNWYVDG VEVHNAKTKP REEQYNSTYR VVSVLTVLHQ DWLNGKEYKC   540
KVSNKALPAP IEKTISKAKG QPREPQVYTL PPSREEMTKN QVSLTCLVKG FYPSDIAVEW   600
ESNGQPENNY KTTPPVLDSD GSFFLYSKLT VDKSRWQQGN VFSCSVMHEA LHNHYTQKSL   660
SLSPGK                                                               666

SEQ ID NO: 67           moltype = AA  length = 674
FEATURE                 Location/Qualifiers
REGION                  1..674
                        note = synthetic sequence
source                  1..674
                        mol_type = protein
                        organism = synthetic construct
SEQUENCE: 67
SSELTQDPAV SVALGQTVRI TCQGDSLRSY YATWYQQKPG QAPILVIYGE NKRPSGIPDR    60
FSGSSSGNTA SLTITGAQAE DEADYYCKSR DGSGQHLVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP AECSEVQLVQ SGAEVKKPGS SVKVSCKASG   240
GTFSSYAISW VRQAPGQGLE WMGGIIPIFG TANYAQKFQG RVTITADKST STAYMELSSL   300
RSEDTAVYYC ARAPLRFLEW STQDHYYYY MDVWGKGTTV TVSSASTKGP SVFPLAPSSK    360
STSGGTAALG CLVKDYFPEP VTVSWNSGAL TSGVHTFPAV LQSSGLYSLS SVVTVPSSSL   420
GTQTYICNVN HKPSNTKVDK KVEPKSCDKT HTCPPCPAPE LLGGPSVFLF PPKPKDTLMI   480
SRTPEVTCVV VDVSHEDPEV KFNWYVDGVE VHNAKTKPRE EQYNSTYRVV SVLTVLHQDW   540
LNGKEYKCKV SNKALPAPIE KTISKAKGQP REPQVYTLPP SREEMTKNQV SLTCLVKGFY   600
PSDIAVEWES NGQPENNYKT TPPVLDSDGS FFLYSKLTVD KSRWQQGNVF SCSVMHEALH   660
NHYTQKSLSL SPGK                                                     674

SEQ ID NO: 68           moltype = AA  length = 664
FEATURE                 Location/Qualifiers
REGION                  1..664
                        note = synthetic sequence
source                  1..664
                        mol_type = protein
                        organism = synthetic construct
SEQUENCE: 68
DIQMTQPPSS LSASVGDRVT ITCRASQGIR NDLGWYQQKP GKAPKRLIYA ASRLHRGVPS    60
RFSGSGSGTE FTLTISSLQP EDFATYYCLQ HNSYPCSFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECEVQLLE SGGGLVQPGG SLRLSCTASG   240
FTFSSYAMNW VRQAPGKGLE WVSAISGSGG TTFYADSVKG RFTISRDNSR TTLYLQMNSL   300
RAEDTAVYYC AKDLGWSDSY YYYYGMDVWG QGTTVTVSSA STKGPSVFPL APCSRSTSES   360
TAALGCLVKD YFPEPVTVSW NSGALTSGVH TFPAVLQSSG LYSLSSVVTV PSSNFGTQTY   420
TCNVDHKPSN TKVDKTVERK CCVECPPCPA PPVAGPSVFL FPPKPKDTLM ISRTPEVTCV   480
VVDVSHEDPE VQFNWYVDGV EVHNAKTKPR EEQFNSTFRV VSVLTVVHQD WLNGKEYKCK   540
VSNKGLPAPI EKTISKTKGQ PREPQVYTLP PSREEMTKNQ VSLTCLVKGF YPSDIAVEWE   600
SNGQPENNYK TTPPMLDSDG SFFLYSKLTV DKSRWQQGNV FSCSVMHEAL HNHYTQKSLS   660
LSPG                                                                 664

SEQ ID NO: 69           moltype = AA  length = 668
FEATURE                 Location/Qualifiers
REGION                  1..668
                        note = synthetic sequence
source                  1..668
                        mol_type = protein
                        organism = synthetic construct
SEQUENCE: 69
DVVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQGTHWP LTFGQGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGECQ VQLQESGPGL VKPSGTLSLT   240
CAVSGGSISS SNWWSWVRQP PGKGLEWIGE IYHSGSTNYN PSLKSRVTIS VDKSKNQFSL   300
KLSSVTAADT AVYYCARWTG RTDAFDIWGQ GTMVTVSSAS TKGPSVFPLA PSSKSTSGGT   360
AALGCLVKDY FPEPVTVSWN SGALTSGVHT FPAVLQSSGL YSLSSVVTVP SSSLGTQTYI   420
CNVNHKPSNT KVDKKVEPKS CDKTHTCPPC PAPELLGGPS VFLFPPKPKD TLMISRTPEV   480
TCVVVDVSHE DPEVKFNWYV DGVEVHNAKT KPREEQYNST YRVVSVLTVL HQDWLNGKEY   540
KCKVSNKALP APIEKTISKA KGQPREPQVY TLPPSRDELT KNQVSLTCLV KGFYPSDIAV   600
EWESNGQPEN NYKTTPPVLD SDGSFFLYSK LTVDKSRWQQ GNVFSCSVMH EALHNHYTQK   660
SLSLSPGK                                                             668

SEQ ID NO: 70           moltype = AA  length = 662
FEATURE                 Location/Qualifiers
REGION                  1..662
                        note = synthetic sequence
source                  1..662
                        mol_type = protein
                        organism = synthetic construct
SEQUENCE: 70
EIVLTQSPGT LSVSPGERAT LSCRASQSIG SSLHWYQQKP GQAPRLLIKY ASQSLSGIPD    60
RFSGSGSGTD FTLTISRLEP EDFAVYYCHQ SSRLPHTFGQ GTKVEIKRTV AAPSVFIFPP   120
```

```
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECEVQLVQ SGGGLVKPGG SLRLSCAASG    240
FTFSSFAMHW VRQAPGKGLE WISVIDTRGA TYYADSVKGR FTISRDNAKN SLYLQMNSLR    300
AEDTAVYYCA RLGNFYYGMD VWGQGTTVTV SSASTKGPSV FPLAPSSKST SGGTAALGCL    360
VKDYFPEPVT VSWNSGALTS GVHTFPAVLQ SSGLYSLSSV VTVPSSSLGT QTYICNVNHK    420
PSNTKVDKKV EPKSCDKTHT CPPCPAPELL GGPSVFLFPP KPKDTLMISR TPEVTCVVVD    480
VSHEDPEVKF NWYVDGVEVH NAKTKPREEQ YNSTYRVVSV LTVLHQDWLN GKEYKCKVSN    540
KALPAPIEKT ISKAKGQPRE PQVYTLPPSR DELTKNQVSL TCLVKGFYPS DIAVEWESNG    600
QPENNYKTTP PVLDSDGSFF LYSKLTVDKS RWQQGNVFSC SVMHEALHNH YTQKSLSLSP    660
GK                                                                  662

SEQ ID NO: 71              moltype = AA  length = 673
FEATURE                    Location/Qualifiers
REGION                     1..673
                           note = synthetic sequence
source                     1..673
                           mol_type = protein
                           organism = synthetic construct
SEQUENCE: 71
DVVMTQTPLS LPVSLGDPAS ISCRSSQSIV HSNVNTYLEW YLQKPGQSPR LLIYKVSNRF     60
SGVPDRFSGS GAGTDFTLRI SRVEAEDLGI YYCFQGSHVP PTFGGGTKLE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGECQ VQLVQSGAEV VKPGASVKLS    240
CKASGYTFTS YWMHWVKQRP GQGLEWIGEI NPSNGRTNYN QKFQGKATLT VDKSSSTAYM    300
QLSSLTSEDS AVYYFARGRP DYYGSSKWYF DVWGQGTTVT VSSASTKGPS VFPLAPSSKS    360
TSGGTAALGC LVKDYFPEPV TVSWNSGALT SGVHTFPAVL QSSGLYSLSS VVTVPSSSLG    420
TQTYICNVNH KPSNTKVDKK VEPKSCDKTH TCPPCPAPEL LGGPSVFLFP PKPKDTLMIS    480
RTPEVTCVVV DVSHEDPEVK FNWYVDGVEV HNAKTKPREE QYNSTYRVVS VLTVLHQDWL    540
NGKEYKCKVS NKALPAPIEK TISKAKGQPR EPQVYTLPPS RDELTKNQVS LTCLVKGFYP    600
SDIAVEWESN GQPENNYKTT PPVLDSDGSF FLYSKLTVDK SRWQQGNVFS CSVMHEALHN    660
HYTQKSLSLS PGK                                                      673

SEQ ID NO: 72              moltype = AA  length = 227
FEATURE                    Location/Qualifiers
REGION                     1..227
                           note = synthetic sequence
source                     1..227
                           mol_type = protein
                           organism = synthetic construct
SEQUENCE: 72
DIQMTQSPLS LSASVGDRVT ITCQASRDIR NYLNWYQQKP GKAPKLLIYD ASSLQTGVPS     60
RFGGSGSGTD FSFTIGSLQP EDIATYYCQQ FDSLPHTFGQ GTKLEIKEVQ LLESGGGLVQ    120
PGGSLRLSCA ASGFTFSIYR MQWVRQAPGK GLEWVSGISP SGGTTWYADS VKGRFTISRD    180
NSKNTLYLQM NSLRAEDTAV YYCARWSGGS GYAFDIWGQG TMVTVSS                  227

SEQ ID NO: 73              moltype = AA  length = 5
FEATURE                    Location/Qualifiers
REGION                     1..5
                           note = synthetic sequence
REGION                     1..5
                           note = MISC_FEATURE - n=1-5
source                     1..5
                           mol_type = protein
                           organism = synthetic construct
SEQUENCE: 73
GGGGS                                                                  5

SEQ ID NO: 74              moltype = AA  length = 5
FEATURE                    Location/Qualifiers
REGION                     1..5
                           note = synthetic sequence
REGION                     1..5
                           note = MISC_FEATURE - n=1-5
source                     1..5
                           mol_type = protein
                           organism = synthetic construct
SEQUENCE: 74
GGGGA                                                                  5

SEQ ID NO: 75              moltype = AA  length = 217
FEATURE                    Location/Qualifiers
REGION                     1..217
                           note = synthetic sequence
source                     1..217
                           mol_type = protein
                           organism = synthetic construct
SEQUENCE: 75
APELLGGPSV FLFPPKPKDT LMISRTPEVT CVVVDVSHED PEVKFNWYVD GVEVHNAKTK     60
PREEQYNSTY RVVSVLTVLH QDWLNGKEYK CKVSNKALPA PIEKTISKAK GQPREPQVYT    120
```

```
LPPSRDELTK NQVSLTCLVK GFYPSDIAVE WESNGQPENN YKTTPPVLDS DGSFFLYSKL    180
TVDKSRWQQG NVFSCSVMHE ALHNHYTQKS LSLSPGK                              217

SEQ ID NO: 76           moltype = AA  length = 217
FEATURE                 Location/Qualifiers
REGION                  1..217
                        note = synthetic sequence
source                  1..217
                        mol_type = protein
                        organism = synthetic construct
SEQUENCE: 76
APELLGGPSV FLFPPKPKDT LMISRTPEVT CVVVDVSHED PEVKFNWYVD GVEVHNAKTK     60
PREEQYNSTY RVVSVLTVLH QDWLNGKEYK CKVSNKALPA PIEKTISKAK GQPREPQVYT    120
LPPSREEMTK NQVSLTCLVK GFYPSDIAVE WESNGQPENN YKTTPPVLDS DGSFFLYSKL    180
TVDKSRWQQG NVFSCSVMHE ALHNHYTQKS LSLSPGK                              217

SEQ ID NO: 77           moltype = AA  length = 215
FEATURE                 Location/Qualifiers
REGION                  1..215
                        note = synthetic sequence
source                  1..215
                        mol_type = protein
                        organism = synthetic construct
SEQUENCE: 77
APPVAGPSVF LFPPKPKDTL MISRTPEVTC VVVDVSHEDP EVQFNWYVDG VEVHNAKTKP     60
REEQFNSTFR VVSVLTVVHQ DWLNGKEYKC KVSNKGLPAP IEKTISKTKG QPREPQVYTL    120
PPSREEMTKN QVSLTCLVKG FYPSDIAVEW ESNGQPENNY KTTPPMLDSD GSFFLYSKLT    180
VDKSRWQQGN VFSCSVMHEA LHNHYTQKSL SLSPG                                215

SEQ ID NO: 78           moltype = AA  length = 232
FEATURE                 Location/Qualifiers
REGION                  1..232
                        note = synthetic sequence
source                  1..232
                        mol_type = protein
                        organism = synthetic construct
SEQUENCE: 78
DIQMTQFPSS LSASVGDRVT ITCRASQGIR NDLGWYQQKP GKAPKRLIYA ASRLHRGVPS     60
RFSGSGSGTE FTLTISSLQP EDFATYYCLQ HNSYPSSFGQ GTKLEIKEVQ LLESGGGLVQ    120
PGGSLRLSCT ASGFTFSSYA MNWVRQAPGK GLEWVSAISG SGGTTFYADS VKGRFTISRD    180
NSRTTLYLQM NSLRAEDTAV YYCAKDLGWS DSYYYYGMD VWGQGTTVTV SS              232

SEQ ID NO: 79           moltype = AA  length = 107
FEATURE                 Location/Qualifiers
REGION                  1..107
                        note = synthetic sequence
source                  1..107
                        mol_type = protein
                        organism = synthetic construct
SEQUENCE: 79
DIQMTQFPSS LSASVGDRVT ITCRASQGIR NDLGWYQQKP GKAPKRLIYA ASRLHRGVPS     60
RFSGSGSGTE FTLTISSLQP EDFATYYCLQ HNSYPSSFGQ GTKLEIK                  107

SEQ ID NO: 80           moltype = AA  length = 125
FEATURE                 Location/Qualifiers
REGION                  1..125
                        note = synthetic sequence
source                  1..125
                        mol_type = protein
                        organism = synthetic construct
SEQUENCE: 80
EVQLLESGGG LVQPGGSLRL SCTASGFTFS SYAMNWVRQA PGKGLEWVSA ISGSGGTTFY     60
ADSVKGRFTI SRDNSRTTLY LQMNSLRAED TAVYYCAKDL GWSDSYYYY GMDVWGQGTT    120
VTVSS                                                                125

SEQ ID NO: 81           moltype = AA  length = 9
FEATURE                 Location/Qualifiers
REGION                  1..9
                        note = synthetic sequence
source                  1..9
                        mol_type = protein
                        organism = synthetic construct
SEQUENCE: 81
LQHNSYPSS                                                              9

SEQ ID NO: 82           moltype = AA  length = 665
FEATURE                 Location/Qualifiers
REGION                  1..665
                        note = synthetic sequence
```

```
                        source          1..665
                                        mol_type = protein
                                        organism = synthetic construct
SEQUENCE: 82
DIVMTQSPLS LPVTPGEPAS ISCRSSQSIV HSNGNTYLQW YLQKPGQSPQ LLIYKVSNRL    60
YGVPDRFSGS GSGTDFTLKI SRVEAEDVGV YYCFQGSHVP WTFGQGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGECQ VQLQESGPGL VKPSETLSLT   240
CTVSGYSITG GYLWNWIRQP PGKGLEWIGY ISYDGTNNYK PSLKDRVTIS RDTSKNQFSL   300
KLSSVTAADT AVYYCARYGR VFFDYWGQGT LVTVSSASTK GPSVFPLAPS SKSTSGGTAA   360
LGCLVKDYFP EPVTVSWNSG ALTSGVHTFP AVLQSSGLYS LSSVVTVPSS SLGTQTYICN   420
VNHKPSNTKV DKRVEPKSCD KTHTCPPCPA PELLGGPSVF LFPPKPKDTL YITREPEVTC   480
VVVDVSHEDP EVKFNWYVDG VEVHNAKTKP REEQYNSTYR VVSVLTVLHQ DWLNGKEYKC   540
KVSNKALPAP IEKTISKAKG QPREPQVYTL PPSREEMTKN QVSLTCLVKG FYPSDIAVEW   600
ESNGQPENNY KTTPPVLDSD GSFFLYSKLT VDKSRWQQGN VFSCSVMHEA LHNHYTQKSL   660
SLSPG                                                                665

SEQ ID NO: 83           moltype = AA   length = 446
FEATURE                 Location/Qualifiers
REGION                  1..446
                        note = synthetic sequence
source                  1..446
                        mol_type = protein
                        organism = synthetic construct
SEQUENCE: 83
QVQLQESGPG LVKPSETLSL TCTVSGYSIT GGYLWNWIRQ PPGKGLEWIG YISYDGTNNY    60
KPSLKDRVTI SRDTSKNQFS LKLSSVTAAD TAVYYCARYG RVFFDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGPSV   240
FLFPPKPKDT LYITREPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                         446

SEQ ID NO: 84           moltype = AA   length = 329
FEATURE                 Location/Qualifiers
REGION                  1..329
                        note = synthetic sequence
source                  1..329
                        mol_type = protein
                        organism = synthetic construct
SEQUENCE: 84
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                      329

SEQ ID NO: 85           moltype = AA   length = 673
FEATURE                 Location/Qualifiers
REGION                  1..673
                        note = synthetic sequence
source                  1..673
                        mol_type = protein
                        organism = synthetic construct
SEQUENCE: 85
DVVMTQTPLS LPVSLGDPAS ISCRSSQSIV HSNVNTYLEW YLQKPGQSPK LLIYKVSNRF    60
SGVPDRFSGS GAGTDFTLRI SRVEAEDLGI YYCFQGSHVP PTFGGGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGECQ VQLVQSGAEV KPGASVKLS    240
CKASGYTFTS YWMHWVKQRP GQGLEWIGEI NPSNGRTNYN QKFQGKATLT VDKSSSTAYM   300
QLSSLTSEDS AVYYFARGRP DYYGSSKWYF DVWGQGTTVT VSSASTKGPS VFPLAPSSKS   360
TSGGTAALGC LVKDYFPEPV TVSWNSGALT SGVHTFPAVL QSSGLYSLSS VVTVPSSSLG   420
TQTYICNVNH KPSNTKVDKK VEPKSCDKTH TCPPCPAPEL LGGPSVFLFP PKPKDTLMIS   480
RTPEVTCVVV DVSHEDPEVK FNWYVDGVEV HNAKTKPREE QYNSTYRVVS VLTVLHQDWL   540
NGKEYKCKVS NKALPAPIEK TISKAKGQPR EPQVYTLPPS RDELTKNQVS LTCLVKGFYP   600
SDIAVEWESN GQPENNYKTT PPVLDSDGSF FLYSKLTVDK SRWQQGNVFS CSVMHEALHN   660
HYTQKSLSLS PGK                                                       673

SEQ ID NO: 86           moltype = AA   length = 113
FEATURE                 Location/Qualifiers
REGION                  1..113
                        note = synthetic sequence
source                  1..113
                        mol_type = protein
                        organism = synthetic construct
SEQUENCE: 86
DVVMTQTPLS LPVSLGDPAS ISCRSSQSIV HSNVNTYLEW YLQKPGQSPK LLIYKVSNRF    60
```

```
SGVPDRFSGS GAGTDFTLRI SRVEAEDLGI YYCFQGSHVP PTFGGGTKLE IKR          113

SEQ ID NO: 87            moltype = AA   length = 330
FEATURE                  Location/Qualifiers
REGION                   1..330
                         note = synthetic sequence
source                   1..330
                         mol_type = protein
                         organism = synthetic construct
SEQUENCE: 87
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 88            moltype = AA   length = 329
FEATURE                  Location/Qualifiers
REGION                   1..329
                         note = synthetic sequence
source                   1..329
                         mol_type = protein
                         organism = synthetic construct
SEQUENCE: 88
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 89            moltype = AA   length = 329
FEATURE                  Location/Qualifiers
REGION                   1..329
                         note = synthetic sequence
source                   1..329
                         mol_type = protein
                         organism = synthetic construct
SEQUENCE: 89
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 90            moltype = AA   length = 330
FEATURE                  Location/Qualifiers
REGION                   1..330
                         note = synthetic sequence
source                   1..330
                         mol_type = protein
                         organism = synthetic construct
SEQUENCE: 90
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 91            moltype = AA   length = 124
FEATURE                  Location/Qualifiers
REGION                   1..124
                         note = synthetic sequence
source                   1..124
                         mol_type = protein
                         organism = synthetic construct
SEQUENCE: 91
QVQLVQSGAE VVKPGASVKL SSKASGYTFT SYWMHWVKQR PGQGLEWIGE INPSNGRTNY    60
NQKFQGKATL TVDKSSSTAY MQLSSLTSED SAVYYFARGR PDYYGSSKWY FDVWGQGTTV   120
TVSS                                                               124

SEQ ID NO: 92            moltype = AA   length = 454
FEATURE                  Location/Qualifiers
REGION                   1..454
                         note = synthetic sequence
source                   1..454
```

```
                        mol_type = protein
                        organism = synthetic construct
SEQUENCE: 92
QVQLVQSGAE VVKPGASVKL SCKASGYTFT SYWMHWVKQR PGQGLEWIGE INPSNGRTNY    60
NQKFQGKATL TVDKSSSTAY MQLSSLTSED SAVYYFARGR PDYYGSSKWY FDVWGQGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SRDELTKNQV SLTCLVKGFY PSDIAVEWES NGQPENNYKT TPPVLDSDGS FFLYSKLTVD   420
KSRWQQGNVF SCSVMHEALH NHYTQKSLSL SPGK                               454

SEQ ID NO: 93           moltype = AA   length = 219
FEATURE                 Location/Qualifiers
REGION                  1..219
                        note = synthetic sequence
source                  1..219
                        mol_type = protein
                        organism = synthetic construct
SEQUENCE: 93
DVVMTQTPLS LPVSLGDPAS ISCRSSQSIV HSNVNTYLEW YLQKPGQSPR LLIYKVSNRF    60
SGVPDRFSGS GAGTDFTLRI SRVEAEDLGI YYCFQGSHVP PTFGGGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 94           moltype = AA   length = 453
FEATURE                 Location/Qualifiers
REGION                  1..453
                        note = synthetic sequence
source                  1..453
                        mol_type = protein
                        organism = synthetic construct
SEQUENCE: 94
QVQLVQSGAE VVKPGASVKL SCKASGYTFT SYWMHWVKQR PGQGLEWIGE INPSNGRTNY    60
NQKFQGKATL TVDKSSSTAY MQLSSLTSED SAVYYFARGR PDYYGSSKWY FDVWGQGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
LLGGPSVFLF PPKPKDTLYI TREPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SRDELTKNQV SLTCLVKGFY PSDIAVEWES NGQPENNYKT TPPVLDSDGS FFLYSKLTVD   420
KSRWQQGNVF SCSVMHEALH NHYTQKSLSL SPG                                453

SEQ ID NO: 95           moltype = AA   length = 453
FEATURE                 Location/Qualifiers
REGION                  1..453
                        note = synthetic sequence
source                  1..453
                        mol_type = protein
                        organism = synthetic construct
SEQUENCE: 95
QVQLVQSGAE VVKPGASVKL SSKASGYTFT SYWMHWVKQR PGQGLEWIGE INPSNGRTNY    60
NQKFQGKATL TVDKSSSTAY MQLSSLTSED SAVYYFARGR PDYYGSSKWY FDVWGQGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
LLGGPSVFLF PPKPKDTLYI TREPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SRDELTKNQV SLTCLVKGFY PSDIAVEWES NGQPENNYKT TPPVLDSDGS FFLYSKLTVD   420
KSRWQQGNVF SCSVMHEALH NHYTQKSLSL SPG                                453

SEQ ID NO: 96           moltype = AA   length = 124
FEATURE                 Location/Qualifiers
REGION                  1..124
                        note = synthetic sequence
source                  1..124
                        mol_type = protein
                        organism = synthetic construct
SEQUENCE: 96
QVQLVQSGAE VVKPGASVKL SSKASGYTFT SYWMHWVKQR PGQGLEWIGE INPSNGRTNY    60
NQKFQGKATL TVDKSSSTAY MQLSSLTSED SAVYYFARGR PDYYGSSKWY FDVWGQGTTV   120
TVSS                                                                124

SEQ ID NO: 97           moltype = AA   length = 112
FEATURE                 Location/Qualifiers
REGION                  1..112
                        note = synthetic sequence
source                  1..112
                        mol_type = protein
                        organism = synthetic construct
SEQUENCE: 97
```

```
DVVMTQTPLS LPVSLGDPAS ISCRSSQSIV HSNVNTYLEW YLQKPGQSPR LLIYKVSNRF    60
SGVPDRFSGS GAGTDFTLRI SRVEAEDLGI YYCFQGSHVP PTFGGGTKLE IK          112

SEQ ID NO: 98           moltype = AA  length = 113
FEATURE                 Location/Qualifiers
REGION                  1..113
                        note = synthetic sequence
source                  1..113
                        mol_type = protein
                        organism = synthetic construct
SEQUENCE: 98
DIVMTQSPLS LPVTPGEPAS ISCRSSQSIV HSNGNTYLQW YLQKPGQSPQ LLIYKVSNRL    60
YGVPDRFSGS GSGTDFTLKI SRVEAEDVGV YYCFQGSHVP WTFGQGTKVE IKR          113

SEQ ID NO: 99           moltype = AA  length = 117
FEATURE                 Location/Qualifiers
REGION                  1..117
                        note = synthetic sequence
source                  1..117
                        mol_type = protein
                        organism = synthetic construct
SEQUENCE: 99
QVQLQESGPG LVKPSETLSL TCTVSGYSIT GGYLWNWIRQ PPGKGLEWIG YISYDGTNNY    60
KPSLKDRVTI SRDTSKNQFS LKLSSVTAAD TAVYYCARYG RVFFDYWGQG TLVTVSS      117
```

COMPOSITIONS AND METHODS FOR TREATMENT OF THYROID EYE DISEASE

CROSS REFERENCE TO RELATED APPLICATIONS

This application is a continuation of U.S. Non-Provisional application Ser. No. 17/822,978, filed Aug. 29, 2022, which is a continuation of U.S. Non-Provisional application Ser. No. 17/501,362, filed Oct. 14, 2021, which claims priority to U.S. Provisional Application No. 63/091,839, filed Oct. 14, 2020, U.S. Provisional Application No. 63/201,978, filed May 21, 2021, U.S. Provisional Application No. 63/260,130, filed Aug. 10, 2021, and U.S. Provisional Application No. 63/261,742, filed Sep. 28, 2021, each of which is hereby incorporated by reference in its entirety.

REFERENCE TO SEQUENCE LISTING SUBMITTED ELECTRONICALLY

The instant application contains a Sequence Listing which has been submitted electronically in XML file format and is hereby incorporated by reference in its entirety. Said XML copy, created on Jan. 5, 2023, is named "257635_000151_ST26.XML" and is 140,732 bytes in size.

BACKGROUND

Thyroid-associated ophthalmopathy (TAO), also known as thyroid eye disease (TED), Graves' ophthalmopathy or orbitopathy (GO), thyrotoxic exophthalmos, dysthyroid ophthalmopathy, and several other terms, is orbitopathy associated with thyroid dysfunction. TAO is divided into two types. Active TAO, which typically lasts 1-3 years, is characterized by an ongoing autoimmune/inflammatory response in the soft tissues of the orbit. Active TAO is responsible for the expansion and remodeling of the ocular soft tissues. The autoimmune/inflammatory response of active TAO spontaneously resolves and the condition transitions into inactive TAO. Inactive TAO is the term used to describe the long-term/permanent sequelae of active TAO. The cause of TAO is unknown. TAO is typically associated with Graves' hyperthyroidism, but can also occur as part of other autoimmune conditions that affect the thyroid gland and produce pathology in orbital and periorbital tissue, and, rarely, the pretibial skin (pretibial myxedema) or digits (thyroid acropachy). TAO is an autoimmune orbitopathy in which the orbital and periocular soft tissues are primarily affected with secondary effects on the eye and vision. In TAO, as a result of inflammation and expansion of orbital soft tissues, primarily eye muscles and adipose, the eyes are forced forward (bulge) out of their sockets—a phenomenon termed proptosis or exophthalmos. Although most cases of TAO do not result in loss of vision, this condition can cause vision-threatening exposure keratopathy, troublesome diplopia (double vision), and compressive dysthyroid optic neuropathy. TAO may precede, coincide with, or follow the systemic complications of dysthyroidism. The ocular manifestations of TAO include upper eyelid retraction, lid lag, swelling, redness (erythema), conjunctivitis, and bulging eyes (exophthalmos or proptosis), chemosis, periorbital edema, and altered ocular motility with significant functional, social, and cosmetic consequences. Many of the signs and symptoms of TAO, including proptosis and ocular congestion, result from expansion of the orbital adipose tissue and periocular muscles. The adipose tissue volume increases owing in part to new fat cell development (adipogenesis) within the orbital fat. The accumulation of hydrophilic glycosaminoglycans, primarily hyaluronic acid, within the orbital adipose tissue and the perimysial connective tissue between the extraocular muscle fibers, further expands the fat compartments and enlarges the extraocular muscle bodies. Hyaluronic acid is produced by fibroblasts residing within the orbital fat and extraocular muscles, and its synthesis in vitro is stimulated by several cytokines and growth factors, including IL-1beta, interferon-gamma, platelet-derived growth factor, thyroid stimulating hormone (TSH) and insulin-like growth factor I (IGF-I).

Antibodies that activate the insulin-like growth factor I receptor (IGF-IR) have also been detected and implicated in active TAO. Without being bound to any theory, it is believed that TSHR and IGF-IR form a physical and functional complex in orbital fibroblasts, and that blocking IGF-IR appears to attenuate both IGF-1 and TSH-dependent signaling. It has been suggested that blocking IGF-IR using an antibody antagonist might reduce both TSHR- and IGF-I-dependent signaling and therefore interrupt the pathological activities of autoantibodies acting as agonists on either receptor.

IGF-IR is a widely expressed heterotetrameric protein involved in the regulation of proliferation and metabolic function of many cell types. It is a tyrosine kinase receptor comprising two subunits. IGF-IRalpha contains a ligand-binding domain while IGF-IRbeta is involved in signaling and contains tyrosine phosphorylation sites.

Current therapies for hyperthyroidism due to Graves' disease are imperfect because therapies targeting the specific underlying pathogenic autoimmune mechanisms of the disease are lacking. Even more complex is the treatment of moderate-to-severe active TAO. Although recent years have witnessed a better understanding of its pathogenesis, TAO remains a therapeutic challenge and dilemma. There are no approved drugs to treat active TAO. Intravenous glucocorticoids (ivGCs) and oral glucocorticoids are used to treat patients with moderate-to-severe active TAO, but results are seldom satisfactory. Partial responses are frequent and relapses (rebound) after drug withdrawal are not uncommon. Adverse events do occur and many patients eventually require rehabilitative surgery conducted when their condition has transitioned to inactive TAO. Accordingly, there is still a need to provide alternative therapies for TAO and its related symptoms.

SUMMARY

The embodiments relate generally to IGF-1R antibodies, and antigen binding fragments thereof. Certain IGF-1R antibodies and antigen-binding fragments inhibit IGF-1R function or block the biological functions of IGF-I mediated IGF-1R signaling. Additionally, the invention generally relates to methods for treating thyroid-associated ophthalmopathy (TAO), also known as thyroid eye disease (TED), Graves' ophthalmopathy or orbitopathy (GO), thyrotoxic exophthalmos, dysthyroid ophthalmopathy, and other thyroid eye disorders associated with IGF-1R signaling.

In some embodiments, an antibody, or antigen binding fragment thereof, comprising a sequence as provided for herein is provided. In some embodiments, the antibody comprises a VL sequence as set forth in SEQ ID NO: 1, 3, 5, 7, 9, 11, 13, 15, 79, or 86; and a VH sequence as set forth in SEQ ID NO: 2, 4, 6, 8, 10, 12, 14, 16, 80, or 83. In some embodiments, the antibody comprises a LCDR sequence as set forth in SEQ ID NO: 17, 18, 19, 23, 24, 25, 29, 30, 31, 35, 36, 37, 41, 42, 43, 47, 48, 49, 53, 54, 55, 59, 60, 61, or 81, and a HCDR sequence as set forth in SEQ ID NO: 20, 21, 22, 26, 27, 28, 32, 33, 34, 38, 39, 40, 44, 45, 46, 50, 51, 52, 56, 57, 58, 62, 63, or 64; or any combination or variant thereof.

In some embodiments, the antibody, or antigen binding fragment thereof, comprises a $V_L$ peptide as set forth in SEQ ID NOs: 1, 3, 5, 7, 9, 11, 13, 15, 79, or 86, or any variant thereof. In some embodiments, the antibody, or antigen binding fragment thereof, comprises a $V_H$ peptide as set forth in SEQ ID NOs: 2, 4, 6, 8, 10, 12, 14, 16, 80, or 83, or any variant thereof.

In some embodiments, the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 20, 26, 32, 38, 44, 50, or 56; the heavy chain CDR2 has the amino acid sequence of SEQ ID NO: 21, 27, 33, 39, 45, 51, or 57; and the heavy chain CDR3 sequence has the amino acid sequence of SEQ ID NO: 22, 28, 34, 40, 46, 52, or 58; or variants of any of the foregoing; and (ii) a light chain variable region comprising light chain CDR1, CDR2, and CDR3 sequences, wherein the light chain CDR1 sequence has the amino acid sequence SEQ ID NO: 17, 23, 29, 35, 41, 47, or 53; the light chain CDR2 sequence has the amino acid sequence of SEQ ID NO: 18, 24, 30, 36, 42, 48, or 54; and the light chain CDR3 sequence has the amino acid sequence of SEQ ID NO: 19, 25, 31, 37, 43, 49, 55, or 81; or variants of any of the foregoing.

In some embodiments, the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 20; the heavy chain CDR2 has the amino acid sequence of SEQ ID NO: 21; and the heavy chain CDR3 sequence has the amino acid sequence of SEQ ID NO: 22; or variants of any of the foregoing; and (ii) a light chain variable region comprising light chain CDR1, CDR2, and CDR3 sequences, wherein the light chain CDR1 sequence has the amino acid sequence SEQ ID NO: 17; the light chain CDR2 sequence has the amino acid sequence of SEQ ID NO: 18; and the light chain CDR3 sequence has the amino acid sequence of SEQ ID NO: 19; or variants of any of the foregoing.

In some embodiments, the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 26; the heavy chain CDR2 has the amino acid sequence of SEQ ID NO: 27; and the heavy chain CDR3 sequence has the amino acid sequence of SEQ ID NO: 28; or variants of any of the foregoing; and (ii) a light chain variable region comprising light chain CDR1, CDR2, and CDR3 sequences, wherein the light chain CDR1 sequence has the amino acid sequence SEQ ID NO: 23; the light chain CDR2 sequence has the amino acid sequence of SEQ ID NO: 24; and the light chain CDR3 sequence has the amino acid sequence of SEQ ID NO: 25; or variants of any of the foregoing.

In some embodiments, the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 32; the heavy chain CDR2 has the amino acid sequence of SEQ ID NO: 33; and the heavy chain CDR3 sequence has the amino acid sequence of SEQ ID NO: 34; or variants of any of the foregoing; and (ii) a light chain variable region comprising light chain CDR1, CDR2, and CDR3 sequences, wherein the light chain CDR1 sequence has the amino acid sequence SEQ ID NO: 29; the light chain CDR2 sequence has the amino acid sequence of SEQ ID NO: 30; and the light chain CDR3 sequence has the amino acid sequence of SEQ ID NO: 31; or variants of any of the foregoing.

In some embodiments, the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 38; the heavy chain CDR2 has the amino acid sequence of SEQ ID NO: 39; and the heavy chain CDR3 sequence has the amino acid sequence of SEQ ID NO: 40; or variants of any of the foregoing; and (ii) a light chain variable region comprising light chain CDR1, CDR2, and CDR3 sequences, wherein the light chain CDR1 sequence has the amino acid sequence SEQ ID NO: 35; the light chain CDR2 sequence has the amino acid sequence of SEQ ID NO: 36; and the light chain CDR3 sequence has the amino acid sequence of SEQ ID NO: 37; or variants of any of the foregoing.

In some embodiments, the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 44; the heavy chain CDR2 has the amino acid sequence of SEQ ID NO: 45; and the heavy chain CDR3 sequence has the amino acid sequence of SEQ ID NO: 46; or variants of any of the foregoing; and (ii) a light chain variable region comprising light chain CDR1, CDR2, and CDR3 sequences, wherein the light chain CDR1 sequence has the amino acid sequence SEQ ID NO: 41; the light chain CDR2 sequence has the amino acid sequence of SEQ ID NO: 42; and the light chain CDR3 sequence has the amino acid sequence of SEQ ID NO: 43; or variants of any of the foregoing.

In some embodiments, the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 50; the heavy chain CDR2 has the amino acid sequence of SEQ ID NO: 51; and the heavy chain CDR3 sequence has the amino acid sequence of SEQ ID NO: 52; or variants of any of the foregoing; and (ii) a light chain variable region comprising light chain CDR1, CDR2, and CDR3 sequences, wherein the light chain CDR1 sequence has the amino acid sequence SEQ ID NO: 47; the light chain CDR2 sequence has the amino acid sequence of SEQ ID NO: 48; and the light chain CDR3 sequence has the amino acid sequence of SEQ ID NO: 49; or variants of any of the foregoing.

In some embodiments, the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 56; the heavy chain CDR2 has the amino acid sequence of SEQ ID NO: 57; and the heavy chain CDR3 sequence has the amino acid sequence of SEQ ID NO: 58; or variants of any of the foregoing; and (ii) a light chain variable region comprising light chain CDR1, CDR2, and CDR3 sequences, wherein the light chain CDR1 sequence has the amino acid sequence SEQ ID NO: 53; the light chain CDR2 sequence has the amino acid sequence of SEQ ID NO: 54; and the light chain CDR3 sequence has the amino acid sequence of SEQ ID NO: 55; or variants of any of the foregoing.

In some embodiments, the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 63; and the heavy chain CDR3 sequence has the amino acid sequence of SEQ ID NO: 64; or variants of any of the foregoing; and (ii) a light chain variable region comprising light chain CDR1, CDR2, and CDR3 sequences, wherein the light chain CDR1 sequence has the amino acid sequence SEQ ID NO: 59; the light chain CDR2 sequence has the amino acid sequence of SEQ ID NO: 60; and the light chain CDR3 sequence has the amino acid sequence of SEQ ID NO: 61; or variants of any of the foregoing.

In some embodiments, the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 38; the heavy chain CDR2 has the amino acid sequence of SEQ ID NO: 39; and the heavy chain CDR3 sequence has the amino acid sequence of SEQ ID NO: 40; or variants of any of the foregoing; and (ii) a light chain variable region comprising light chain CDR1, CDR2, and CDR3 sequences, wherein the light chain CDR1 sequence has the amino acid sequence SEQ ID NO: 35; the light chain CDR2 sequence has the amino acid sequence of SEQ ID NO: 36; and the light chain CDR3 sequence has the amino acid sequence of SEQ ID NO: 81; or variants of any foregoing.

In some embodiments, the antibody comprises a $V_L$ sequence as set forth in SEQ ID NO: 1, 3, 5, 7, 9, 11, 13, 15, 79, or 86, or a variant thereof. In some embodiments, the antibody comprises a $V_H$ sequence as set forth in SEQ ID NO: 2, 4, 6, 8, 10, 12, 14, 16, 80, or 83, or a variant thereof.

In some embodiments, the antibody comprises a sequence of SEQ ID NO: 65-72, 78, 82, or 85, or a variant thereof.

In some embodiments, the antibody comprises a light chain having the amino acid sequence of SEQ ID NO: 3 and a heavy chain comprising the amino acid sequence of SEQ ID NO: 83. In some embodiments, the antibody comprising a light chain variable region having the amino acid sequence of SEQ ID NO: 13 and a heavy chain variable region having the amino acid sequence of SEQ ID NO: 14.

In some embodiments, the antibody comprises a light chain having a an amino acid sequence of SEQ ID NO: 93 and a heavy chain amino acid sequence of SEQ ID NO: 92.

In some embodiments, the antibody comprises a light chain having a an amino acid sequence of SEQ ID NO: 93 and a heavy chain amino acid sequence of SEQ ID NO: 94.

In some embodiments, the antibody comprises a light chain having a an amino acid sequence of SEQ ID NO: 93 and a heavy chain amino acid sequence of SEQ ID NO: 95.

In some embodiments, the a variant of any antibodies provided herein are provided so long as the CDRs remain constant as compared to the parental (non-variant) sequence provided for herein.

In some embodiments, the antibody comprises a Fc region. In some embodiments, the Fc region is as set forth in SEQ ID NO: 75-77, 84, 87, 88, 89, or 90. In some embodiments, the Fc region is as set forth in SEQ ID NO: 75. In some embodiments, the Fc region is as set forth in SEQ ID NO: 76. In some embodiments, the Fc region is as set forth in SEQ ID NO: 77. In some embodiments, the Fc region is as set forth in SEQ ID NO: 84. In some embodiments, the Fc region is as set forth in SEQ ID NO: 87. In some embodiments, the Fc region is as set forth in SEQ ID NO: 88. In some embodiments, the Fc region is as set forth in SEQ ID NO: 89. In some embodiments, the Fc region is as set forth in SEQ ID NO: 90.

In some embodiments, pharmaceutical compositions comprising an antibody as provided for herein is provided.

In some embodiments, methods of treating or reducing the severity of, thyroid-associated ophthalmopathy (TAO), or a symptom thereof are provided, the methods comprising administering to a subject an antibody as provided for herein or a pharmaceutical composition comprising the same.

In some embodiments, methods of treating thyroid eye disease in a subject are provided, the methods comprising administering to a subject an antibody as provided for herein or a pharmaceutical composition comprising the same.

In some embodiments, methods of reducing Clinical Activity Score (CAS) of thyroid-associated ophthalmopathy (TAO) in a subject are provided, the methods comprising administering to a subject an antibody as provided for herein or a pharmaceutical composition comprising the same.

In some embodiments, methods of a) reducing proptosis by at least 2 mm and b) reducing the clinical activity score (CAS) in a subject with thyroid-associated ophthalmopathy (TAO) are provided, the methods comprising administering to a subject an antibody as provided for herein or a pharmaceutical composition comprising the same.

In some embodiments, methods of treating or reducing the severity of thyroid-associated ophthalmopathy (TAO) in a subject are provided, the methods comprising administering to a subject an antibody as provided for herein, or a pharmaceutical composition comprising the same, wherein treatment with said antibody (i) reduces proptosis by at least 2 mm in an eye; (ii) is not accompanied by a deterioration of 2 mm or more in the other (or fellow eye); and (iii) reduces the CAS in said subject to either one (1) or zero (0).

In some embodiments, methods of improving the quality of life in a subject with thyroid-associated ophthalmopathy (TAO, also called Graves' Ophthalmopathy/Graves' Orbitopathy) are provided, the methods comprising administering to a subject an antibody as provided for herein, or a pharmaceutical composition comprising the same.

In some embodiments, methods of treating or reducing the severity of diplopia in a subject with thyroid-associated ophthalmopathy (TAO) are provided, the methods comprising administering to a subject an antibody as provided for herein, or a pharmaceutical composition comprising the same.

In some embodiments, methods of increasing the internalization of IGF-1R on a cell are provided, the methods comprising contacting the cell with an antibody as provided for herein or a pharmaceutical composition comprising the same.

In some embodiments, methods of inhibiting IGF-1 stimulated receptor phosphorylation on a cell are provided, the methods comprising contacting the cell with an as provided for herein, or a pharmaceutical composition comprising the same.

In some embodiments, methods of treating thyroid eye disease in a subject are provided, the methods comprising administering an as provided for herein, or a pharmaceutical composition comprising the same to the subject, wherein the antibody has a serum concentration in the subject of at least, or about, 70 µg/ml, 75 µg/ml, 80 µg/ml, 85 µg/ml, 90 µg/ml, 95 µg/ml, 100 µg/ml, or 105 µg/ml at least 1, 2, or 3 week after administration.

In some embodiments, methods of inhibiting IGF-1 induced receptor autophosphorylation in a cell by at least 95%, 96%, 97%, 98%, or 99% or by 100% are provided, the method comprising contacting the cell with an antibody as provided for herein, or a pharmaceutical composition comprising the same.

In some embodiments, embodiments are provided for any of the methods provided for herein, wherein the antibody, or an antigen binding fragment thereof, is administered in a pharmaceutical composition that additionally comprises a pharmaceutically acceptable diluent or excipient or carrier. In some embodiments, the pharmaceutical composition further comprises one or more pharmaceutically active compounds for the treatment of TAO. In some embodiments, the pharmaceutical composition further comprises corticosteroids; rituximab or other anti-CD20 antibodies; tocilizumab or other anti-IL-6 antibodies; or selenium, infliximab or other anti-TNFalpha antibodies or a thyroid-stimulating hormone receptor (TSHR) inhibitor.

DETAILED DESCRIPTION

Figure 1:
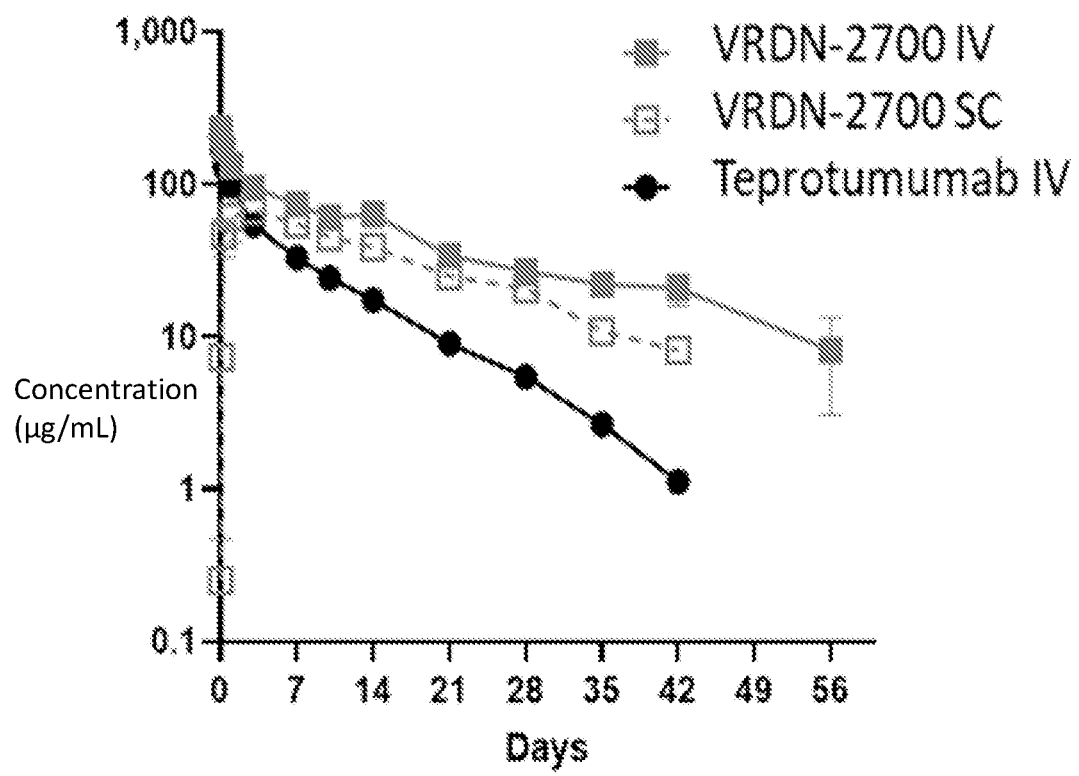
FIG. 1 illustrates the serum concentrations of VRDN-2700 and teprotumumab following either intravenous or subcutaneous administration, as indicated in the figure, are shown.

Provided herein are antibodies that bind and modulate the activity of IGF-1R. The antibodies can be used, for example, to treat thyroid eye disease.

As used herein, "Thyroid-associated Ophthalmopathy" (TAO), "Thyroid Eye Disease" (TED), "Graves' Ophthalmopathy" or "Graves' Orbitopathy" (GO) refer to the same disorder or condition and are used interchangeably. They all refer to the inflammatory orbital pathology associated with some autoimmune thyroid disorders, most commonly with "Graves' Disease" (GD), but sometimes with other diseases, e.g. Hashimoto's thyroiditis.

The terms "proptosis" and "exophthalmos" (also known as exophthalmos, exophthalmia, or exorbitism) refer to the forward projection, displacement, bulging, or protrusion of an organ. As used herein, the terms refer to the forward projection, displacement, bulging, or protrusion of the eye anteriorly out of the orbit. Proptosis and exophthalmos are considered by some of skill in the art to have the same meaning and are often used interchangeably, while others attribute subtle differences to their meanings. Exophthalmos is used by some to refer to severe proptosis; or to refer to endocrine-related proptosis. Yet others use the term exophthalmos when describing proptosis associated with the eye, in, for example, subjects with TAO (TED or GO).

As used herein, the terms "proptosis" and "exophthalmos" are used interchangeably and refer to the forward projection, displacement, bulging, or protrusion of the eye anteriorly out of the orbit. Owing to the rigid bony structure of the orbit with only anterior opening for expansion, any increase in orbital soft tissue contents taking place from the side or from behind will displace the eyeball forward. Proptosis or exophthalmos can be the result of a several disease processes including infections, inflammations, tumors, trauma, metastases, endocrine lesions, vascular diseases & extra orbital lesions. TAO (TED or GO) is currently recognized as the most common cause of proptosis in adults. Exophthalmos can be either bilateral, as is often seen in TAO (TED or GO), or unilateral (as is often seen in an orbital tumor).

Measurement of the degree of exophthalmos can be performed using, for example, an exophthalmometer, an instrument used for measuring the degree of forward displacement of the eye. The device allows measurement of the forward distance of the lateral orbital rim to the front of the cornea. Computed tomography (CT) scanning and Magnetic resonance imaging (MRI) may also be used in evaluating the degree of exophthalmos or proptosis. CT scanning is an excellent imaging modality for the diagnosis of TAO. In addition to allowing visualization of the enlarged extraocular muscles, CT scans provide the surgeon or clinician with depictions of the bony anatomy of the orbit when an orbital decompression is required. MRI, with its multi-planar and inherent contrast capabilities, provides excellent imaging of the orbital contents without the radiation exposure associated with CT scan studies. MRI provides better imaging of the optic nerve, orbital fat, and extraocular muscle, but CT scans provide better views of the bony architecture of the orbit. Orbital ultrasonography can also be a used for the diagnosis and evaluation of TAO, because it can be performed quickly and with a high degree of confidence. High reflectivity and enlargement of the extraocular muscles are assessed easily, and serial ultrasonographic examinations can also be used to assess progression or stability of the ophthalmopathy. Based on the technologies currently available, or that will become available in the future, one of skill in the art would be capable of determining the best modality for diagnosing and evaluating the extent of proptosis or exophthalmos.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic antibody.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')2, and Fv fragments; diabodies; linear antibodies; single-chain antibody molecules, e.g., sc-Fv; Nanobodies® (single-domain antibody) and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

In some embodiments, the antibodies, or antigen fragments herein, comprise a Fc region. In some embodiments, the Fc region comprises a mutation that extends the half-life of the antibody when linked to the Fc region. In some embodiments, the Fc region comprises a S228P, L235E, M252Y, S254T, T256E, M428L, N434S, L234F, P331S mutation, or any combination thereof. In some embodiments, the Fc region comprises a M252Y, S254T, and T256E mutations. A non-limiting example of a Fc region comprising the M252Y, S254T, and T256E mutations (collectively, "YTE Mutations") can be found in a sequence of SEQ ID NO: 89. In some embodiments, the Fc region comprising the YTE Mutations comprises a sequence of SEQ ID NO: 90, which differs from SEQ ID NO: 89 by the presence of a C-terminal lysine (K) residue. The numbering of the Fc region can be according to the Kabat numbering system for the Fc region.

In some embodiments, the Fc region comprises a S228P and a L235E mutation. In some embodiments, the antibody comprises a L234F, L235E, and P331S mutation. In some embodiments, the Fc region comprises M252Y, S254T, T256E, S228P and L235E mutations. In some embodiments, the Fc region comprises S228P, L235E, M428L, and N434S mutations. In some embodiments, the Fc region comprises the M428L and N434S mutations. In some embodiments, the Fc region comprises the L234F, L235E, P331S, M252Y, S254T, and T256E mutations. Mutations in the Fc region are also described in US2007041972A1, EP2235059B1, U.S. Pat. No. 8,394,925, and Mueller et al, Mol Immunol 1997 April; 34(6):441-52, each of which is incorporated by reference in its entirety. The numbering referenced herein refers to the Kabat numbering system for the Fc region.

In some embodiments, the Fc region comprises the sequence selected from:

```
                                                            (SEQ ID NO: 75)
APELLGGPSVFLFPPKPKDTLMISRTPEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYTQKSLSLSPGK;

(SEQ ID NO: 76)
APELLGGPSVFLFPPKPKDTLMISRTPEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALHNHYTQKSLSLSPGK;
or (SEQ ID NO: 77)
APPVAGPSVFLFPPKPKDTLMISRTPEVTCVVVDVSHEDPEVQFNWYVDGVEVHNAKTKPREEQFNSTFRVVSVLTV

VHQDWLNGKEYKCKVSNKGLPAPIEKTISKTKGQPREPQVYTLPPSREEMTKNQVSLTCLVKGFYPSDIAVEWESNG

QPENNYKTTPPMLDSDGSFFLYSKLTVDKSRWQQGNVFSCSVMHEALHNHYTQKSLSLSPG;
or (SEQ ID NO: 84)
ASTKGPSVFPLAPSSKSTSGGTAALGCLVKDYFPEPVTVSWNSGALTSGVHTFPAVLQSSGLYSLSSVVTVPSSSLG

TQTYICNVNHKPSNTKVDKRVEPKSCDKTHTCPPCPAPELLGGPSVFLFPPKPKDTLYITREPEVTCVVVDVSHEDP

EVKFNWYVDGVEVHNAKTKPREEQYNSTYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVLDSDGSFFLYSKLTVDKSRWQQGNVFSC

SVMHEALHNHYTQKSLSLSPG (SEQ ID NO: 87)
ASTKGPSVFPLAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVLDSDGSFFLYSKLTVDKSRWQQGNVFSC

SVMHEALHNHYTQKSLSLSPGK
```

-continued (SEQ ID NO: 88)
ASTKGPSVFPLAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVLDSDGSFFLYSKLTVDKSRWQQGNVFSC

SVMHEALHNHYTQKSLSLSPG (SEQ ID NO: 89)
ASTKGPSVFPLAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFPPKPKDTLYITREPEVTCVVVDVSHEDP

EVKFNWYVDGVEVHNAKTKPREEQYNSTYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVLDSDGSFFLYSKLTVDKSRWQQGNVFSC

SVMHEALHNHYTQKSLSLSPG (SEQ ID NO: 90)
ASTKGPSVFPLAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFPPKPKDTLYITREPEVTCVVVDVSHEDP

EVKFNWYVDGVEVHNAKTKPREEQYNSTYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVLDSDGSFFLYSKLTVDKSRWQQGNVFSC

SVMHEALHNHYTQKSLSLSPGK

A "Fab' fragment" contains one light chain and a portion or fragment of one heavy chain that contains the $V_H$ domain and the CH1 domain and also the region between the $C_H1$ and $C_H2$ domains, such that an interchain disulfide bond can be formed between the two heavy chains of two Fab' fragments to form a F(ab') 2 molecule.

A "F(ab')2 fragment" contains two light chains and two heavy chains containing a portion of the constant region between the $C_H1$ and $C_H^2$ domains, such that an interchain disulfide bond is formed between the two heavy chains. A F(ab') 2 fragment thus is composed of two Fab' fragments that are held together by a disulfide bond between the two heavy chains.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

In certain embodiments, monoclonal antibodies herein also include camelized single domain antibodies. See, e.g., Muyldermans et al. (2001) Trends Biochem. Sci. 26:230; Reichmann et al. (1999) J. Immunol. Methods 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

Typically, a variant antibody or antigen binding fragment of the antibodies provided herein retain at least 10% of its IGF-1R binding activity (when compared to a parental antibody that is modified) when that activity is expressed on a molar basis. In some embodiments, a variant antibody (or antigen fragment thereof), or antigen binding fragment of an antibody provided herein, retains at least 20%, 50%, 70%, 80%, 90%, 95% or 100% or more of the IGF-1R binding affinity as the parental antibody. As described herein, it is also intended that an antibody or antigen binding fragment of the invention can include conservative or non-conservative amino acid substitutions, which can also be referred to as "conservative variants" or "function conserved variants" of the antibody, that do not substantially alter its biologic activity.

"Isolated antibody" refers to the purification status of a binding compound and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

The term "monoclonal antibody", as used herein, refers to population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

As used herein, a "chimeric antibody" is an antibody having the variable domain from a first antibody and constant domain from a second antibody, where the first and second antibodies are from different species. (U.S. Pat. No. 4,816,567; and Morrison et al., (1984) *Proc. Natl. Acad. Sci. USA* 81: 6851-6855). Typically the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g. rodent) antibody.

As used herein, the term "humanized antibody" refers to forms of antibodies that contain sequences from both human and non-human (e.g., murine, rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (CDRL1), 50-52 (CDRL2) and 91-96 (CDRL3) in the light chain variable domain and 26-32 (CDRH1), 53-55 (CDRH2) and 96-101 (CDRH3) in the heavy chain variable domain; Chothia and Lesk (1987) *J. Mol. Biol.* 196: 901-917). As used herein, the term "framework" or "FR" residues refers to those variable domain residues other than the hypervariable region residues defined herein as CDR residues. CDRs provide the majority of contact residues for the binding of the antibody to the antigen or epitope. CDRs of interest can be derived from donor antibody variable heavy and light chain sequences, and include analogs of the naturally occurring CDRs, which analogs also share or retain the same antigen binding specificity and/or neutralizing ability as the donor antibody from which they were derived.

Additionally, in some embodiments, the antibodies can take the form of a full length antibody, single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody®; a Transbody; an Anticalin; an AdNectin; an Affilin®; a Microbody; a peptide aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody®; Affimers, a DuoBody®, a Fv, a Fab, a Fab', a F(ab')2, a peptide mimetic molecule, or a synthetic molecule, as described in U.S. Pat. Nos. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004, 746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of each of which are hereby incorporated by reference in their entireties. See also, Storz MAbs. 2011 May-June; 3(3): 310-317, which is hereby incorporated by reference.

The term "antigen" as used herein means any molecule that has the ability to generate antibodies either directly or indirectly or that binds to antibody. Included within the definition of "antigen" is a protein-encoding nucleic acid. An "antigen" can also refer to the binding partner of an antibody. In some embodiments, the antigen is the IGF-1R protein expressed on the surface of a cell. In some embodiments, the cell is an intact cell. An intact cell is a cell that has not been lysed or broken open with the use of detergents or other reagents. A cell that has been treated with detergents or other reagents that breaks up the cellular membrane or punches holes in a cellular membrane is not an intact cell. For example, methods are provided herein for generating an antibody that binds to a IGF-1R protein, the method comprising culturing a cell comprising a nucleic acid molecule encoding the IGF-1R antibody.

As used herein, "specific binding" or "immunospecific binding" or "binds immunospecifically" refer to antibody binding to a predetermined antigen (e.g. IGF-1R) or epitope present on the antigen. In some embodiments, the antibody binds with a dissociation constant ($K_D$) of $10^{-7}$ M or less, and binds to the predetermined antigen with a $K_D$ that is at least two-fold less than its $K_D$ for binding to a non-specific antigen (e.g., BSA, casein, or another non-specific polypeptide) other than the predetermined antigen. The phrases "an antibody recognizing IGF-1R" and "an antibody specific for IGF-1R" are used interchangeably herein with the term "an antibody which binds immunospecifically to IGF-1R." Reference in the present disclosure may be made to IGF-1R. The degree of specificity necessary for an anti-IGF-1R antibody may depend on the intended use of the antibody, and at any rate is defined by its suitability for use for an intended purpose. In some embodiments, the antibody, or binding compound derived from the antigen-binding site of an antibody, of the contemplated method binds to its antigen (IGF-1R), with an affinity that is at least two fold greater, at least ten times greater, at least 20-times greater, or at least 100-times greater than the affinity with any other antigen.

Methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589 601 (1983), which references are entirely incorporated herein by reference.

The term "homolog" means protein sequences having between 40% and 100% sequence homology or identity to a reference sequence. Percent identity between two peptide chains can be determined by pair wise alignment using the default settings of the AlignX module of Vector NTI v.9.0.0 (Invitrogen Corp., Carlsbad, Calif.). In some embodiments, the antibody, or antigenic binding fragment thereof has, at least 50, 60, 70, 80, 90, 91, 92, 93, 94, 95, 96, 97, 98, or 99% homology or identity to a sequence described herein. In some embodiments, the antibody has conservative substitutions as compared to a sequence described herein. Exemplary conservative substitutions are illustrated in Table 1 and are encompassed within the scope of the disclosed subject matter. The conservative substitution may reside in the framework regions, or in antigen-binding sites, as long they do not adversely affect the properties of the antibody. Substitutions may be made to improve antibody properties, for example stability or affinity. Conservative substitutions will produce molecules having functional and chemical characteristics similar to those molecules into which such modifications are made. Exemplary amino acid substitutions are shown in the table below.

TABLE

Exemplary Conservative Substitutions:

| Original Residue | Exemplary Conservative Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Gly | Pro, Ala |
| His | Asn, Gln, Lys, Arg |
| Ile | Leu, Val, Met, Ala, Phe |
| Leu | Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

In some embodiments, variants of the proteins and peptides provided herein are provided. In some embodiments, a variant comprises a substitution, deletions, or insertion. In some embodiments, the variant comprises 1, 2, 3, 4, 5, 6, 7, 8, 9, or 10 (e.g., 1-10) substitutions. As described herein, the substitutions can be conservative substitutions. In some embodiments, the substitution is non-conservative. In some embodiments, the variant comprises 1, 2, 3, 4, 5, 6, 7, 8, 9, or 10 (e.g., 1-10) deletions. In some embodiments, the variant comprises 1, 2, 3, 4, 5, 6, 7, 8, 9, or 10 (e.g., 1-10) insertions. In some embodiments, the substitutions, deletions, or insertions are present in the CDRs provided for herein. In some embodiments, the substitutions, deletions, or insertions are not present in the CDRs provided for herein.

The term "in combination with" as used herein means that the described agents can be administered to an animal or subject together in a mixture, concurrently as single agents or sequentially as single agents in any order.

The techniques to raise antibodies to small peptide sequences that recognize and bind to those sequences in the free or conjugated form or when presented as a native sequence in the context of a large protein are well known in the art. Such antibodies include murine, murine-human and human-human antibodies produced by hybridoma or recombinant techniques known in the art. Antibodies can also be produced in human, a mouse, sheep, a rat, a rabbit, a shark, a llama, or a chicken. In some embodiments, the antibody is produced in a chicken. The antibodies can also be produced in or other small animals.

The term "epitope" is meant to refer to that portion of any molecule capable of being recognized by and bound by an antibody at one or more of the Ab's antigen binding regions. Epitopes usually consist of chemically active surface groupings of molecules such as amino acids or sugar side chains and have specific three dimensional structural characteristics as well as specific charge characteristics. Example of epitopes include, but are not limited to, the residues described herein that form IGF-1R epitopes. In some embodiments, the epitope is only present in a non-denatured protein. In some embodiments, the epitope is only present in a denatured protein.

In some embodiments, the source for the DNA encoding a non-human antibody include cell lines which produce antibody, such as hybrid cell lines commonly known as hybridomas.

The hybrid cells are formed by the fusion of a non-human antibody-producing cell, typically a spleen cell of an animal immunized against either natural or recombinant antigen, or a peptide fragment of the antigen protein sequence. Alternatively, the non-human antibody-producing cell can be a B lymphocyte obtained from the blood, spleen, lymph nodes or other tissue of an animal immunized with the antigen.

The second fusion partner, which provides the immortalizing function, can be a lymphoblastoid cell or a plasmacytoma or myeloma cell, which is not itself an antibody producing cell, but is malignant. Fusion partner cells include, but are not limited to, the hybridoma SP2/0-Ag14, abbreviated as SP2/0 (ATCC® CRL1581) and the myeloma P3X63Ag8 (ATCC® TIB9), or its derivatives. See, e.g., Ausubel infra, Harlow infra, and Colligan infra, the contents of which references are incorporated entirely herein by reference.

The antibodies can be generated according the examples provided herein. Once the sequences are known, the antibodies can also be generated according to known methods. The antibodies can also be converted to different types, such as being converted to Human IgGs and the like. By converting the antibodies to a human antibody, a human subject should not identify the antibodies as foreign. The conversion of a non-human IgG antibody to a human IgG antibody is well known and can routinely be done once the native sequence is known. As discussed herein, the antibodies can be modified according to known methods. Such methods are described in, for example, Riechmann L, Clark M, Waldmann H, Winter G (1988). Reshaping human antibodies for therapy". *Nature* 332 (6162): 332-323; Tsurushita N, Park M, Pakabunto K, Ong K, Avdalovic A, Fu H, Jia A, Vásquez M, Kumar S. (2004). The antibody-producing cell contributing the nucleotide sequences encoding the antigen-binding region of the chimeric antibody can also be produced by transformation of a non-human, such as a primate, or a human cell. For example, a B lymphocyte which produces the antibody can be infected and transformed with a virus such as Epstein-Barr virus to yield an immortal antibody producing cell (Kozbor et al., Immunol. Today 4:72 79 (1983)). Alternatively, the B lymphocyte can be transformed by providing a transforming gene or transforming gene product, as is well-known in the art. See, e.g., Ausubel infra, Harlow infra, and Colligan infra, the contents of which references are incorporated entirely herein by reference. The cell fusions are accomplished by standard procedures well known to those skilled in the field of immunology. Fusion partner cell lines and methods for fusing and selecting hybridomas and screening for mAbs are well known in the art. See, e.g., Ausubel infra, Harlow infra, and Colligan infra, the contents of which references are incorporated entirely herein by reference.

In some embodiments, the antibody is a MAb which binds to IGF-1R. In some embodiments, the antibody binds to amino acids of an epitope of the IGF-1R.

In some embodiments, the antibody comprises a sequence as provided for herein.

The sequences of the antibodies can be modified to yield human IgG antibodies. The conversion of the sequences provided herein can be modified to yield other types of antibodies. The CDRs can also be linked to other antibodies, proteins, or molecules to create antibody fragments that bind to IGF-1R. This can be in the form of an antibody drug conjugate ("ADC"), a multi-specific molecule, or a chimeric antigen receptor. The CDRs and antibody sequences provided herein also be humanized or made fully human according to known methods. The sequences can also be made into chimeric antibodies as described herein.

In some embodiments, the antibody comprises an amino acid sequence comprising a sequence provided for herein or a fragment thereof. In some embodiments, the antibody comprises one or more amino acid sequences as provided herein, an antigen binding fragments, thereof, or a human IgG variant thereof. "A human IgG variant thereof" refers to an antibody that has been modified to be a human IgG when the starting antibody is not a human IgG antibody.

As described herein the production of antibodies with a known sequence is routine and can be done by any method. Accordingly, in some embodiments, a nucleic acid encoding an antibody or fragment thereof is provided. In some embodiments, the nucleic acid encodes a sequence provided for herein. The antibodies can also be modified to be chimeric antibodies or human antibodies. The antibodies can also be used in injectable pharmaceutical compositions. As also described herein, the antibodies can be isolated antibodies or engineered antibodies.

In some embodiments, "derivatives" of the antibodies, fragments, regions or derivatives thereof, which term includes those proteins encoded by truncated or modified genes to yield molecular species functionally resembling the immunoglobulin fragments are provided. The modifications include, but are not limited to, addition of genetic sequences coding for cytotoxic proteins such as plant and bacterial toxins. The modification can also include a reporter protein, such as a fluorescent or chemiluminescent tag. The fragments and derivatives can be produced in any manner.

The identification of these antigen binding region and/or epitopes recognized by Abs described herein provide the information necessary to generate additional monoclonal antibodies with similar binding characteristics and therapeutic or diagnostic utility that parallel the embodiments of this application.

The nucleic acid sequence encoding an antibody described herein can be genomic DNA or cDNA, or RNA (e.g. mRNA) which encodes at least one of the variable regions described herein. A convenient alternative to the use of chromosomal gene fragments as the source of DNA encoding the V region antigen-binding segment is the use of cDNA for the construction of chimeric immunoglobulin genes, e.g., as reported by Liu et al. (Proc. Natl. Acad. Sci., USA 84:3439 (1987) and J. Immunology 139:3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

For example, a cDNA encoding a V region antigen-binding segment able to detect, bind, to or neutralize a IGF-1R antigen can be provided using known methods based on the use of the amino acid sequences provided herein. Because the genetic code is degenerate, more than one codon can be used to encode a particular amino acid (Watson, et al., infra). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an antibody or fragment. Such "codon usage rules" are disclosed by Lathe, et al., J. Molec. Biol. 183:1 12 (1985). Using the "codon usage rules" of Lathe, a single oligonucleotide, or a set of oligonucleotides, that contains a theoretical "most probable" nucleotide sequence capable of encoding an antibody variable or constant region sequences is identified.

The variable regions described herein can be combined with any type of constant region including a human constant region or murine constant region. Human genes which encode the constant (C) regions of the antibodies, fragments and regions can be derived from a human fetal liver library, by known methods. Human C regions genes can be derived from any human cell including those which express and produce human immunoglobulins. The human $C_H$ region can be derived from any of the known classes or isotypes of human H chains, including gamma, $\mu$, $\alpha$, $\delta$ or $\epsilon$, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1), gamma 3 (IgG3), gamma 4 (IgG4), or $\mu$ (IgM). The human $C_L$ region can be derived from either human L chain isotype, kappa or lambda. In some embodiments, the antibody comprises a Fc domain. In some embodiments, the Fc domain comprises a mutation to extend the half-life of the antibody. In some embodiments, the Fc domain comprises a mutation such as those described in U.S. Pat. No. 7,670,600, which is hereby incorporated by reference in its entirety. In some embodiment, the constant region comprises a mutation at position at amino acid residue 428 relative to a wild-type human IgG constant domain, numbered according to the EU numbering index of Kabat. Without being bound to any particular theory, an antibody comprising a mutation that corresponds to residue 428 can have an increased half-life compared to the half-life of an IgG having the wild-type human IgG constant domain. In some embodiments, the mutation is a substitution of the native residue with a threonine, leucine, phenylalanine or serine. In some embodiments, the antibody further comprises one or more amino acid substitutions relative to the corresponding wild-type human IgG constant domain at one or more of amino acid residues 251-256, 285-290, 308-314, 385-389, and 429-436, numbered according to the Kabat EU numbering index. The specific mutations or substitutions at these positions are described in U.S. Pat. No. 7,670,600, which is hereby incorporated by reference in its entirety.

Genes encoding human immunoglobulin C regions can be obtained from human cells by standard cloning techniques (Sambrook, et al. (Molecular Cloning: A Laboratory Manual, 2nd Edition, Cold Spring Harbor Press, Cold Spring Harbor, N.Y. (1989) and Ausubel et al., eds. Current Protocols in Molecular Biology (1987 1993)). Human C region genes are readily available from known clones containing genes representing the two classes of L chains, the five classes of H chains and subclasses thereof. Chimeric antibody fragments, such as F(ab')2 and Fab, can be prepared by designing a chimeric H chain gene which is appropriately truncated. For example, a chimeric gene encoding an H chain portion of an F(ab')2 fragment would include DNA sequences encoding the $CH_1$ domain and hinge region of the H chain, followed by a translational stop codon to yield the truncated molecule.

In some embodiments, the antibodies, murine, human, humanized, or chimeric antibodies, fragments and regions of the antibodies described herein are produced by cloning DNA segments encoding the H and L chain antigen-binding regions of a IGF-1R antigen specific antibody, and joining these DNA segments to DNA segments encoding $C_H$ and $C_L$ regions, respectively, to produce murine, human or chimeric immunoglobulin-encoding genes.

Thus, in some embodiments, a fused chimeric gene is created which comprises a first DNA segment that encodes at least the antigen-binding region of non-human origin, such as a functionally rearranged V region with joining (J) segment, linked to a second DNA segment encoding at least a part of a human C region.

Therefore, cDNA encoding the antibody V and C regions, the method of producing the antibody according to some of the embodiments described herein involve several steps, as exemplified below: 1. isolation of messenger RNA (mRNA) from the cell line producing an anti-IGF-1R antigen antibody and from optional additional antibodies supplying heavy and light constant regions; cloning and cDNA production therefrom; 2. preparation of a full length cDNA library from purified mRNA from which the appropriate V and/or C region gene segments of the L and H chain genes can be: (i) identified with appropriate probes, (ii) sequenced, and (iii) made compatible with a C or V gene segment from another antibody for a chimeric antibody; 3. Construction of complete H or L chain coding sequences by linkage of the cloned specific V region gene segments to cloned C region gene, as described above; 4. Expression and production of L and H chains in selected hosts, including prokaryotic and eukaryotic cells to provide murine-murine, human-murine, human-human or human murine antibodies.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

As used herein and unless otherwise indicated, the term "about" is intended to mean±5% of the value it modifies. Thus, about 100 means 95 to 105.

In some embodiments, the antibodies described herein are used to detect the presence of the antigen. The present antibody can be used in any device or method to detect the presence of the antigen.

The term "purified" with referenced to an antibody refers to an antibody that is substantially free of other material that associates with the molecule in its natural environment. For instance, a purified protein is substantially free of the cellular material or other proteins from the cell or tissue from which it is derived. The term refers to preparations where the isolated protein is sufficiently pure to be analyzed, or at least 70% to 80% (w/w) pure, at least 80%-90% (w/w) pure, 90-95% pure; and, at least 95%, 96%, 97%, 98%, 99%, or 100% (w/w) pure. In some embodiments, the antibody is purified.

As an alternative to preparing monoclonal antibody-secreting hybridomas, a monoclonal antibody to a polypeptide may be identified and isolated by screening a recombinant combinatorial immunoglobulin library (e.g., an antibody phage display library) with a polypeptide described herein to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody or antigen binding protein display libraries can be found in the literature. Thus, the epitopes described herein can be used to screen for other antibodies that can be used therapeutically, diagnostically, or as research tools.

Antibody Conjugates

The antibodies provided for herein may also be conjugated to a chemical moiety. The chemical moiety may be, inter alia, a polymer, a radionuclide or a cytotoxic factor. In some embodiments, this can be referred to as an antibody drug conjugate. In some embodiments, the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)). Examples of chemical moieties include, but are not limited to, anti-mitotics, such as calicheamicins (e.g. ozogamicin), monomethyl auristatin E, mertansine, and the like. Other exmaples include, but are not limited to, biologically active anti-microtubule agents, alkylating agents and DNA minor groove binding agents. Other examples of are provided herein and below. The chemical moiety can be linked to the antibody through a linking group (maleimide), a cleaveble linker, such as a cathepsin cleavable linkers (valine-citrulline), and in some embodiments, one or more spacers (e.g. para-aminobenzyl-carbamate). Without being bound to any particular theory, once the antibody conjugate binds IGF-1R it can be internalized and the chemical moiety can kill the cell or otherwise inhibit its growth. In some embodiments, the cell is a thyroid cell.

The antibodies and antibody fragments of the invention may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr and $^{56}$Fe.

The antibodies and antibody fragments may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody molecules may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the antibody molecules of the invention to the various moieties may be employed, including those methods described by Hunter, et al., (1962) *Nature* 144:945; David, et al., (1974) *Biochemistry* 13:1014; Pain, et al., (1981) *J. Immunol. Meth.* 40:219; and Nygren, J., (1982) *Histochem. and Cytochem.* 30:407. Methods for conjugating antibodies are conventional and very well known in the art.

Chimeric Antigen Receptors

The antibodies provided herein can also be incorporated into a chimeric antigen receptor ("CAR") that can be used, for example, in a CAR-T cell. In some embodiments, the extracellular domain of the CAR can be an antibody as provided for herein. In some embodiments, the antibody is in a scFv format. CAR-T cells are a type of treatment in which a patient's T cells are modified so they will attack the cells that are expressing IGF-1R. T cells are taken from a patient's blood. Then the gene for a special receptor that binds to a certain protein on the patient's cells is added in the laboratory. In some embodiments, the receptor binds to IGF-1R using the binding regions of the antibodies provided for herein. The CAR-T cells comprising the IGF-1R antibody can then be used to treat a condition, such as those provided for herein.

In some embodiments, antibodies (e.g. an anti-IGF-1R antibody) are provided herein. In some embodiments, the antibody is a recombinant antibody that binds to a IGF-1R protein. In some embodiments, the IGF-1R protein is a human IGF-1R protein. In some embodiments, the IGF-1R protein that is recognized by the antibodies is in its native conformation (non-denatured) conformation. In some embodiments, the antibody does not specifically binds to a denatured IGF-1R protein. As used herein, the term "recombinant antibody" refers to an antibody that is not naturally occurring. In some embodiments, the term "recombinant antibody" refers to an antibody that is not isolated from a human subject.

In some embodiments, the antibody comprises one or more peptides having the following sequences, or a variant thereof:

| AB ID NO. | AB Sequence LC and HC | LC Sequence | HC Sequence |
| --- | --- | --- | --- |
| VRDN-03100 | EIVLTQSPATLSLSPGERATLSC RASQSVSSYLAWYQQKPGQAPRL LIYDASKRATGIPARFSGSGSGT DFTLTISSLEPEDFAVYYCQQRS KWPPWTFGQGTKVESKRTVAAPS VFIFPPSDEQLKSGTASVVCLLN NFYPREAKVQWKVDNALQSGNSQ ESVTEQDSKDSTYSLSSTLTLSK ADYEKHKVYACEVTHQGLSSPVT KSFNRGEC QVELVESGGGVVQPGRSQRLSCA ASGFTFSSYGMHWVRQAPGKGLE WVAIIWFDGSSTYYADSVRGRFT ISRDNSKNTLYLQMNSLRAEDTA VYFCARELGRRYFDLWGRGTLVS VSSASTKGPSVFPLAPSSKSTSG GTAALGCLVKDYFPEPVTVSWNS GALTSGVHTFPAVLQSSGLYSLS SVVTVPSSSLGTQTYICNVNHKP SNTKVDKKVEPKSCDKTHTCPPC PAPELLGGPSVFLFPPKPKDTLM ISRTPEVTCVVVDVSHEDPEVKF NWYVDGVEVHNAKTKPREEQYNS TYRVVSVLTVLHQDWLNGKEYKC KVSNKALPAPIEKTISKAKGQPR EPQVYTLPPSRDELTKNQVSLTC LVKGFYPSDIAVEWESNGQPENN YKTTPPVLDSDGSFFLYSKLTVD KSRWQQGNVFSCSVMHEALHNHY TQKSLSLSPGK (SEQ ID NO: 65) | EIVLTQSPATLSLSP GERATLSCRASQSVS SYLAWYQQKPGQAPR LLIYDASKRATGIPA RFSGSGSGTDFTLTI SSLEPEDFAVYYCQQ RSKWPPWTFGQGTKV ESKRTVAAPSVFIFP PSDEQLKSGTASVVC LLNNFYPREAKVQWK VDNALQSGNSQESVT EQDSKDSTYSLSSTL TLSKADYEKHKVYAC EVTHQGLSSPVTKSF NRGEC (SEQ ID NO: 1) | QVELVESGGGVVQPGRSQRLSC AASGFTFSSYGMHWVRQAPGKG LEWVAIIWFDGSSTYYADSVRG RFTISRDNSKNTLYLQMNSLRA EDTAVYFCARELGRRYFDLWGR GTLVSVSSASTKGPSVFPLAPS SKSTSGGTAALGCLVKDYFPEP VTVSWNSGALTSGVHTFPAVLQ SSGLYSLSSVVTVPSSSLGTQT YICNVNHKPSNTKVDKKVEPKS CDKTHTCPPCPAPELLGGPSVF LFPPKPKDTLMISRTPEVTCVV VDVSHEDPEVKFNWYVDGVEVH NAKTKPREEQYNSTYRVVSVLT VLHQDWLNGKEYKCKVSNKALP APIEKTISKAKGQPREPQVYTL PPSRDELTKNQVSLTCLVKGFY PSDIAVEWESNGQPENNYKTTP PVLDSDGSFFLYSKLTVDKSRW QQGNVFSCSVMHEALHNHYTQK SLSLSPGK (SEQ ID NO: 2) |
| VRDN-02100 | DIVMTQSPLSLPVTPGEPASISC RSSQSIVHSNGNTYLQWYLQKPG QSPQLLIYKVSNRLYGVPDRFSG SGSGTDFTLKISRVEAEDVGVYY CFQGSHVPWTFGQGTKVEIKRTV AAPSVFIFPPSDEQLKSGTASVV CLLNNFYPREAKVQWKVDNALQS GNSQESVTEQDSKDSTYSLSSTL TLSKADYEKHKVYACEVTHQGLS SPVTKSFNRGEC QVQLQESGPGLVKPSETLSLTCT VSGYSITGGYLWNWIRQPPGKGL EWIGYISYDGTNNYKPSLKDRVT ISRDTSKNQFSLKLSSVTAADTA VYYCARYGRVFFDYWGQGTLVTV SSASTKGPSVFPLAPSSKSTSGG TAALGCLVKDYFPEPVTVSWNSG ALTSGVHTFPAVLQSSGLYSLSS VVTVPSSSLGTQTYICNVNHKPS NTKVDKRVEPKSCDKTHTCPPCP APELLGGPSVFLFPPKPKDTLMI SRTPEVTCVVVDVSHEDPEVKFN WYVDGVEVHNAKTKPREEQYNST YRVVSVLTVLHQDWLNGKEYKCK VSNKALPAPIEKTISKAKGQPRE PQVYTLPPSREEMTKNQVSLTCL VKGFYPSDIAVEWESNGQPENNY KTTPPVLDSDGSFFLYSKLTVDK SRWQQGNVFSCSVMHEALHNHYT QKSLSLSPGK (SEQ ID NO: 66) | DIVMTQSPLSLPVTP GEPASISCRSSQSIV HSNGNTYLQWYLQKP GQSPQLLIYKVSNRL YGVPDRFSGSGSGTD FTLKISRVEAEDVGV YYCFQGSHVPWTFGQ GTKVEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC (SEQ ID NO: 3) | QVQLQESGPGLVKPSETLSLTC TVSGYSITGGYLWNWIRQPPGK GLEWIGYISYDGTNNYKPSLKD RVTISRDTSKNQFSLKLSSVTA ADTAVYYCARYGRVFFDYWGQG TLVTVSSASTKGPSVFPLAPSS KSTSGGTAALGCLVKDYFPEPV TVSWNSGALTSGVHTFPAVLQS SGLYSLSSVVTVPSSSLGTQTY ICNVNHKPSNTKVDKRVEPKSC DKTHTCPPCPAPELLGGPSVFL FPPKPKDTLMISRTPEVTCVVV DVSHEDPEVKFNWYVDGVEVHN AKTKPREEQYNSTYRVVSVLTV LHQDWLNGKEYKCKVSNKALPA PIEKTISKAKGQPREPQVYTLP PSREEMTKNQVSLTCLVKGFYP SDIAVEWESNGQPENNYKTTPP VLDSDGSFFLYSKLTVDKSRWQ QGNVFSCSVMHEALHNHYTQKS LSLSPGK (SEQ ID NO: 4) |
| VRDN-02200 | SSELTQDPAVSVALGQTVRITCQ GDSLRSYYATWYQQKPGQAPILV IYGENKRPSGIPDRFSGSSSGNT ASLTITGAQAEDEADYYCKSRDG SGQHLVFGGGTKLTVLGQPKAAP SVTLFPPSSEELQANKATLVCLI SDFYPGAVTVAWKADSSPVKAGV ETTTPSKQSNNKYAASSYLSLTP EQWKSHRSYSCQVTHEGSTVEKT VAPAECS EVQLVQSGAEVKKPGSSVKVSCK ASGGTFSSYAISWVRQAPGQGLE WMGGIIPIFGTANYAQKFQGRVT ITADKSTSTAYMELSSLRSEDTA VYYCARAPLRFLEWSTQDHYYYY | SSELTQDPAVSVALG QTVRITCQGDSLRSY YATWYQQKPGQAPIL VIYGENKRPSGIPDR FSGSSSGNTASLTIT GAQAEDEADYYCKSR DGSGQHLVFGGGTKL TVLGQPKAAPSVTLF PPSSEELQANKATLV CLISDFYPGAVTVAW KADSSPVKAGVETTT PSKQSNNKYAASSYL SLTPEQWKSHRSYSC QVTHEGSTVEKTVAP AECS (SEQ | EVQLVQSGAEVKKPGSSVKVSC KASGGTFSSYAISWVRQAPGQG LEWMGGIIPIFGTANYAQKFQG RVTITADKSTSTAYMELSSLRS EDTAVYYCARAPLRFLEWSTQD HYYYYMDVWGKGTTVTVSSAS TKGPSVFPLAPSSKSTSGGTAA LGCLVKDYFPEPVTVSWNSGAL TSGVHTFPAVLQSSGLYSLSSV VTVPSSSLGTQTYICNVNHKPS NTKVDKKVEPKSCDKTHTCPPC PAPELLGGPSVFLFPPKPKDTL MISRTPEVTCVVVDVSHEDPEV KFNWYVDGVEVHNAKTKPREEQ YNSTYRVVSVLTVLHQDWLNGK |

-continued

| AB ID NO. | AB Sequence LC and HC | LC Sequence | HC Sequence |
|---|---|---|---|
| | YMDVWGKGTTVTVSSASTKGPSV FPLAPSSKSTSGGTAALGCLVKD YFPEPVTVSWNSGALTSGVHTFP AVLQSSGLYSLSSVVTVPSSSLG TQTYICNVNHKPSNTKVDKKVEP KSCDKTHTCPPCPAPELLGGPSV FLFPPKPKDTLMISRTPEVTCVV VDVSHEDPEVKFNWYVDGVEVHN AKTKPREEQYNSTYRVVSVLTVL HQDWLNGKEYKCKVSNKALPAPI EKTISKAKGQPREPQVYTLPPSR EEMTKNQVSLTCLVKGFYPSDIA VEWESNGQPENNYKTTPPVLDSD GSFFLYSKLTVDKSRWQQGNVFS CSVMHEALHNHYTQKSLSLSPGK (SEQ ID NO: 67) | NO: 5) | EYKCKVSNKALPAPIEKTISKA KGQPREPQVYTLPPSREEMTKN QVSLTCLVKGFYPSDIAVEWES NGQPENNYKTTPPVLDSDGSFF LYSKLTVDKSRWQQGNVFSCSV MHEALHNHYTQKSLSLSPGK (SEQ ID NO: 6) |
| VRDN-02300 | DIQMTQFPSSLSASVGDRVTITC RASQGIRNDLGWYQQKPGKAPKG LIYAASRLHRGVPSRFSGSGSGT EFTLTISSLQPEDFATYYCLQHN SYPCSFGQGTKLEIKRTVAAPSV FIFPPSDEQLKSGTASVVCLLNN FYPREAKVQWKVDNALQSGNSQE SVTEQDSKDSTYSLSSTLTLSKA DYEKHKVYACEVTHQGLSSPVTK SFNRGEC EVQLLESGGGLVQPGGSLRLSCT ASGFTFSSYAMNWVRQAPGKGLE WVSAISGSGGTTFYADSVKGRFT ISRDNSRTTLYLQMNSLRAEDTA VYYCAKDLGWSDSYYYYGMDVW GQGTTVTVSSASTKGPSVFPLAP CSRSTSESTAALGCLVKDYFPEP VTVSWNSGALTSGVHTFPAVLQS SGLYSLSSVVTVPSSNFGTQTYT CNVDHKPSNTKVDKTVERKCCVE CPPCPAPPVAGPSVFLFPPKPKD TLMISRTPEVTCVVVDVSHEDPE VQFNWYVDGVEVHNAKTKPREEQ FNSTFRVVSVLTVVHQDWLNGKE YKCKVSNKGLPAPIEKTISKTKG QPREPQVYTLPPSREEMTKNQVS LTCLVKGFYPSDIAVEWESNGQP ENNYKTTPPMLDSDGSFFLYSKL TVDKSRWQQGNVFSCSVMHEALH NHYTQKSLSLSPG (SEQ ID NO: 68) | DIQMTQFPSSLSASV GDRVTITCRASQGIR NDLGWYQQKPGKAPK RLIYAASRLHRGVPS RFSGSGSGTEFTLTI SSLQPEDFATYYCLQ HNSYPCSFGQGTKLE IKRTVAAPSVFIFPP SDEQLKSGTASVVCL LNNFYPREAKVQWKV DNALQSGNSQESVTE QDSKDSTYSLSSTLT LSKADYEKHKVYACE VTHQGLSSPVTKSFN RGEC (SEQ ID NO: 7) | EVQLLESGGGLVQPGGSLRLSC TASGFTFSSYAMNWVRQAPGKG LEWVSAISGSGGTTFYADSVKG RFTISRDNSRTTLYLQMNSLRA EDTAVYYCAKDLGWSDSYYYY GMDVWGQGTTVTVSSASTKGPS VFPLAPCSRSTSESTAALGCLV KDYFPEPVTVSWNSGALTSGVH TFPAVLQSSGLYSLSSVVTVPS SNFGTQTYTCNVDHKPSNTKVD KTVERKCCVECPPCPAPPVAGP SVFLFPPKPKDTLMISRTPEVT CVVVDVSHEDPEVQFNWYVDGV EVHNAKTKPREEQFNSTFRVVS VLTVVHQDWLNGKEYKCKVSNK GLPAPIEKTISKTKGQPREPQV YTLPPSREEMTKNQVSLTCLVK GFYPSDIAVEWESNGQPENNYK TTPPMLDSDGSFFLYSKLTVDK SRWQQGNVFSCSVMHEALHNHY TQKSLSLSPG (SEQ ID NO: 8) |
| VRDN-02400 | DVVMTQSPLSLPVTPGEPASISC RSSQSLLHSNGYNYLDWYLQKPG QSPQLLIYLGSNRASGVPDRFSG SGSGTDFTLKISRVEAEDVGVYY CMQGTHWPLTFGQGTKVEIKRTV AAPSVFIFPPSDEQLKSGTASVV CLLNNFYPREAKVQWKVDNALQS GNSQESVTEQDSKDSTYSLSSTL TLSKADYEKHKVYACEVTHQGLS SPVTKSFNRGEC QVQLQESGPGLVKPSGTLSLTCA VSGGSISSSNWWSWVRQPPGKGL EWIGEIYHSGSTNYNPSLKSRVT ISVDKSKNQFSLKLSSVTAADTA VYYCARWTGRTDAFDIWGQGTMV TVSSASTKGPSVFPLAPSSKSTS GGTAALGCLVKDYFPEPVTVSWN SGALTSGVHTFPAVLQSSGLYSL SSVVTVPSSSLGTQTYICNVNHK PSNTKVDKKVEPKSCDKTHTCPP CPAPELLGGPSVFLFPPKPKDTL MISRTPEVTCVVVDVSHEDPEVK FNWYVDGVEVHNAKTKPREEQYN STYRVVSVLTVLHQDWLNGKEYK CKVSNKALPAPIEKTISKAKGQP REPQVYTLPPSRDELTKNQVSLT CLVKGFYPSDIAVEWESNGQPEN NYKTTPPVLDSDGSFFLYSKLTV | DVVMTQSPLSLPVTP GEPASISCRSSQSLL HSNGYNYLDWYLQKP GQSPQLLIYLGSNRA SGVPDRFSGSGSGTD FTLKISRVEAEDVGV YYCMQGTHWPLTFGQ GTKVEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC (SEQ ID NO: 9) | QVQLQESGPGLVKPSGTLSLTC AVSGGSISSSNWWSWVRQPPGK GLEWIGEIYHSGSTNYNPSLKS RVTISVDKSKNQFSLKLSSVTA ADTAVYYCARWTGRTDAFDIWG QGTMVTVSSASTKGPSVFPLAP SSKSTSGGTAALGCLVKDYFPE PVTVSWNSGALTSGVHTFPAVL QSSGLYSLSSVVTVPSSSLGTQ TYICNVNHKPSNTKVDKKVEPK SCDKTHTCPPCPAPELLGGPSV FLFPPKPKDTLMISRTPEVTCV VVDVSHEDPEVKFNWYVDGVEV HNAKTKPREEQYNSTYRVVSVL TVLHQDWLNGKEYKCKVSNKAL PAPIEKTISKAKGQPREPQVYT LPPSRDELTKNQVSLTCLVKGF YPSDIAVEWESNGQPENNYKTT PPVLDSDGSFFLYSKLTVDKSR WQQGNVFSCSVMHEALHNHYTQ KSLSLSPGK (SEQ ID NO: 10) |

-continued

| AB ID NO. | AB Sequence LC and HC | LC Sequence | HC Sequence |
|---|---|---|---|
| | DKSRWQQGNVFSCSVMHEALHNH YTQKSLSLSPGK (SEQ ID NO: 69) | | |
| VRDN-02500 | EIVLTQSPGTLSVSPGERATLSC RASQSIGSSLHWYQQKPGQAPRL LIKYASQSLSGIPDRFSGSGSGT DFTLTISRLEPEDFAVYYCHQSS RLPHTFGQGTKVEIKRTVAAPSV FIFPPPSDEQLKSGTASVVCLLNN FYPREAKVQWKVDNALQSGNSQE SVTEQDSKDSTYSLSSTLTLSKA DYEKHKVYACEVTHQGLSSPVTK SFNRGEC EVQLVQSGGGLVKPGGSLRLSCA ASGFTFSSFAMHWVRQAPGKGLE WISVIDTRGATYYADSVKGRFTI SRDNAKNSLYLQMNSLRAEDTAV YYCARLGNFYYGMDVWGQGTTVT VSSASTKGPSVFPLAPSSKSTSG GTAALGCLVKDYFPEPVTVSWNS GALTSGVHTFPAVLQSSGLYSLS SVVTVPSSSLGTQTYICNVNHKP SNTKVDKKVEPKSCDKTHTCPPC PAPELLGGPSVFLFPPKPKDTLM ISRTPEVTCVVVDVSHEDPEVKF NWYVDGVEVHNAKTKPREEQYNS TYRVVSVLTVLHQDWLNGKEYKC KVSNKALPAPIEKTISKAKGQPR EPQVYTLPPSRDELTKNQVSLTC LVKGFYPSDIAVEWESNGQPENN YKTTPPVLDSDGSFFLYSKLTVD KSRWQQGNVFSCSVMHEALHNHY TQKSLSLSPGK (SEQ ID NO: 70) | EIVLTQSPGTLSVSP GERATLSCRASQSIG SSLHWYQQKPGQAPR LLIKYASQSLSGIPD RFSGSGSGTDFTLTI SRLEPEDFAVYYCHQ SSRLPHTFGQGTKVE IKRTVAAPSVFIFPP SDEQLKSGTASVVCL LNNFYPREAKVQWKV DNALQSGNSQESVTE QDSKDSTYSLSSTLT LSKADYEKHKVYACE VTHQGLSSPVTKSFN RGEC (SEQ ID NO: 11) | EVQLVQSGGGLVKPGGSLRLSC AASGFTFSSFAMHWVRQAPGKG LEWISVIDTRGATYYADSVKGR FTISRDNAKNSLYLQMNSLRAE DTAVYYCARLGNFYYGMDVWGQ GTTVTVSSASTKGPSVFPLAPS SKSTSGGTAALGCLVKDYFPEP VTVSWNSGALTSGVHTFPAVLQ SSGLYSLSSVVTVPSSSLGTQT YICNVNHKPSNTKVDKKVEPKS CDKTHTCPPCPAPELLGGPSVF LFPPKPKDTLMISRTPEVTCVV VDVSHEDPEVKFNWYVDGVEVH NAKTKPREEQYNSTYRVVSVLT VLHQDWLNGKEYKCKVSNKALP APIEKTISKAKGQPREPQVYTL PPSRDELTKNQVSLTCLVKGFY PSDIAVEWESNGQPENNYKTTP PVLDSDGSFFLYSKLTVDKSRW QQGNVFSCSVMHEALHNHYTQK SLSLSPGK (SEQ ID NO: 12) |
| VRDN-02700 | DIVMTQSPLSLPVTPGEPASISC RSSQSIVHSNGNTYLQWYLQKPG QSPQLLIYKVSNRLYGVPDRFSG SGSGTDFTLKISRVEAEDVGVYY CFQGSHVPWTFGQGTKVEIKRTV AAPSVFIFPPSDEQLKSGTASVV CLLNNFYPREAKVQWKVDNALQS GNSQESVTEQDSKDSTYSLSSTL TLSKADYEKHKVYACEVTHQGLS SPVTKSFNRGEC QVQLQESGPGLVKPSETLSLTCT VSGYSITGGYLWNWIRQPPGKGL EWIGYISYDGTNNYKPSLKDRVT ISRDTSKNQFSLKLSSVTAADTA VYYCARYGRVFFDYWGQGTLVTV SSASTKGPSVFPLAPSSKSTSGG TAALGCLVKDYFPEPVTVSWNSG ALTSGVHTFPAVLQSSGLYSLSS VVTVPSSSLGTQTYICNVNHKPS NTKVDKRVEPKSCDKTHTCPPCP APELLGGPSVFLFPPKPKDTLYI TREPEVTCVVVDVSHEDPEVKFN WYVDGVEVHNAKTKPREEQYNST YRVVSVLTVLHQDWLNGKEYKCK VSNKALPAPIEKTISKAKGQPRE PQVYTLPPSREEMTKNQVSLTCL VKGFYPSDIAVEWESNGQPENNY KTTPPVLDSDGSFFLYSKLTVDK SRWQQGNVFSCSVMHEALHNHYT QKSLSLSPG (SEQ ID NO: 82) | DIVMTQSPLSLPVTP GEPASISCRSSQSIV HSNGNTYLQWYLQKP GQSPQLLIYKVSNRL YGVPDRFSGSGSGTD FTLKISRVEAEDVGV YYCFQGSHVPWTFGQ GTKVEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC (SEQ ID NO: 3) | QVQLQESGPGLVKPSETLSLTC TVSGYSITGGYLWNWIRQPPGK GLEWIGYISYDGTNNYKPSLKD RVTISRDTSKNQFSLKLSSVTA ADTAVYYCARYGRVFFDYWGQG TLVTVSSASTKGPSVFPLAPSS KSTSGGTAALGCLVKDYFPEPV TVSWNSGALTSGVHTFPAVLQS SGLYSLSSVVTVPSSSLGTQTY ICNVNHKPSNTKVDKRVEPKSC DKTHTCPPCPAPELLGGPSVFL FPPKPKDTLYITREPEVTCVVV DVSHEDPEVKFNWYVDGVEVHN AKTKPREEQYNSTYRVVSVLTV LHQDWLNGKEYKCKVSNKALPA PIEKTISKAKGQPREPQVYTLP PSREEMTKNQVSLTCLVKGFYP SDIAVEWESNGQPENNYKTTPP VLDSDGSFFLYSKLTVDKSRWQ QGNVFSCSVMHEALHNHYTQKS LSLSPG (SEQ ID NO: 83) |

In some embodiments, the antibody comprises one or more peptides having the following sequences, or a variant thereof:

| AB ID NO. | AB Sequence of LC and HC | VL Sequence | VH Sequence |
|---|---|---|---|
| VRDN-01100 | DVVMTQTPLSLPVSLGDPASISC RSSQSIVHSNVNTYLEWYLQKPG QSPRLLIYKVSNRFSGVPDRFSG SGAGTDFTLRISRVEAEDLGIYY CFQGSHVPPTFGGGTKLEIKRTV AAPSVFIFPPSDEQLKSGTASVV CLLNNFYPREAKVQWKVDNALQS GNSQESVTEQDSKDSTYSLSSTL TLSKADYEKHKVYACEVTHQGLS SPVTKSFNRGEC QVQLVQSGAEVVKPGASVKLSCK ASGYTFTSYWMHWVKQRPGQGLE WIGEINPSNGRTNYNQKFQGKAT LTVDKSSSTAYMQLSSLTSEDSA VYYFARGRPDYYGSSKWYFDVWG QGTTVTVSSASTKGPSVFPLAPS SKSTSGGTAALGCLVKDYFPEPV TVSWNSGALTSGVHTFPAVLQSS GLYSLSSVVTVPSSSLGTQTYIC NVNHKPSNTKVDKKVEPKSCDKT HTCPPCPAPELLGGPSVFLFPPK PKDTLMISRTPEVTCVVVDVSHE DPEVKFNWYVDGVEVHNAKTKPR EEQYNSTYRVVSVLTVLHQDWLN GKEYKCKVSNKALPAPIEKTISK AKGQPREPQVYTLPPSRDELTKN QVSLTCLVKGFYPSDIAVEWESN GQPENNYKTTPPVLDSDGSFFLY SKLTVDKSRWQQGNVFSCSVMHE ALHNHYTQKSLSLSPGK (SEQ ID NO: 71) | DVVMTQTPLSLPVSL GDPASISCRSSQSIV HSNVNTYLEWYLQKP GQSPRLLIYKVSNRF SGVPDRFSGSGAGTD FTLRISRVEAEDLGI YYCFQGSHVPPTFGG GTKLEIKR (SEQ ID NO: 13) | QVQLVQSGAEVVKPGASVKLSC KASGYTFTSYWMHWVKQRPGQG LEWIGEINPSNGRTNYNQKFQG KATLTVDKSSSTAYMQLSSLTS EDSAVYYFARGRPDYYGSSKWY FDVWGQGTTVTVSS (SEQ ID NO: 14) |
| VRDN-02600 | DIQMTQSPLSLSASVGDRVTITC QASRDIRNYLNWYQQKPGKAPKL LIYDASSLQTGVPSRFGGSGSGT DFSFTIGSLQPEDIATYYCQQFD SLPHTFGQGTKLEIK EVQLLESGGGLVQPGGSLRLSCA ASGFTFSIYRMQWVRQAPGKGLE WVSGISPSGGTTWYADSVKGRFT ISRDNSKNTLYLQMNSLRAEDTA VYYCARWSGGSGYAFDIWGQGTM VTVSS (SEQ ID NO: 72) | DIQMTQSPLSLSASV GDRVTITCQASRDIR NYLNWYQQKPGKAPK LLIYDASSLQTGVPS RFGGSGSGTDFSFTI GSLQPEDIATYYCQQ FDSLPHTFGQGTKLE IK (SEQ ID NO: 15) | EVQLLESGGGLVQPGGSLRLSC AASGFTFSIYRMQWVRQAPGKG LEWVSGISPSGGTTWYADSVKG RFTISRDNSKNTLYLQMNSLRA EDTAVYYCARWSGGSGYAFDIW GQGTMVTVSS (SEQ ID NO: 16) |
| VRDN-02301 | DIQMTQFPSSLSASVGDRVTITC RASQGIRNDLGWYQQKPGKAPKR LIYAASRLHRGVPSRFSGSGSGT EFTLTISSLQPEDFATYYCLQHN SYPSSFGQGTKLEIKEVQLLESG GGLVQPGGSLRLSCTASGFTFSS YAMNWVRQAPGKGLEWVSAISGS GGTTFYADSVKGRFTISRDNSRT TLYLQMNSLRAEDTAVYYCAKDL GWSDSYYYYGMDVWGQGTTVTV SS (SEQ ID NO: 78) | DIQMTQFPSSLSASV GDRVTITCRASQGIR NDLGWYQQKPGKAPK RLIYAASRLHRGVPS RFSGSGSGTEFTLTI SSLQPEDFATYYCLQ HNSYPSSFGQGTKLE IK (SEQ ID NO: 79) | EVQLLESGGGLVQPGGSLRLSC TASGFTFSSYAMNWVRQAPGKG LEWVSAISGSGGTTFYADSVKG RFTISRDNSRTTLYLQMNSLRA EDTAVYYCAKDLGWSDSYYYYY GMDVWGQGTTVTVSS (SEQ ID NO: 80) |
| VRDN-01101 | DVVMTQTPLSLPVSLGDPASISC RSSQSIVHSNVNTYLEWYLQKPG QSPKLLIYKVSNRFSGVPDRFSG SGAGTDFTLRISRVEAEDLGIYY CFQGSHVPPTFGGGTKLEIKRTV AAPSVFIFPPSDEQLKSGTASVV CLLNNFYPREAKVQWKVDNALQS GNSQESVTEQDSKDSTYSLSSTL TLSKADYEKHKVYACEVTHQGLS SPVTKSFNRGEC (Light Chain) QVQLVQSGAEVVKPGASVKLSCK ASGYTFTSYWMHWVKQRPGQGLE WIGEINPSNGRTNYNQKFQGKAT LTVDKSSSTAYMQLSSLTSEDSA VYYFARGRPDYYGSSKWYFDVWG QGTTVTVSSASTKGPSVFPLAPS SKSTSGGTAALGCLVKDYFPEPV | DVVMTQTPLSLPVSL GDPASISCRSSQSIV HSNVNTYLEWYLQKP GQSPKLLIYKVSNRF SGVPDRFSGSGAGTD FTLRISRVEAEDLGI YYCFQGSHVPPTFGG GTKLEIKR (SEQ ID NO: 86) | QVQLVQSGAEVVKPGASVKLSC KASGYTFTSYWMHWVKQRPGQG LEWIGEINPSNGRTNYNQKFQG KATLTVDKSSSTAYMQLSSLTS EDSAVYYFARGRPDYYGSSKWY FDVWGQGTTVTVSS (SEQ ID NO: 14) |

| AB ID NO. | AB Sequence of LC and HC VL Sequence | | VH Sequence |
|---|---|---|---|
| | TVSWNSGALTSGVHTFPAVLQSS GLYSLSSVVTVPSSSLGTQTYIC NVNHKPSNTKVDKKVEPKSCDKT HTCPPCPAPELLGGPSVFLFPPK PKDTLMISRTPEVTCVVVDVSHE DPEVKFNWYVDGVEVHNAKTKPR EEQYNSTYRVVSVLTVLHQDWLN GKEYKCKVSNKALPAPIEKTISK AKGQPREPQVYTLPPSRDELTKN QVSLTCLVKGFYPSDIAVEWESN GQPENNYKTTPPVLDSDGSFFLY SKLTVDKSRWQQGNVFSCSVMHE ALHNHYTQKSLSLSPGK (SEQ ID NO: 85; heavy chain) | | |
| VRDN-2700 | DIVMTQSPLSLPVTPGEPASISC RSSQSIVHSNGNTYLQWYLQKPG QSPQLLIYKVSNRLYGVPDRFSG SGSGTDFTLKISRVEAEDVGVYY CFQGSHVPWTFGQGTKVEIKRTV AAPSVFIFPPSDEQLKSGTASVV CLLNNFYPREAKVQWKVDNALQS GNSQESVTEQDSKDSTYSLSSTL TLSKADYEKHKVYACEVTHQGLS SPVTKSFNRGEC (Light Chain) QVQLQESGPGLVKPSETLSLTCT VSGYSITGGYLWNWIRQPPGKGL EWIGYISYDGTNNYKPSLKDRVT ISRDTSKNQFSLKLSSVTAADTA VYYCARYGRVFFDYWGQGTLVTV SSASTKGPSVFPLAPSSKSTSGG TAALGCLVKDYFPEPVTVSWNSG ALTSGVHTFPAVLQSSGLYSLSS VVTVPSSSLGTQTYICNVNHKPS NTKVDKRVEPKSCDKTHTCPPCP APELLGGPSVFLFPPKPKDTLYI TREPEVTCVVVDVSHEDPEVKFN WYVDGVEVHNAKTKPREEQYNST YRVVSVLTVLHQDWLNGKEYKCK VSNKALPAPIEKTISKAKGQPRE PQVYTLPPSREEMTKNQVSLTCL VKGFYPSDIAVEWESNGQPENNY KTTPPVLDSDGSFFLYSKLTVDK SRWQQGNVFSCSVMHEALHNHYT QKSLSLSPG (Heavy Chain) (SEQ ID NO: 82) | DIVMTQSPLSLPVTP GEPASISCRSSQSIV HSNGNTYLQWYLQKP GQSPQLLIYKVSNRL YGVPDRFSGSGSGTD FTLKISRVEAEDVGV YYCFQGSHVPWTFGQ GTKVEIKR (SEQ ID NO: 98) | QVQLQESGPGLVKPSETLSLTC TVSGYSITGGYLWNWIRQPPGK GLEWIGYISYDGTNNYKPSLKD RVTISRDTSKNQFSLKLSSVTA ADTAVYYCARYGRVFFDYWGQG TLVTVSS (SEQ ID NO: 99) |

The column that is indicated as the antibody sequence comprises the VH and VL chains of the antibody. In instances where the VH chain is illustrated with a Fc sequence, the Fc sequence can be modified or substituted for a different Fc region as provided for herein. However, in some embodiments, the antibody can comprise the VH and VL sequence as provided for in the tables provided for herein. For example, in some embodiments, the antibody comprises one or more VH, HC, LC, or VL (those sequence that have a constant domain are the complete light or heavy chain) having the following sequences, or a variant thereof:

| AB ID NO. | VL or LC Sequence | VH or HC Sequence |
|---|---|---|
| VRDN-03100 | EIVLTQSPATLSLSP GERATLSCRASQSVS SYLAWYQQKPGQAPR LLIYDASKRATGIPA RFSGSGSGTDFTLTI SSLEPEDFAVYYCQQ RSKWPPWTFGQGTKV EIKRTVAAPSVFIFP PSDEQLKSGTASVVC | QVELVESGGGVVQPGRSQRLSC AASGFTFSSYGMHWVRQAPGKG LEWVAIIWFDGSSTYYADSVRG RFTISRDNSKNTLYLQMNSLRA EDTAVYFCARELGRRYFDLWGR GTLVSSSASTKGPSVFPLAPS SKSTSGGTAALGCLVKDYFPEP VTVSWNSGALTSGVHTFPAVLQ SSGLYSLSSVVTVPSSSLGTQT |
| | LLNNFYPREAKVQWK VDNALQSGNSQESVT EQDSKDSTYSLSSTL TLSKADYEKHKVYAC EVTHQGLSSPVTKSF NRGEC (SEQ ID NO: 1) | YICNVNHKPSNTKVDKKVEPKS CDKTHTCPPCPAPELLGGPSVF LFPPKPKDTLMISRTPEVTCVV VDVSHEDPEVKFNWYVDGVEVH NAKTKPREEQYNSTYRVVSVLT VLHQDWLNGKEYKCKVSNKALP APIEKTISKAKGQPREPQVYTL PPSRDELTKNQVSLTCLVKGFY PSDIAVEWESNGQPENNYKTTP PVLDSDGSFFLYSKLTVDKSRW QQGNVFSCSVMHEALHNHYTQK SLSLSPGK (SEQ ID NO: 2) |
| VRDN-02100 | DIVMTQSPLSLPVTP GEPASISCRSSQSIV HSNGNTYLQWYLQKP GQSPQLLIYKVSNRL YGVPDRFSGSGSGTD FTLKISRVEAEDVGV YYCFQGSHVPWTFGQ GTKVEIKRTVAAPSV | QVQLQESGPGLVKPSETLSLTC TVSGYSITGGYLWNWIRQPPGK GLEWIGYISYDGTNNYKPSLKD RVTISRDTSKNQFSLKLSSVTA ADTAVYYCARYGRVFFDYWGQG TLVTVSSASTKGPSVFPLAPSS KSTSGGTAALGCLVKDYFPEPV TVSWNSGALTSGVHTFPAVLQS |

| AB ID NO. | VL or LC Sequence | VH or HC Sequence |
|---|---|---|
| | FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC (SEQ ID NO: 3) | SGLYSLSSVVTVPSSSLGTQTY ICNVNHKPSNTKVDKRVEPKSC DKTHTCPPCPAPELLGGPSVFL FPPKPKDTLMISRTPEVTCVVV DVSHEDPEVKFNWYVDGVEVHN AKTKPREEQYNSTYRVVSVLTV LHQDWLNGKEYKCKVSNKALPA PIEKTISKAKGQPREPQVYTLP PSREEMTKNQVSLTCLVKGFYP SDIAVEWESNGQPENNYKTTPP VLDSDGSFFLYSKLTVDKSRWQ QGNVFSCSVMHEALHNHYTQKS LSLSPGK (SEQ ID NO: 4) |
| VRDN-02200 | SSELTQDPAVSVALG QTVRITCQGDSLRSY YATWYQQKPGQAPIL VIYGENKRPSGIPDR FSGSSSGNTASLTIT GAQAEDEADYYCKSR DGSGQHLVFGGGTKL TVLGQPKAAPSVTLF PPSSEELQANKATLV CLISDFYPGAVTVAW KADSSPVKAGVETTT PSKQSNNKYAASSYL SLTPEQWKSHRSYSC QVTHEGSTVEKTVAP AECS (SEQ ID NO: 5) | EVQLVQSGAEVKKPGSSVKVSC KASGGTFSSYAISWVRQAPGQG LEWMGGIIPIFGTANYAQKFQG RVTITADKSTSTAYMELSSLRS EDTAVYYCARAPLRFLEWSTQD HYYYYYMDVWGKGTTVTVSSAS TKGPSVFPLAPSSKSTSGGTAA LGCLVKDYFPEPVTVSWNSGAL TSGVHTFPAVLQSSGLYSLSSV VTVPSSSLGTQTYICNVNHKPS NTKVDKKVEPKSCDKTHTCPPC PAPELLGGPSVFLFPPKPKDTL MISRTPEVTCVVVDVSHEDPEV KFNWYVDGVEVHNAKTKPREEQ YNSTYRVVSVLTVLHQDWLNGK EYKCKVSNKALPAPIEKTISKA KGQPREPQVYTLPPSREEMTKN QVSLTCLVKGFYPSDIAVEWES NGQPENNYKTTPPVLDSDGSFF LYSKLTVDKSRWQQGNVFSCSV MHEALHNHYTQKSLSLSPGK (SEQ ID NO: 6) |
| VRDN-02300 | DIQMTQFPSSLSASV GDRVTITCRASQGIR NDLGWYQQKPGKAPK RLIYAASRLHRGVPS RFSGSGSGTEFTLTI SSLQPEDFATYYCLQ HNSYPCSFGQGTKLE IKRTVAAPSVFIFPP SDEQLKSGTASVVCL LNNFYPREAKVQWKV DNALQSGNSQESVTE QDSKDSTYSLSSTLT LSKADYEKHKVYACE VTHQGLSSPVTKSFN RGEC (SEQ ID NO: 7) | EVQLLESGGGLVQPGGSLRLSC TASGFTFSSYAMNWVRQAPGKG LEWVSAISGSGGTTFYADSVKG RFTISRDNSRTTLYLQMNSLRA EDTAVYYCAKDLGWSDSYYYYY GMDVWGQGTTVTVSSASTKGPS VFPLAPCSRSTSESTAALGCLV KDYFPEPVTVSWNSGALTSGVH TFPAVLQSSGLYSLSSVVTVPS SNFGTQTYTCNVDHKPSNTKVD KTVERKCCVECPPCPAPPVAGP SVFLFPPKPKDTLMISRTPEVT CVVVDVSHEDPEVQFNWYVDGV EVHNAKTKPREEQFNSTFRVVS VLTVVHQDWLNGKEYKCKVSNK GLPAPIEKTISKTKGQPREPQV YTLPPSREEMTKNQVSLTCLVK GFYPSDIAVEWESNGQPENNYK TTPPMLDSDGSFFLYSKLTVDK SRWQQGNVFSCSVMHEALHNHY TQKSLSLSPG (SEQ ID NO: 8) |
| VRDN-02400 | DVVMTQSPLSLPVTP GEPASISCRSSQSLL HSNGYNYLDWYLQKP GQSPQLLIYLGSNRA SGVPDRFSGSGSGTD FTLKISRVEAEDVGV YYCMQGTHWPLTFGQ GTKVEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC (SEQ ID NO: 9) | QVQLQESGPGLVKPSGTLSLTC AVSGGSISSSNWWSWVRQPPGK GLEWIGEIYHSGSTNYNPSLKS RVTISVDKSKNQFSLKLSSVTA ADTAVYYCARWTGRTDADIWIG QGTMVTVSSASTKGPSVFPLAP SSKSTSGGTAALGCLVKDYFPE PVTVSWNSGALTSGVHTFPAVL QSSGLYSLSSVVTVPSSSLGTQ TYICNVNHKPSNTKVDKKVEPK SCDKTHTCPPCPAPELLGGPSV FLFPPKPKDTLMISRTPEVTCV VVDVSHEDPEVKFNWYVDGVEV HNAKTKPREEQYNSTYRVVSVL TVLHQDWLNGKEYKCKVSNKAL PAPIEKTISKAKGQPREPQVYT LPPSRDELTKNQVSLTCLVKGF YPSDIAVEWESNGQPENNYKTT PPVLDSDGSFFLYSKLTVDKSR WQQGNVFSCSVMHEALHNHYTQ KSLSLSPGK (SEQ ID NO: 10) |
| VRDN-02500 | EIVLTQSPGTLSVSP GERATLSCRASQSIG SSLHWYQQKPGQAPR LLIKYASQSLSGIPD RFSGSGSGTDFTLTI SRLEPEDFAVYYCHQ SSRLPHTFGQGTKVE IKRTVAAPSVFIFPP SDEQLKSGTASVVCL LNNFYPREAKVQWKV DNALQSGNSQESVTE QDSKDSTYSLSSTLT LSKADYEKHKVYACE VTHQGLSSPVTKSFN RGEC (SEQ ID NO: 11) | EVQLVQSGGGLVKPGGSLRLSC AASGFTFSSFAMHWVRQAPGKG LEWISVIDTRGATYYADSVKGR FTISRDNAKNSLYLQMNSLRAE DTAVYYCARLGNFYYGMDVWGQ GTTVTVSSASTKGPSVFPLAPS SKSTSGGTAALGCLVKDYFPEP VTVSWNSGALTSGVHTFPAVLQ SSGLYSLSSVVTVPSSSLGTQT YICNVNHKPSNTKVDKKVEPKS CDKTHTCPPCPAPELLGGPSVF LFPPKPKDTLMISRTPEVTCVV VDVSHEDPEVKFNWYVDGVEVH NAKTKPREEQYNSTYRVVSVLT VLHQDWLNGKEYKCKVSNKALP APIEKTISKAKGQPREPQVYTL PPSRDELTKNQVSLTCLVKGFY PSDIAVEWESNGQPENNYKTTP PVLDSDGSFFLYSKLTVDKSRW QQGNVFSCSVMHEALHNHYTQK SLSLSPGK (SEQ ID NO: 12) |
| VRDN-02700 | DIVMTQSPLSLPVTP GEPASISCRSSQSIV HSNGNTYLQWYLQKP GQSPQLLIYKVSNRL YGVPDRFSGSGSGTD FTLKISRVEAEDVGV YYCFQGSHVPWTFGQ GTKVEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC (SEQ ID NO: 3) | QVQLQESGPGLVKPSETLSLTC TVSGYSITGGYLWNWIRQPPGK GLEWIGYISYDGTNNYKPSLKD RVTISRDTSKNQFSLKLSSVTA ADTAVYYCARYGRVFFDYWGQG TLVTVSSASTKGPSVFPLAPSS KSTSGGTAALGCLVKDYFPEPV TVSWNSGALTSGVHTFPAVLQS SGLYSLSSVVTVPSSSLGTQTY ICNVNHKPSNTKVDKRVEPKSC DKTHTCPPCPAPELLGGPSVFL FPPKPKDTLYITREPEVTCVVV DVSHEDPEVKFNWYVDGVEVHN AKTKPREEQYNSTYRVVSVLTV LHQDWLNGKEYKCKVSNKALPA PIEKTISKAKGQPREPQVYTLP PSREEMTKNQVSLTCLVKGFYP SDIAVEWESNGQPENNYKTTPP VLDSDGSFFLYSKLTVDKSRWQ QGNVFSCSVMHEALHNHYTQKS LSLSPG (SEQ ID NO: 83) |
| VRDN-01100 | DVVMTQTPLSLPVSL GDPASISCRSSQSIV HSNVNTYLEWYLQKP GQSPRLLIYKVSNRF SGVPDRFSGSGAGTD FTLRISRVEAEDLGI YYCFQGSHVPPTFGG GTKLEIKR (SEQ ID NO: 13) | QVQLVQSGAEVKPGASVKLSC KASGYTFTSYWMHWVKQRPGQG LEWIGEINPSNGRTNYNQKFQG KATLTVDKSSSTAYMQLSSLTS EDSAVYYFARGRPDYYGSSKWY FDVWGQGTTVTVSS (SEQ ID NO: 14) |
| VRDN-02600 | DIQMTQSPLSLSASV GDRVTITCQASRDIR NYLNWYQQKPGKAPK LLIYDASSLQTGVPS RFGGSGSGTDFSFTI GSLQPEDIATYYCQQ FDSLPHTFGQGTKLE IK (SEQ ID NO: 15) | EVQLLESGGGLVQPGGSLRLSC AASGFTFSIYRMQWVRQAPGKG LEWVSGISPSGGTTWYADSVKG RFTISRDNSKNTLYLQMNSLRA EDTAVYYCARWSGGSGYAFDIW GQGTMVTVSS (SEQ ID NO: 16) |
| VRDN-02301 | DIQMTQFPSSLSASV GDRVTITCRASQGIR NDLGWYQQKPGKAPK RLIYAASRLHRGVPS RFSGSGSGTDFSFTI EDTAVYYCARWSGGSGYAFDIW | EVQLLESGGGLVQPGGSLRLSC TASGFTFSSYAMNWVRQAPGKG LEWVSAISGSGGTTFYADSVKG RFTISRDNSRTTLYLQMNSLRA |

-continued

| AB ID NO. | VL or LC Sequence | VH or HC Sequence |
|---|---|---|
|  | RFSGSGSGTEFTLTI SSLQPEDFATYYCLQ HNSYPSSFGQGTKLE IK (SEQ ID NO: 79) | EDTAVYYCAKDLGWSDSYYYY GMDVWGQGTTVTVSS (SEQ ID NO: 80) |
| VRDN-01101 | DVVMTQTPLSLPVSL GDPASISCRSSQSIV HSNVNTYLEWYLQKP GQSPKLLIYKVSNRF SGVPDRFSGSGAGTD FTLRISRVEAEDLGI YYCFQGSHVPPTFGG GTKLEIKR (SEQ ID NO: 86) | QVQLVQSGAEVVKPGASVKLSC KASGYTFTSYWMHWVKQRPGQG LEWIGEINPSNGRTNYNQKFQG KATLTVDKSSSTAYMQLSSLTS EDSAVYYFARGRPDYYGSSKWY FDVWGQGTTVTVSS (SEQ ID NO: 14) |
| VRDN-01100A or 01110B | DVVMTQTPLSLPVSL GDPASISCRSSQSIV HSNVNTYLEWYLQKP GQSPKLLIYKVSNRF SGVPDRFSGSGAGTD FTLRISRVEAEDLGI YYCFQGSHVPPTFGG GTKLEIKR (SEQ ID NO: 86) | QVQLVQSGAEVVKPGASVKLSS KASGYTFTSYWMHWVKQRPGQG LEWIGEINPSNGRTNYNQKFQG KATLTVDKSSSTAYMQLSSLTS EDSAVYYFARGRPDYYGSSKWY FDVWGQGTTVTVSS (SEQ ID NO: 91) |

In some embodiments, the variable light chain as set forth in SEQ ID NO: 13 does not have the C-terminal arginine residue. This is illustrated for example, in the following sequence:

(SEQ ID NO: 97)
DVVMTQTPLSLPVSLGDPASISCRSSQSIVHSNVNTYLEWYLQKPGQSPR

LLIYKVSNRFSGVPDRFSGSGAGTDFTLRISRVEAEDLGIYYCFQGSHVP

PTFGGGTKLEIK.

Thus, in some embodiments, where the variable light chain comprises the sequence of SEQ ID NO: 13, it can be substituted with a sequence of SEQ ID NO: 97.

In some embodiments, the heavy chain variable region as set forth in SEQ ID NO: 14 can comprises a C22S substitution. This is illustrated in the following sequence: IDC-27 DNA (SEQ ID NO: 96)
QVQLVQSGAEVVKPGASVKLSSKASGYTFTSYWMHWVKQRPGQGLEWIGE

INPSNGRTNYNQKFQGKATLTVDKSSSTAYMQLSSLTSEDSAVYYFARGR

PDYYGSSKWYFDVWGQGTTVTVSS.

Accordingly, in some embodiments, the antibody comprises a VH sequence of SEQ ID NO: 96 and a VL sequence of SEQ ID NO: 13 or SEQ ID NO: 97.

In some embodiments, the antibody comprises a VH of SEQ ID NO: 14 and a VL sequence of SEQ ID NO: 97.

In some embodiments, the antibody comprises a VL of SEQ ID NO: 98 and a VH of SEQ ID NO: 99. In some embodiments, the antibody comprises a VL of SEQ ID NO: 98 and a VH of SEQ ID NO: 99 with a Fc region comprising the M252Y, S254T, and T256E mutations. In some embodiments, the antibody comprises a VL of SEQ ID NO: 98 and a VH of SEQ ID NO: 99 with a Fc region comprising the M428L and N434S mutations.

As provided for herein, the heavy chain can be linked to a Fc region, including those with mutations that can affect the half-life of the antibody. Non-limiting mutations in the Fc region are provided for herein.

In the tables provided for herein, the LC and HC may be illustrated with the VH and VL domains with or without constant regions. The constant regions can be replaced as provided for herein. The VH and VL regions can be used to form an antibody as provided for herein. The VH and the VL sequences can be in any format, including, but not limited to a scFv format where the VH and VL regions are linked with a peptide linker. Examples of peptide linkers that can be used to link various peptides provided for herein include, but are not limited to: (GGGGS)$_n$ (SEQ ID NO: 73); (GGGGA)$_n$ (SEQ ID NO: 74), or any combination thereof, wherein each n is independently 1-5. In some embodiments, the variable regions are not linked with a peptide linker. In some embodiments, the antibody comprises SEQ ID NO: 1 and SEQ ID NO: 2, or the CDR regions thereof. In some embodiments, the antibody comprises SEQ ID NO: 3 and SEQ ID NO: 4, or the CDR regions thereof. In some embodiments, the antibody comprises SEQ ID NO: 5 and SEQ ID NO: 6, or the CDR regions thereof. In some embodiments, the antibody comprises SEQ ID NO: 7 and SEQ ID NO: 8, or the CDR regions thereof. In some embodiments, the antibody comprises SEQ ID NO: 9 and SEQ ID NO: 10, or the CDR regions thereof. In some embodiments, the antibody comprises SEQ ID NO: 11 and SEQ ID NO: 12, or the CDR regions thereof. In some embodiments, the antibody comprises SEQ ID NO: 13 and SEQ ID NO: 14, or the CDR regions thereof. In some embodiments, the antibody comprises SEQ ID NO: 15 and SEQ ID NO: 16, or the CDR regions thereof.

In some embodiments, an antibody, or antigen binding fragment thereof is provided, wherein the antibody or antibody fragment comprises a peptide selected from the following table.

| Ab ID No | LCDR1 | LCDR2 | LCDR3 | HCDR1 | HCDR2 | HCDR3 |
|---|---|---|---|---|---|---|
| VRDN-03100 | RASQSV SSYLA (SEQ ID NO: 17) | DASKRAT (SEQ ID NO: 18) | QQRSKWPPWT (SEQ ID NO: 19) | SYGMH (SEQ ID NO: 20) | IIWFDGSSTYYADS VRG (SEQ ID NO: 21) | ELGRRYFDL (SEQ ID NO: 22) |
| VRDN-02100/2700 | RSSQSI VHSNGN TYLQWY LQ (SEQ ID NO: 23) | KVSNRLY (SEQ ID NO: 24) | FQGSHVPWT (SEQ ID NO: 25) | GGYLWN (SEQ ID NO: 26) | YISYDGTNNYKPSL KD (SEQ ID NO: 27) | YGRVFFDY (SEQ ID NO: 28) |

-continued

| Ab ID No | LCDR1 | LCDR2 | LCDR3 | HCDR1 | HCDR2 | HCDR3 |
|---|---|---|---|---|---|---|
| VRDN-02200 | QGDSLR SYYAT (SEQ ID NO: 29) | GENKRPS (SEQ ID NO: 30) | KSRDGSGQHL V (SEQ ID NO: 31) | SYAIS (SEQ ID NO: 32) | GIIPIFGTANYAQK FQG (SEQ ID NO: 33) | APLRFLEWST QDHYYYYMD V (SEQ ID NO: 34) |
| VRDN-02300 | RASQGI RNDLG (SEQ ID NO: 35) | AASRLHR (SEQ ID NO: 36) | LQHNSYPCS (SEQ ID NO: 37) | SYAMN (SEQ ID NO: 38) | AISGSGGTTFYADS VKG (SEQ ID NO: 39) | DLGWSDSYYY YYGMDV (SEQ ID NO: 40) |
| VRDN-02400 | RSSQSL LHSNGY NYLD (SEQ ID NO: 41) | LGSNRA (SEQ ID NO: 42) | MQGTHWPLT (SEQ ID NO: 43) | SSSNWWS (SEQ ID NO: 44) | EIYHSGSTNYNPSL KS (SEQ ID NO: 45) | WTGRTDAFDI (SEQ ID NO: 46) |
| VRDN-02500 | RASQSI GSSLH (SEQ ID NO: 47) | YASQSLS (SEQ ID NO: 48) | HQSSRLPHT (SEQ ID NO: 49) | SFAMH (SEQ ID NO: 50) | VIDTRGATYYADSV KG (SEQ ID NO: 51) | LGNFYYGMDV (SEQ ID NO: 52) |
| VRDN-1100/1100A/1100B | RSSQSI VHSNVN TYLE (SEQ ID NO: 53) | KVSNRFS (SEQ ID NO: 54) | FQGSHVPPT (SEQ ID NO: 55) | SYWMH (SEQ ID NO: 56) | GEINPSNGRTNYNQ KFQG (SEQ ID NO: 57) | GRPDYYGSSK WYFDV (SEQ ID NO: 58) |
| VRDN-2600 | QASRDI RNYLN (SEQ ID NO: 59) | DASSLQT (SEQ ID NO: 60) | QQFDSLPHT (SEQ ID NO: 61) | IYRMQ (SEQ ID NO: 62) | GISPSGGTTWYADS VK (SEQ ID NO: 63) | WSGGSGYAFD I (SEQ ID NO: 64) |
| VRDN-2301 | RASQGI RNDLG (SEQ ID NO: 35) | AASRLHR (SEQ ID NO: 36) | LQHNSYPSS (SEQ ID NO: 81) | SYAMN (SEQ ID NO: 38) | AISGSGGTTFYADS VKG (SEQ ID NO: 39) | DLGWSDSYYY YYGMDV (SEQ ID NO: 40) |

In some embodiments, an antibody, or antibody binding fragment thereof, comprises a heavy or light chain CDR having a sequence of SEQ ID NOs: 17-64 and 81. In some embodiments, an antibody, or antibody binding fragment thereof, comprises a light chain CDR having a sequence of SEQ ID NO: 17, 18, 19, 23, 24, 25, 29, 30, 31, 35, 36, 37, 41, 42, 43, 47, 48, 49, 53, 54, 55, 59, 60, 61, or 81. In some embodiments, an antibody, or antibody binding fragment thereof, comprises a heavy chain CDR having a sequence of SEQ ID NO: 20, 21, 22, 26, 27, 28, 32, 33, 34, 38, 39, 40, 44, 45, 46, 50, 51, 52, 56, 57, 58, 62, 63, or 64.

In some embodiments, an antibody, or antibody binding fragment thereof, comprises a light chain having a LCDR1, a LCDR2, and a LCDR3, wherein the LCDR1 has a sequence of SEQ ID NO: 17, 23, 29, 35, 41, 47, 53, or 59 the LCDR2 has a sequence of SEQ ID NO: 18, 24, 30, 36, 42, 48, 54, or 60 and the LCDR3 has a sequence of SEQ ID NO: 19, 25, 31, 37, 43, 49, 55, 61, or 81.

In some embodiments, an antibody, or antibody binding fragment thereof, comprises a heavy chain having a HCDR1, a HCDR2, and a HCDR3, wherein the HCDR1 has a sequence of SEQ ID NO: 20, 26, 32, 38, 44, 50, 56, or 62 the HCDR2 has a sequence of SEQ ID NO: 21, 27, 33, 39, 45, 51, 57, or 63 and the HCDR3 has a sequence of SEQ ID NO: 22, 28, 34, 40, 46, 52, 58, or 64.

The different CDR motifs can be combined in any combination including those not depicted in the table above. For example, the following embodiments are provided as non-limiting examples of such combinations.

In some embodiments, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 17; the light chain CDR2 has the amino acid sequence of SEQ ID NO: 18; and the light chain CDR3 sequence has the amino acid sequence of SEQ ID NO: 19; and (ii) a heavy chain variable region comprising heavy chain CDR1, CDR2, and CDR3 sequences, wherein the heavy chain CDR1 sequence has the amino acid sequence of SEQ ID NO: 20; the heavy chain CDR2 sequence has the amino acid sequence of SEQ ID NO: 21; and the heavy chain CDR3 sequence has the amino acid sequence of SEQ ID NO: 22; or variants of any of the foregoing.

In some embodiments, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 23; the light chain CDR2 has the amino acid sequence of SEQ ID NO: 24; and the light chain CDR3 sequence has the amino acid sequence of SEQ ID NO: 25; and (ii) a heavy chain variable region comprising heavy chain CDR1, CDR2, and CDR3 sequences, wherein the heavy chain CDR1 sequence has the amino acid sequence of SEQ ID NO: 26; the heavy chain CDR2 sequence has the amino acid sequence of SEQ ID NO: 27; and the heavy chain CDR3 sequence has the amino acid sequence of SEQ ID NO: 28; or variants of any of the foregoing.

In some embodiments, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 29; the light chain CDR2 has the amino acid sequence of SEQ ID NO: 30; and the light chain CDR3 sequence has the amino acid sequence of SEQ ID NO: 31; and (ii) a heavy chain variable region comprising heavy chain CDR1, CDR2, and CDR3 sequences, wherein the heavy chain CDR1 sequence has the amino acid sequence of SEQ ID NO: 32; the heavy chain CDR2 sequence has the amino acid sequence of SEQ ID NO: 33; and the heavy chain CDR3 sequence has the amino acid sequence of SEQ ID NO: 34; or variants of any of the foregoing.

In some embodiments, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 35; the light chain CDR2 has the amino acid sequence of SEQ ID NO: 36; and the light chain CDR3 sequence has the amino acid sequence of SEQ ID NO: 37; and (ii) a heavy chain variable region comprising heavy chain CDR1, CDR2, and CDR3 sequences, wherein the heavy chain CDR1 sequence has the amino acid sequence of SEQ ID NO: 38; the heavy chain CDR2 sequence has the amino acid sequence of SEQ ID NO: 39; and the heavy chain CDR3 sequence has the amino acid sequence of SEQ ID NO: 40; or variants of any of the foregoing.

In some embodiments, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 41; the light chain CDR2 has the amino acid sequence of SEQ ID NO: 42; and the light chain CDR3 sequence has the amino acid sequence of SEQ ID NO: 43; and (ii) a heavy chain variable region comprising heavy chain CDR1, CDR2, and CDR3 sequences, wherein the heavy chain CDR1 sequence has the amino acid sequence of SEQ ID NO: 44; the heavy chain CDR2 sequence has the amino acid sequence of SEQ ID NO: 45; and the heavy chain CDR3 sequence has the amino acid sequence of SEQ ID NO: 46; or variants of any of the foregoing.

In some embodiments, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 47; the light chain CDR2 has the amino acid sequence of SEQ ID NO: 48; and the light chain CDR3 sequence has the amino acid sequence of SEQ ID NO: 49; and (ii) a heavy chain variable region comprising heavy chain CDR1, CDR2, and CDR3 sequences, wherein the heavy chain CDR1 sequence has the amino acid sequence of SEQ ID NO: 50; the heavy chain CDR2 sequence has the amino acid sequence of SEQ ID NO: 51; and the heavy chain CDR3 sequence has the amino acid sequence of SEQ ID NO: 52; or variants of any of the foregoing.

In some embodiments, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 53; the light chain CDR2 has the amino acid sequence of SEQ ID NO: 54; and the light chain CDR3 sequence has the amino acid sequence of SEQ ID NO: 55; and (ii) a heavy chain variable region comprising heavy chain CDR1, CDR2, and CDR3 sequences, wherein the heavy chain CDR1 sequence has the amino acid sequence of SEQ ID NO: 56; the heavy chain CDR2 sequence has the amino acid sequence of SEQ ID NO: 57; and the heavy chain CDR3 sequence has the amino acid sequence of SEQ ID NO: 58; or variants of any of the foregoing.

In some embodiments, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 59; the light chain CDR2 has the amino acid sequence of SEQ ID NO: 60; and the light chain CDR3 sequence has the amino acid sequence of SEQ ID NO: 61; and (ii) a heavy chain variable region comprising heavy chain CDR1, CDR2, and CDR3 sequences, wherein the heavy chain CDR1 sequence has the amino acid sequence of SEQ ID NO: 62; the heavy chain CDR2 sequence has the amino acid sequence of SEQ ID NO: 63; and the heavy chain CDR3 sequence has the amino acid sequence of SEQ ID NO: 64; or variants of any of the foregoing.

In some embodiments, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 35; the light chain CDR2 has the amino acid sequence of SEQ ID NO: 36; and the light chain CDR3 sequence has the amino acid sequence of SEQ ID NO: 81; and (ii) a heavy chain variable region comprising heavy chain CDR1, CDR2, and CDR3 sequences, wherein the heavy chain CDR1 sequence has the amino acid sequence of SEQ ID NO: 38; the heavy chain CDR2 sequence has the amino acid sequence of SEQ ID NO: 39; and the heavy chain CDR3 sequence has the amino acid sequence of SEQ ID NO: 40; or variants of any of the foregoing.

In some embodiments, the light chain variable region CDR1 is replaced with any of the other light chain CDR1 sequences. In some embodiments, the light chain variable region CDR2 is replaced with any of the other light chain CDR2 sequences. In some embodiments, the light chain variable region CDR3 is replaced with any of the other light chain CDR3 sequences. In some embodiments, the heavy chain variable region CDR1 is replaced with any of the other light chain CDR1 sequences. In some embodiments, the heavy chain variable region CDR2 is replaced with any of the other light chain CDR2 sequences. In some embodiments, the heavy chain variable region CDR3 is replaced with any of the other light chain CDR3 sequences.

In some embodiments, the antibody, or antigen binding fragment thereof, or protein is provided that comprises a peptide having a sequence as set forth in any of SEQ ID NOs: 1, 3, 5, 7, 9, 11, 13, 15, 79, or 86, and 2, 4, 6, 8, 10, 12, 14, 16, 80, or 83.

In some embodiments, the antibody, or antigen binding fragment thereof, comprises a sequence of, or a variant of any of the foregoing.

In some embodiments, the antibody, or antigen binding fragment thereof, comprises a sequence of SEQ ID NOs: 65, or a variant of any of the foregoing. In some embodiments, the antibody, or antigen binding fragment thereof, comprises a sequence of SEQ ID NOs: 66, or a variant of any of the foregoing. In some embodiments, the antibody, or antigen binding fragment thereof, comprises a sequence of SEQ ID NOs: 67, or a variant of any of the foregoing. In some embodiments, the antibody, or antigen binding fragment thereof, comprises a sequence of SEQ ID NOs: 68, or a variant of any of the foregoing. In some embodiments, the antibody, or antigen binding fragment thereof, comprises a sequence of SEQ ID NOs: 69, or a variant of any of the foregoing. In some embodiments, the antibody, or antigen binding fragment thereof, comprises a sequence of SEQ ID NOs: 70, or a variant of any of the foregoing. In some embodiments, the antibody, or antigen binding fragment thereof, comprises a sequence of SEQ ID NOs: 71, or a variant of any of the foregoing. In some embodiments, the antibody, or antigen binding fragment thereof, comprises a sequence of SEQ ID NOs: 72, or a variant of any of the foregoing. In some embodiments, the antibody, or antigen binding fragment thereof, comprises a sequence of SEQ ID NOs: 78, or a variant of any of the foregoing. In some embodiments, the antibody, or antigen binding fragment thereof, comprises a sequence of SEQ ID NOs: 82, or a variant of any of the foregoing. In some embodiments, the antibody, or antigen binding fragment thereof, comprises a sequence of SEQ ID NOs: 85, or a variant of any of the foregoing.

In some embodiment, the $V_L$ and/or $V_H$ sequences are as provided herein. In some embodiments, the $V_L$ sequences are provided as elements of the light chain (LC). In some embodiments, the $V_L$ sequences that are provided as elements of the light chain (LC) are underlined in the LC sequence. In some embodiments, the $V_H$ sequences that are provided as elements of the heavy chain (LC) are underlined in the HC sequence.

In some embodiments, an antibody, or antigen binding fragment thereof, comprises a $V_L$ peptide as set forth in SEQ ID NOs: 1, 3, 5, 7, 9, 11, 13, 15, 79, or 86, or any combination thereof. The $V_L$ peptide can comprise a variant of any of these sequences as provided for herein.

In some embodiments, an antibody, or antigen binding fragment thereof, comprises a $V_H$ peptide as set forth in SEQ ID NOs: 2, 4, 6, 8, 10, 12, 14, 16, 80, or 83, or any combination thereof. The $V_H$ peptide can comprise a variant of any of these sequences as provided for herein.

In some embodiments, an antibody, or antigen binding fragment thereof, comprises a $V_H$ peptide and a $V_L$ peptide, wherein the wherein the $V_H$ peptide comprises a sequence as set forth in SEQ ID NO: 2, 4, 6, 8, 10, 12, 14, 16, 80, or 83 and the $V_L$ peptide comprises a sequence as set forth in SEQ ID NO: 1, 3, 5, 7, 9, 11, 13, 15, 79, or 86.

In some embodiments, an antibody, or antigen binding fragment thereof, comprises a $V_H$ peptide and a $V_L$ peptide, wherein the $V_H$ peptide comprises a sequence as set forth in SEQ ID NO: 2 and the $V_L$ peptide comprises a sequence as set forth in SEQ ID NO: 1. In some embodiments, an antibody, or antigen binding fragment thereof, comprises a $V_H$ peptide and a $V_L$ peptide, wherein the $V_H$ peptide comprises a sequence as set forth in SEQ ID NO: 4 and the $V_L$ peptide comprises a sequence as set forth in SEQ ID NO: 3. In some embodiments, an antibody, or antigen binding fragment thereof, comprises a $V_H$ peptide and a $V_L$ peptide, wherein the $V_H$ peptide comprises a sequence as set forth in SEQ ID NO: 6 and the $V_L$ peptide comprises a sequence as set forth in SEQ ID NO: 5. In some embodiments, an antibody, or antigen binding fragment thereof, comprises a $V_H$ peptide and a $V_L$ peptide, wherein the $V_H$ peptide comprises a sequence as set forth in SEQ ID NO: 8 and the $V_L$ peptide comprises a sequence as set forth in SEQ ID NO: 7. In some embodiments, an antibody, or antigen binding fragment thereof, comprises a $V_H$ peptide and a $V_L$ peptide, wherein the $V_H$ peptide comprises a sequence as set forth in SEQ ID NO: 10 and the $V_L$ peptide comprises a sequence as set forth in SEQ ID NO: 9. In some embodiments, an antibody, or antigen binding fragment thereof, comprises a $V_H$ peptide and a $V_L$ peptide, wherein the $V_H$ peptide comprises a sequence as set forth in SEQ ID NO: 12 and the $V_L$ peptide comprises a sequence as set forth in SEQ ID NO: 11. In some embodiments, an antibody, or antigen binding fragment thereof, comprises a $V_H$ peptide and a $V_L$ peptide, wherein the $V_H$ peptide comprises a sequence as set forth in SEQ ID NO: 14 and the $V_L$ peptide comprises a sequence as set forth in SEQ ID NO: 13. In some embodiments, an antibody, or antigen binding fragment thereof, comprises a $V_H$ peptide and a $V_L$ peptide, wherein the $V_H$ peptide comprises a sequence as set forth in SEQ ID NO: 16 and the $V_L$ peptide comprises a sequence as set forth in SEQ ID NO: 15. In some embodiments, an antibody, or antigen binding fragment thereof, comprises a $V_H$ peptide and a $V_L$ peptide, wherein the $V_H$ peptide comprises a sequence as set forth in SEQ ID NO: 80 and the $V_L$ peptide comprises a sequence as set forth in SEQ ID NO: 79. In some embodiments, an antibody, or antigen binding fragment thereof, comprises a $V_H$ peptide and a $V_L$ peptide, wherein the $V_H$ peptide comprises a sequence as set forth in SEQ ID NO: 83 and the $V_L$ peptide comprises a sequence as set forth in SEQ ID NO: 3. In some embodiments, an antibody, or antigen binding fragment thereof, comprises a $V_H$ peptide and a $V_L$ peptide, wherein the $V_H$ peptide comprises a sequence as set forth in SEQ ID NO: 14 and the $V_L$ peptide comprises a sequence as set forth in SEQ ID NO: 86.

In some embodiments, an antibody, or antigen binding fragment thereof, comprises a LC peptide as set forth in SEQ ID NOs: 1, 3, 5, 7, 9, or 11, or any combination thereof. The LC peptide can comprise a variant of any of these sequences as provided for herein.

In some embodiments, an antibody, or antigen binding fragment thereof, comprises a HC peptide as set forth in SEQ ID NOs: 2, 4, 6, 8, 10, 12, or 83, or any combination thereof. The HC peptide can comprise a variant of any of these sequences as provided for herein.

In some embodiments, an antibody, or antigen binding fragment thereof, comprises a HC peptide and a LC peptide, wherein the wherein the HC peptide comprises a sequence as set forth in SEQ ID NO: 2, 4, 6, 8, 10, 12, or 83 and the LC peptide comprises a sequence as set forth in SEQ ID NO: 1, 3, 5, 7, 9, or 11. In some embodiments, an antibody, or antigen binding fragment thereof, comprises a HC peptide and a LC peptide, wherein the HC peptide comprises a sequence as set forth in SEQ ID NO: 2 and the LC peptide comprises a sequence as set forth in SEQ ID NO: 1. In some embodiments, an antibody, or antigen binding fragment thereof, comprises a HC peptide and a LC peptide, wherein the HC peptide comprises a sequence as set forth in SEQ ID NO: 4 and the LC peptide comprises a sequence as set forth in SEQ ID NO: 3. In some embodiments, the HC peptide comprising the sequence as set forth in SEQ ID NO: 4 has an additional C terminal lysine (K) residue. In some embodiments, an antibody, or antigen binding fragment thereof, comprises a HC peptide and a LC peptide, wherein the HC peptide comprises a sequence as set forth in SEQ ID NO: 6 and the LC peptide comprises a sequence as set forth in SEQ ID NO: 5. In some embodiments, an antibody, or antigen binding fragment thereof, comprises a HC peptide and a LC peptide, wherein the HC peptide comprises a sequence as set forth in SEQ ID NO: 8 and the LC peptide comprises a sequence as set forth in SEQ ID NO: 7. In some embodiments, an antibody, or antigen binding fragment thereof, comprises a HC peptide and a LC peptide, wherein the HC peptide comprises a sequence as set forth in SEQ ID NO: 10 and the LC peptide comprises a sequence as set forth in SEQ ID NO: 9. In some embodiments, an antibody, or antigen binding fragment thereof, comprises a HC peptide and a LC peptide, wherein the HC peptide comprises a sequence as set forth in SEQ ID NO: 12 and the LC peptide comprises a sequence as set forth in SEQ ID NO: 11. In some embodiments, an antibody, or antigen binding fragment thereof, comprises a HC peptide and a LC peptide, wherein the HC peptide comprises a sequence as set forth in SEQ ID NO: 83 and the LC peptide comprises a sequence as set forth in SEQ ID NO: 3.

In addition to these specific combinations any of the $V_H$ peptides and the $V_L$ peptides can be combined with one another.

In addition to these specific combinations any of the HC peptides and the LC peptides can be combined with one another.

In some embodiments, the antibody comprises a sequence, or antigen binding fragment of ATCC® clone PTA-7444. The sequence of the antibody produced by ATCC® clone PTA-7444 is hereby incorporated by reference in its entirety, which includes the antigen binding fragments thereof.

Additionally, as provided for herein, the antibodies can be multi-specific antibodies, in that the antibodies have multiple binding regions that target different proteins or the same protein at different epitopes. In some embodiments, the antibody is a bi-specific antibody.

As provided for herein, the different peptides ($V_H$ or $V_L$) described herein can be linked with a peptide linker or not linked with a peptide linker and instead for a contiguous sequence. In some embodiments, the peptide linker comprises a sequence of: (GGGGS)$_n$ (SEQ ID NO: 73); (GGGGA)$_n$ (SEQ ID NO: 74), or any combination thereof, wherein each n is independently 1-5. The linked peptide format can be represented by a formula of $V_H$-Z-$V_L$ or $V_L$-Z-$V_H$, wherein Z is the peptide linker. In some embodiments, Z is (GGGGS)$_n$ (SEQ ID NO: 73); (GGGGA)$_n$ (SEQ ID NO: 74), or any combination thereof, wherein each n is independently 1-5.

As provided for herein, the antibodies, or antigen binding fragments thereof can be variants of the sequences.

Other examples of antibodies include, but are not limited to, those provided in US20160096894A1, EP1399483B1, EP2194067B1, US20040202651A1, US20110229933A1, U.S. Pat. No. 8,137,933B2, U.S. Pat. No. 8,951,790B2, US20190270820A1, U.S. Pat. No. 7,572,897B2, US20090275126A1, EP1959014B1, US20080014203A1, US20080226635A1, US20120076778A1, US20190153071A1, WO2011161119A1, U.S. Ser. No. 10/611,825B2, US20120237507A1, EP2681240B1, U.S. Pat. No. 9,982,036B2, US20180312573A1, EP2681239B1, US20160151487A1, US20190225696A1, WO2017011773A2, US20200023076A1, US20190153471A1, US20190194713A1, WO2020006486A1, US20080112888A1, US20150168424A1, EP2032989B2, U.S. Pat. No. 9,045,536B2, each of which is hereby incorporated by reference in its entirety. Other examples of antibodies include, but are not limited to, those provided in U.S. Pat. No. 8,153,121B2, EP1469879B1, WO2016064716A1, US20190270820A1, US20180280527A1, US20190225696A1, U.S. Pat. No. 7,998,681B2, US20040202651A1, US20050136063A1, US20090285824A1, US20150274829A1, EP2322550B1, US20060286103A1, US20070071675A1, US20100047239A1, US20130004416A1, US20080112888A1, US20150168424A1, US20100143340A1, US20110014117A1, US20100260668A1, US20100074900A1, US20150017168A1, US20110044980A1, US20130330323A1, US20120263722A1, US20120201746A1, U.S. Ser. No. 10/519,245B2, US20180243432A1, US20170218091A1, US20200115460A1, US20100104645A1, US20120065380A1, EP2970433B1, US20160289341A1, US20160289343A1, US20190293656A1, each of which is hereby incorporated by reference in its entirety.

In some embodiments, the antibody comprises a heavy and a light chain, wherein the heavy chain comprises a sequence of:

```
                                        (SEQ ID NO: 92)
QVQLVQSGAEVVKPGASVKLSCKASGYTFTSYWMHWVKQRPGQGLEWIGE

INPSNGRTNYNQKFQGKATLTVDKSSSTAYMQLSSLTSEDSAVYYFARGR

PDYYGSSKWYFDVWGQGTTVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSL

SPGK;
``` and the light chain comprises a sequence of:

```
                                        (SEQ ID NO: 93)
DVVMTQTPLSLPVSLGDPASISCRSSQSIVHSNVNTYLEWYLQKPGQSPR

LLIYKVSNRFSGVPDRFSGSGAGTDFTLRISRVEAEDLGIYYCFQGSHVP

PTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.
```

In some embodiments, the antibody comprises a heavy and a light chain, wherein the heavy chain comprises a sequence of:

```
                                        (SEQ ID NO: 94)
QVQLVQSGAEVVKPGASVKLSCKASGYTFTSYWMHWVKQRPGQGLEWIGE

INPSNGRTNYNQKFQGKATLTVDKSSSTAYMQLSSLTSEDSAVYYFARGR

PDYYGSSKWYFDVWGQGTTVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLF
```

-continued
PPKPKDTLYITREPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSL

SPG;

and the light chain comprises a sequence of (SEQ ID NO: 93)
DVVMTQTPLSLPVSLGDPASISCRSSQSIVHSNVNTYLEWYLQKPGQSPR

LLIYKVSNRFSGVPDRFSGSGAGTDFTLRISRVEAEDLGIYYCFQGSHVP

PTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

In some embodiments, the heavy chain of SEQ ID NO: 94 comprises a C-terminal lysine residue that is added to the C-terminus of SEQ ID NO: 94.

In some embodiments, the antibody comprises a heavy and a light chain, wherein the heavy chain comprises a sequence of:

(SEQ ID NO: 95)
QVQLVQSGAEVVKPGASVKLSSKASGYTFTSYWMHWVKQRPGQGLEWIGE

INPSNGRTNYNQKFQGKATLTVDKSSSTAYMQLSSLTSEDSAVYYFARGR

PDYYGSSKWYFDVWGQGTTVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLF

PPKPKDTLYITREPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSL

SPG;

and the light chain comprises a sequence of SEQ ID NO: 93

In some embodiments, the heavy chain of SEQ ID NO: 95 comprises a C-terminal lysine residue that is added to the C-terminus of SEQ ID NO: 95.

In some embodiments, the antibody comprises a heavy chain and light chain, wherein the heavy chain comprises a sequence of SEQ ID NO: 83 and the and the light chain comprises a sequence of SEQ ID NO: 3.

In some embodiments, the antibody comprises a VH sequence of SEQ ID NO: 96 and a VL sequence of SEQ ID NO: 13 or SEQ ID NO: 97. In some embodiments, the antibody comprises a VH of SEQ ID NO: 14 and a VL sequence of SEQ ID NO: 97.

Pharmaceutical Compositions

In some embodiments, to prepare pharmaceutical or sterile compositions of the anti-IGF-1R antibodies or other proteins provided herein, the antibody or antigen binding fragment thereof or other proteins provided herein are admixed with a pharmaceutically acceptable carrier or excipient. See, e.g., *Remington's Pharmaceutical Sciences* and U.S. Pharmacopeia: National Formulary, Mack Publishing Company, Easton, PA (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, NY; Gennaro (2000) *Remington: The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY). In some embodiments embodiment, the antibodies are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In some embodiments, a composition of the invention is administered to a subject in accordance with the Physicians' Desk Reference 2003 (Thomson Healthcare; 57th edition (Nov. 1, 2002)).

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In some embodiments, the antibody or antigen binding fragment thereof can be administered by an invasive route such as by injection. In some embodiments, the antibodies or antigen binding fragment thereof, or pharmaceutical composition thereof, is administered intravenously, subcutaneously, intramuscularly, intraarterially, intra-articularly (e.g. in arthritis joints), or by inhalation, aerosol delivery. Administration by non-invasive routes (e.g., orally; for example, in a pill, capsule or tablet) is also within the scope of the present embodiments.

In some embodiments, the antibody or antigen binding fragment thereof can be administered directly to the eye, the anterior chamber of the eye, the vitreous chamber of the eye, the suprachoroidal space, or the retro-orbital sinus. In some embodiments, administration to the eye, the anterior chamber of the eye, the vitreous chamber of the eye, the suprachoroidal space, or the retro-orbital sinus is via an injection. In some embodiments, the injection is an intravitreal injection, intraorbital injection, retro-orbital injection, suprachoroidal injection, or intracameral injection. In some embodiments, the injection is an intravitreal injection. In some embodiments, the injection is an, intraorbital injection. In some embodiments, the injection is a retro-orbital injection. In some embodiments, the injection is a suprachoroidal injection. In some embodiments, the injection is an intracameral injection.

In some embodiments, the anti-IGF-1R antibody, or antigen binding fragment thereof, is administered in combination with at least one additional therapeutic agent, such as, but not limited to any therapeutic used to treat thyroid eye disease. For example, in some embodiments, the anti-IGF-1R antibody, or antigen binding fragment thereof, is administered in combination with at least one additional therapeutic agent, such as, but not limited to a therapeutic used to treat thyroid eye disease or a condition related to the same. Examples of such treatments and therapeutics include, but are not limited to anti-thyroid medications, diabetes medications, beta-blockers, propylthiouracil, methimazole, propranolol, atenolol, metoprolol, nadolol, corticosteroids, metformin, sulfonylureas, meglitinides, thiazolidinediones, DPP-4 inhibitors, GLP-1 receptor agonists, SGLT2 inhibitors, regular insulin, insulin aspart, insulin glulisine, insulin lispro, insulin isophane, insulin degludec, insulin detemir, insulin glargine, acerbose, miglitol, acebutolol, atenolol, betaxolol, bisoprolol, cartelol, carvedilol, esmolol, labetalol, metoprolol, nadolol, nebivolol, penbutolol, pindolol, propranolol, sotalol, timolol, tomolol ophthalmic solution, sitagliptin, saxagliptin, linagliptin, alogliptin, dulaglutide, exenatide, semaglutide, liraglutide, lixisenatide, canagliflozin, dapagliflozin, empagliflozin, or any combination thereof.

Compositions can be administered with medical devices known in the art. For example, a pharmaceutical composition of the invention can be administered by injection with a hypodermic needle, including, e.g., a prefilled syringe or autoinjector.

The pharmaceutical compositions may also be administered with a needleless hypodermic injection device; such as the devices disclosed in U.S. Pat. Nos. 6,620,135; 6,096, 002; 5,399,163; 5,383,851; 5,312,335; 5,064,413; 4,941, 880; 4,790,824 or 4,596,556.

The pharmaceutical compositions may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multichamber compartments. Many other such implants, delivery systems, and modules are well known to those skilled in the art.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antibodies are may be desirable.

Antibodies or antigen binding fragments thereof can be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. In some embodiments, the antibody is administered every three weeks, every four weeks, every five weeks, every six weeks, every seven weeks, or every eight weeks. In some embodiments, the antibody is administered every four weeks. In some embodiments, the antibody is administered every five weeks. In some embodiments, the antibody is administered every seven weeks. In some embodiments, the antibody is administered every six weeks. In some embodiments, the antibody is administered every eight weeks. In some embodiments, the antibody is administered for at least 21-52 weeks or longer. In some embodiments, the antibody is administered on such a schedule for at least 21 weeks. In some embodiments, the antibody is administered on such a schedule for at least 24 weeks. In some embodiments, the antibody is administered on such a schedule for at least 32 weeks. In some embodiments, the antibody is administered on such a schedule for at least 36 weeks. In some embodiments, the antibody is administered on such a schedule for at least 40 weeks. In some embodiments, the antibody is administered on such a schedule for at least 42 weeks. In some embodiments, the antibody is administered (e.g. infusion or subcutaneous injection) once. In some embodiments, the antibody is administered (e.g. infusion or subcutaneous injection) twice. In some embodiments, the antibody is administered (e.g. infusion or subcutaneous injection) three times. In some embodiments, the antibody is administered (e.g. infusion or subcutaneous injection) four times. In some embodiments, the antibody is administered (e.g. infusion or subcutaneous injection) five times. In some embodiments, the antibody is administered (e.g. infusion or subcutaneous injection) six times. In some embodiments, the antibody is administered (e.g. infusion or subcutaneous injection) seven times. In some embodiments, the antibody is administered (e.g. infusion or subcutaneous injection) eight times. In some embodiments, the antibody is administered (e.g. infusion or subcutaneous injection) nine times. In some embodiments, the antibody is administered (e.g. infusion or subcutaneous injection) 10 times. In some embodiments, the antibody is administered (e.g. infusion or subcutaneous injection) 11 times. In some embodiments, the antibody is administered (e.g. infusion or subcutaneous injection) 12 times. In some embodiments, the antibody is administered (e.g. infusion or subcutaneous injection) 13 times. In some embodiments, the antibody is administered (e.g. infusion or subcutaneous injection) 14 times. In some embodiments, the antibody is administered (e.g. infusion or subcutaneous injection) 15 times. In some embodiments, the antibody is administered (e.g. infusion or subcutaneous injection) 16 times. In some embodiments, the antibody is administered (e.g. infusion or subcutaneous injection) 17 times. In some embodiments, the antibody is administered (e.g. infusion or subcutaneous injection) 18 times. In some embodiments, the antibody is administered (e.g. infusion or subcutaneous injection) 19 times. In some embodiments, the antibody is administered (e.g. infusion or subcutaneous injection) 20 times. When the antibody is administered more than once it can be administered according to a schedule, such as the schedules provided for herein.

A total weekly dose can be as provided for herein. In some embodiments, the total weekly dose is at least 0.05 µg/kg body weight, more generally at least 0.2 µg/kg, 0.5 µg/kg, 1 µg/kg, 10 µg/kg, 100 ag/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) New Engl. J. Med. 349:427-434; Herold, et al. (2002) New Engl. J. Med. 346:1692-1698; Liu, et al. (1999) J. Neurol. Neurosurg. Psych. 67:451-456; Portielji, et al. (20003) Cancer Immunol. Immunother. 52:133-144). Doses may also be provided to achieve a predetermined target concentration of the antibody in the subject's serum, such as 0.1, 0.3, 1, 3, 10, 30, 100, 300 µg/ml or more.

In some embodiments, the antibody has a serum concentration in the subject of at least, or about, 10 µg/ml or 20 µg/ml or 50 µg/ml, 70 µg/ml, 75 µg/ml, 80 µg/ml, 85 µg/ml, 90 µg/ml, 95 µg/ml, 100 µg/ml, or 105 µg/ml at least 1, 2, or 3 weeks after administration.

In some embodiments, a dose of 20 mg/kg IV is administered In some embodiments, a dosing is used to provide a Cmin of 133 µg/mL after about 5 weeks. In some embodiments, the dose of the antibody that is administered that provides a Cmin of 102 µg/mL after 6 weeks. In some embodiments, the dose of the antibody is as provided for herein, such as 10 mg/mg as a loading dose with subsequent doses being the same or lower. In some embodiments, the antibody is administered as provided for herein at a dose to achieve a Cmin of at least, or about, 100 µg/mL.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of the antibody, or antigen binding fragment thereof, that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity. In some embodiments, an amount is a therapeutically effective amount if it is an amount that can be used to treat or ameliorate a condition as provided for herein.

The term "subject" as used throughout includes any organism, such as an animal, including a mammal (e.g., rat, mouse, dog, cat, rabbit) and, for example, a human. A subject can be also be referred to as a patient. In some embodiments, the subject is a subject in need thereof. A subject that is "in need thereof" refers to a subject that has been identified as requiring treatment for the condition that is to be treated and is treated with the specific intent of treating such condition. The conditions can be, for example, any of the conditions described herein.

Whereas, an isolated antibody binds an epitope on a IGF-1R protein, or other protein described herein, and displays in vitro and/or in vivo IGF-1R inhibiting or therapeutic activities, the antibodies or antigen binding fragments thereof, capable of inhibiting IGF-1R function, are suitable both as therapeutic agents for treating IGF-1R-associated conditions in humans and animals. These conditions include thyroid eye disease. According, methods of treating such conditions are also provided, wherein the method comprises administering an antibody, or antigen binding fragment thereof, to the subject with such a condition.

In some embodiments, the methods comprise administering a therapeutically or prophylactically effective amount of one or more monoclonal antibodies or antigen binding fragments of the antibodies described herein to a susceptible subject or to one exhibiting a condition in which IGF-1R is known or suspected to have caused the pathology observed.

Any active form of the antibody can be administered, including, but not limited to scFV, Fab and F(ab')2 fragments and other forms of antibodies provided for herein.

As used herein, a IGF-1R associated pathology refers to conditions that are caused by the modulation of IGF-1R. These conditions include, but are not limited to, thyroid eye disease and other conditions provided for herein.

In some embodiments, the antibodies used are compatible with the recipient species such that the immune response to the MAbs does not result in an unacceptably short circulating half-life or induce an immune response to the MAbs in the subject.

Treatment of individuals may comprise the administration of a therapeutically effective amount of the antibodies described herein. The antibodies can be provided in a kit, such as those provided herein. The antibodies can be used or administered alone or in admixture with another therapeutic, analgesic, or diagnostic agent, such as provided for herein. In providing a patient with an antibody, or fragment thereof, capable of binding to IGF-1R, or an antibody capable of protecting against IGF-1R, pathology in a recipient patient, the dosage of administered agent will vary depending upon such factors as the patient's age, weight, height, sex, general medical condition, previous medical history, etc.

An antibody, capable treating a condition associated with IGF-1R activity or use to treat a IGF-1R related pathology, is intended to be provided to subjects in an amount sufficient to affect a reduction, resolution, or amelioration in the IGF-1R related symptom or pathology. Such a pathology includes, thyroid eye disease and the like Accordingly, in some embodiments, methods of treating a subject with a IGF-1R mediated disorder are provided. In some embodiments, the method comprises administering a pharmaceutical composition comprising an antibody, or antigen binding fragment thereof, as provided herein. In some embodiments, the disorder is thyroid eye disease. As provided for herein, the antibodies, or antigen binding fragments thereof, can be administered with other therapeutics. These can be administered simultaneously or sequentially.

In some embodiments, the antibodies, or antigen binding fragments thereof, may be used to treat thyroid eye disease. In some embodiments, the antibodies, or antigen binding fragments thereof, may be used to treating or reduce the severity of, thyroid-associated ophthalmopathy (TAO), or a symptom thereof.

In some embodiments, methods or uses are provided to reduce proptosis in an eye in a subject with thyroid-associated ophthalmopathy (TAO).

In some embodiments, the subject is a subject how has previously been treated with a different antibody than those provided herein.

In some embodiments, methods or uses are provided to Clinical Activity Score (CAS) in subject who has or is suspected of having thyroid-associated ophthalmopathy (TAO).

In some embodiments, methods or uses are provided to reduce proptosis by at least 2 mm and b) reducing the clinical activity score (CAS) in a subject with thyroid-associated ophthalmopathy (TAO).

As used herein, the term Clinical Activity Score (CAS) refers to the protocol described and scored according to Table 2. According to this protocol, one point is given for the presence of each of the parameters assessed in the Table below. The sum of all points defines clinical activity and provides the CAS, where 0 or 1 constitutes inactive disease and 7 severe active ophthalmopathy.

TABLE 2

Parameters for calculating Clinical Activity Score

| Item No. | Parameter |
| --- | --- |
| 1 | Spontaneous retrobulbar pain |
| 2 | Pain on attempted eye movements (upward, side to side, and downward gazes; sometimes termed gaze evoked orbital pain |
| 3 | Eyelid swelling |
| 4 | Eyelid erythema (redness) |
| 5 | Conjunctival redness |
| 6 | Chemosis (swelling/edema of the conjunctiva) |
| 7 | Swelling of caruncle or pila |

As provided in Table 2, the CAS consists of seven components: spontaneous retrobulbar pain, pain on attempted eye movements (upward, side-to-side, and downward gazes), conjunctival redness, redness of the eyelids, chemosis, swelling of the caruncle/plica, and swelling of the eyelids. Each component is scored as present (1 point) or absent (0 points). The score at each efficacy assessment is the sum of all items present; giving a range of 0-7, where 0 or 1 constitutes inactive disease and 7 severe active ophthalmopathy. A change of >2 points is considered clinically meaningful.

Item 1, spontaneous orbital pain could be a painful, or oppressive feeling on, or behind, the globe. This pain may be caused by the rise in intraorbital pressure, when the orbital tissues volume increases through excess synthesis of extracellular matrix, fluid accumulation, and cellular infiltration and expansion. Item 2, gaze evoked orbital pain, could be pain in the eyes when looking, or attempting to look, up, down or sideways, i.e., pain with upward, downward, or lateral eye movement, or when attempting eye movement. This kind of pain could arise from the stretching of the inflamed muscle(s), especially on attempted upgaze. The 'stretching pain' cannot be provoked by digital pressing on the eyeball, as would be expected if it were a manifestation of the raised intraorbital pressure. Both kinds of pain can be reduced after anti-inflammatory treatment. These kinds of pain are therefore considered to be directly related to autoimmune inflammation in the orbit and thus useful in assessing TAO activity.

Swelling in TAO is seen as chemosis (edema of the conjunctiva), item no. 6 in Table 1, and swelling of the caruncle and/or plica semilunaris. Both are signs of TAO activity. Swollen eyelids can be caused by edema, fat prolapse through the orbital septum, or fibrotic degeneration. In addition to swelling, other symptoms indicative of active TAO include redness and/or pain of the conjunctiva, eyelid, caruncle and/or plica semilunaris.

In some embodiments, the subject who is treated has the proptosis is reduced by at least 2 mm. In some embodiments, the subject who is treated has the proptosis is reduced by at least 3 mm. In some embodiments, the subject who is treated has the proptosis is reduced by at least 4 mm.

In some embodiments, in the subjects who are treated the clinical activity score (CAS) of the subject is reduced by at least 2 points. In some embodiments, the clinical activity score (CAS) of the subject is reduced to one (1). In some embodiments, the clinical activity score (CAS) of the subject is reduced to zero (0).

In some embodiments, methods off treating or reducing the severity of thyroid-associated ophthalmopathy (TAO) in a subject are provided, wherein the treatment with said antibody (i) reduces proptosis by at least 2 mm in an eye; (ii)

is not accompanied by a deterioration of 2 mm or more in the other (or fellow eye); and (iii) reduces the CAS in said subject to either one (1) or zero (0).

In some embodiments, methods of improving the quality of life in a subject with thyroid-associated ophthalmopathy (TAO, also called Graves' Ophthalmopathy/Graves' Orbitopathy) are provided. In some embodiments, the quality of life is measured by the Graves' Ophthalmopathy Quality of Life (GO-QoL) assessment, or either the Visual Functioning or Appearance subscale thereof. In some embodiments, the treatment results in an improvement of greater than or equal to 8 points on the GO-QoL. In some embodiments, the treatment results in an improvement on the Functioning subscale of the GO-QoL. In some embodiments, the treatment results in an improvement on the Appearance subscale of the GO-QoL.

In some embodiments, methods of treating or reducing the severity of diplopia in a subject with thyroid-associated ophthalmopathy (TAO) are provided. In some embodiments, the diplopia is constant diplopia. In some embodiments, the diplopia is inconstant diplopia. In some embodiments, the diplopia is intermittent diplopia. In some embodiments, the improvement in or reduction in severity of diplopia is sustained at least 20 weeks after discontinuation of antibody administration. In some embodiments, the improvement in or reduction in severity of diplopia is sustained at least 50 weeks after discontinuation of antibody administration.

The severity of the disease can be measured in the following non-limiting embodiments. For example, for lid aperture, the distance between the lid margins are measured (in mm) with the patient looking in the primary position, sitting relaxed, and with distant fixation. For swelling of the eyelids, the measure/evaluation is either "absent/equivocal," "moderate," or "severe." Redness of the eyelids is either absent or present. Redness of the conjunctivae is either absent or present. In some embodiments, conjunctival edema is either absent or present. In some embodiments, inflammation of the caruncle or plica is either absent or present. Exophthalmos is measured in millimeter using the same Hertel exophthalmometer and same intercanthal distance for an individual patient. Subjective diplopia is scored from 0 to 3 (0=no diplopia; 1=intermittent, i.e., diplopia in primary position of gaze, when tired or when first awakening; 2=inconstant, i.e., diplopia at extremes of gaze; 3=constant, i.e., continuous diplopia in primary or reading position). For eye muscle involvement, the ductions are measured in degrees. Corneal involvement is either absent/punctate or keratopathy/ulcer. For optic nerve involvement, i.e., best-corrected visual acuity, color vision, optic disc, relative afferent pupillary defect, the condition is either absent or present. In addition, visual fields are checked if optic nerve compression is suspected. In some embodiments, the patient can be classified according to the following severity classification. For example, sight-Threatening Thyroid Eye Disease: Patients with dysthyroid optic neuropathy (DON) and/or corneal breakdown. This category warrants immediate intervention. Moderate-to-Severe Thyroid Eye Disease: Patients without sight-threatening disease whose eye disease have sufficient impact on daily life to justify the risks of immunosuppression (if active) or surgical intervention (if inactive). Patients with moderate-to-severe thyroid eye disease usually have any one or more of the following: lid retraction greater than or equal to 2 mm, moderate or severe soft tissue involvement, exophthalmos greater than or equal to 3 mm above normal for race and gender, inconstant or constant diplopia. Mild Thyroid Eye Disease: Patients whose features of thyroid eye disease have only a minor impact on daily life insufficient to justify immunosuppressive or surgical treatment. They usually have only one or more of the following: minor lid retraction (<2 mm), mild soft tissue involvement, exophthalmos<3 mm above normal for race and gender, transient or no diplopia, and corneal exposure responsive to lubricants.

In some embodiments, a patient can be characterized by Graves Ophthalmopathy Quality of Life (GO-QoL) score. In addition to proptosis (or exophthalmos) and CAS, quality of life is also evaluated with the use of the GO quality of life (GO-QoL) questionnaire. This questionnaire is designed to determine the improved quality of life after treatment with a method disclosed herein. In some embodiments, questionnaire may determine the decreased or lack of side effects after being treated with an antibody, or an antigen binding fragment thereof, according to a method disclosed herein as compared to treatment with glucocorticoids. The GO-QoL is a 16-item self-administered questionnaire divided into 2 subsets and used to assess the perceived effects of TED by the subjects on (i) their daily physical activity as it relates to visual function, and (ii) psychosocial functioning. Quality of life is evaluated with the use of the GO QoL questionnaire. The GO-QoL questionnaire [C. B. Terwee et al, is completed on Day 1 and Weeks 6, 12, and 24 (or PW) during the Treatment Period, and at Months 7 and 12 (or PW) during the Follow-Up Period. The GO-QoL is a 16-item self-administered questionnaire divided into two self-assessment subscales; one covering impact of visual function on daily activities, the other assesses the impact of self-perceived appearance. The visual function subscale covers activities such as driving, walking outdoors, reading, watching television. The appearance subscale asks the subject questions such as whether ophthalmopathy has altered the subject's appearance, caused other people to have a negative reaction to the subject, caused social isolation, and caused the subject to try to mask his or her appearance. Each subscale has 8 questions which are answered with: yes—very much so; yes—a little; or no—not at all. Each question is scored 0-2, respectively, and the total raw score is then mathematically transformed to a 0-100 scale, where 0 represents the most negative impact on quality of life, and 100 represents no impact. A change of > or greater than equal to 8 points on the 0-100 scale has been shown to be clinically meaningful. The combined score takes raw scores from both subscales and again transforms them to a single 0-100 scale. The questionnaire has two self-assessment subscales. Each subscale has 8 questions which are answered with: (i) yes—very much so; (ii) yes—a little; or (iii) no—not at all. Each question is scored 0-2, respectively, and the total raw score is then mathematically transformed to a 0-100 scale, where 0 represents the most negative impact on quality of life, and 100 represents no impact. A change of >8 points on the 0-100 scale is considered to be clinically meaningful. The combined score takes raw scores from both subscales and again transforms them to a single 0-100 scale.

Patients can also be assessed by the presence of absence of Gorman Grading of Diplopia. The Gorman assessment of subjective diplopia includes four categories: no diplopia (absent), diplopia when the patient is tired or awakening (intermittent), diplopia at extremes of gaze (inconstant), and continuous diplopia in the primary or reading position (constant). Patients are scored according to which grade of diplopia they are experiencing. An improvement of greater than equal or to 1 grade is considered clinically meaningful.

In some embodiments, the methods comprise administering an antibody, such as those provided herein. In some embodiments, the antibody is administered at a dosage of about 1 mg/kg to about 5 mg/kg antibody as a first dose. In some embodiments, the antibody is administered at a dosage of about 5 mg/kg to about 10 mg/kg antibody as a first dose. In some embodiments, the antibody is administered at a dosage of about 5 mg/kg to about 20 mg/kg antibody in subsequent doses. In some embodiments, the antibody is administered in the following amounts: about 10 mg/kg antibody as a first dose; and about 20 mg/kg antibody in subsequent doses. In some embodiments, the subsequent doses are administered every three weeks for at least 21 weeks.

In some embodiments, the antibody is administered in a pharmaceutical composition, such as those provided herein. In some embodiments, the pharmaceutical composition further comprises one or more pharmaceutically active compounds for the treatment of TAO. In some embodiments, the pharmaceutical composition further comprises corticosteroids; rituximab or other anti-CD20 antibodies; tocilizumab or other anti-IL-6 antibodies; or selenium, infliximab or other anti-TNFalpha antibodies or a thyroid-stimulating hormone receptor (TSHR) inhibitor.

In some embodiments, the method provided herein comprise administering to a subject an antibody, or an antigen binding fragment thereof, that specifically binds to and inhibits IGF-IR. In some embodiments, the antibody is as provided herein.

Kits are also provided which are useful for carrying out embodiments described herein. The present kits comprise a first container containing or packaged in association with the above-described antibodies. The kit may also comprise another container containing or packaged in association solutions necessary or convenient for carrying out the embodiments. The containers can be made of glass, plastic or foil and can be a vial, bottle, pouch, tube, bag, etc. The kit may also contain written information, such as procedures for carrying out the embodiments or analytical information, such as the amount of reagent contained in the first container means. The container may be in another container apparatus, e.g. a box or a bag, along with the written information.

Yet another aspect provided for herein is a kit for detecting IGF-1R protein in a biological sample. The kit includes a container holding one or more antibodies which binds an epitope of IGF-1R protein and instructions for using the antibody for the purpose of binding to IGF-1R protein to form an immunological complex and detecting the formation of the immunological complex such that the presence or absence of the immunological complex correlates with presence or absence of IGF-1R protein in the sample. Examples of containers include multiwell plates which allow simultaneous detection of IGF-1R protein in multiple samples.

In some embodiments, antibodies that bind to a IGF-1R protein are provided. In some embodiments, the antibody is isolated. In some embodiments, the antibody binds specifically. In some embodiments, the antibody binds to a IGF-1R protein that is properly folded. In some embodiments, the antibody is specific for a specific IGF-1R conformational state (open or closed). In some embodiments, the antibody binds to a IGF-1R protein in a cell membrane. In some embodiments, the antibody binds to a IGF-1R protein that is in a cell membrane in an intact cell. In some embodiments, the antibody inhibits or neutralizes the function of a IGF-1R protein. As used herein, the term "neutralize" means that the activity or function of the protein is inhibited. The inhibition can be complete or partial. In some embodiments, the activity or function of the protein is inhibited at least 10, 20, 30, 40, 50, 60, 70, 80, 90, 95, or 99%. The percent inhibition can be based upon the function or activity of the protein in the absence of the antibody. In some embodiments, the antibody inhibits the glucose transport facilitated by IGF-1R. In some embodiments, the antibody inhibits the internalization of the IGF-1R protein.

In some embodiments, the antibody comprises a sequence as provided for herein or antigen binding fragment thereof. In some embodiments, the antibody comprises a heavy chain CDR or an antigen binding fragment thereof described herein. The heavy chain may be one or more of the heavy chains described herein. In some embodiments, the antibody comprises a light chain, or an antigen binding fragment thereof as described herein In some embodiments, methods of treating, inhibiting or ameliorating a IGF-1R, associated pathology are provided. In some embodiments, the methods comprise administering an antibody described herein or a pharmaceutical composition described herein to a subject to treat, inhibit or ameliorate a IGF-1R associated pathology. In some embodiments, the pathology is as described herein.

In some embodiments, methods of detecting the presence or absence of a IGF-1R in a sample are provided, the method comprising contacting a sample with one or more antibodies described herein detecting the binding to a IGF-1R antigen by the antibody. In some embodiments, the detection of the binding indicates the presence IGF-1R antigen; or the absence of the detection of the binding to the IGF-1R antigen indicates the absence of the IGF-1R antigen. The detecting can be done with any known method, such as using a biosensor, ELISA, sandwich assay, and the like. However, in some embodiments, the method comprises detecting the presence of the protein in non-denaturing conditions. The non-denaturing conditions can be used so that the protein of interest is detected in its native, or properly folded form.

In some embodiments, methods of identifying a test antibody that binds to an epitope on IGF-1R protein, are provided, the method comprising contacting a test antibody with the epitope on IGF-1R protein and determining whether the test antibody binds to the epitope. In some embodiments, the determining comprises determining whether the test antibody binds to the protein and is competitively inhibited by an antibody comprising a sequence as provided herein. In some embodiments, the determining comprises mutating one or more residues of epitope or protein and determining binding of the test antibody to the mutated epitope, wherein if the mutation reduces binding of the test antibody as compared to the non-mutated epitope, the test antibody is deemed to bind to that epitope.

In some embodiments, methods of monitoring internalization of IGF-1R from the surface of a cell are provided. In some embodiments, the method comprising contacting the cell with an anti-IGF-1R antibody as provided herein and detecting the presence of IGF-1R in the cell or on the surface of the cell. The differences in cell surface expression can be measured and the internalization can be monitored and measured. This can be used, for example, to measure the effect of another molecule, such as a test agent, to modulate internalization of IGF-1R protein. Thus, the antibodies provided for herein can be used to identify test agents that modulate (increase or decrease) the internalization of IGF-1R protein. Test molecules that increase the internalization, which would be measured as a decrease in binding of an anti-IGF-1R antibody to IGF-1R protein on the cell surface, can be identified according to the methods provided herein. Test molecules that decrease the internalization, which would be measured as an increase in binding of an anti-IGF-1R antibody to IGF-1R protein on the cell surface, can be identified according to the methods provided herein. The surface expression can be measured by fluorescence, which can be done through a secondary antibody that recognized the IGF-1R antibodies or by labelling the anti-IGF-1R antibodies provided for herein.

In some embodiments, methods of inhibiting IGF-1 stimulated receptor phosphorylation on a cell are provided. In some embodiments, the methods comprise contacting the cell with an antibody as provided for herein, or a pharmaceutical composition comprising the same. In some embodiments, the contacting comprises administering to a subject the antibody or a pharmaceutical composition comprising the same. In some embodiments, the cell is a cell in the eye. In some embodiments, the subject has or is at risk of thyroid eye disease (TED). In some embodiments, the antibody has an IC50 of less than, or equal to, about 0.2 nm, 0.15 nm, 0.10 nm, 0.09 nm. In some embodiments, the IC50 is measured in an in vitro assay, such as an assay as provided for herein, such as illustrated in the Examples. In some embodiments, the IC50 is measured in an cell that is an A549 cell or a HOCF cell.

In some embodiments, methods of treating thyroid eye disease in a subject are provided, the method comprising administering an antibody as provided for herein, or a pharmaceutical composition comprising the same to the subject, wherein the antibody has a serum concentration in the subject of at least, or about, 70 µg/ml, 75 µg/ml, 80 µg/ml, 85 µg/ml, 90 µg/ml, 95 µg/ml, 100 µg/ml, or 105 µg/ml at least 1, 2, or 3 weeks after administration. In some embodiments, the serum concentration is measured after one, two or three doses of the antibody, or the pharmaceutical composition comprising the same, are administered to the subject.

In some embodiments, methods of inhibiting IGF-1 induced receptor autophosphorylation by at least 95%, 96%, 97%, 98%, or 99% or by 100% in a subject in need thereof are provided. In some embodiments, the methods comprise administering to the subject an antibody as provided for herein, or a pharmaceutical composition comprising the same. In some embodiments, the IGF-1 induced receptor autophosphorylation is inhibited in the eye or orbital region of the subject. In some embodiments, the IGF-1 induced receptor autophosphorylation is inhibited thereby treating a subject for thyroid eye disease or improving a symptom as described herein.

ENUMERATED EMBODIMENTS

In some embodiments, embodiments provided herein also include, but are not limited to:

1. An antibody, or antigen binding fragment thereof, comprising:
   a VL sequence as set forth in SEQ ID NO: 1, 3, 5, 7, 9, 11, 13, 15, 79, or 86;
   a VH sequence as set forth in SEQ ID NO: 2, 4, 6, 8, 10, 12, 14, 16, 80, or 83;
   a LCDR sequence as set forth in SEQ ID NO: 17, 18, 19, 23, 24, 25, 29, 30, 31, 35, 36, 37, 41, 42, 43, 47, 48, 49, 53, 54, 55, 59, 60, 61, or 81, or a HCDR sequence as set forth in SEQ ID NO: 20, 21, 22, 26, 27, 28, 32, 33, 34, 38, 39, 40, 44, 45, 46, 50, 51, 52, 56, 57, 58, 62, 63, or 64; and
   any combination or variant thereof.

2. The antibody of embodiment 1, or antigen binding fragment thereof, wherein the antibody binds to IGF-1R.

3. The antibody of embodiment 1, wherein the antibody is a monoclonal antibody.

4. The antibody of embodiment 1, wherein the antibody is a humanized antibody.

5. The antibody of embodiment 1, wherein the antibody is a scFv antibody.

6. The antibody of any one of embodiments 1-5, wherein the antibody, or antigen binding fragment thereof, comprises a $V_L$ peptide as set forth in SEQ ID NOs: 1, 3, 5, 7, 9, 11, 13, 15, 79, or 86, or any variant thereof.

7. The antibody of any one of embodiments 1-6, wherein the antibody, or antigen binding fragment thereof, comprises a $V_H$ peptide as set forth in SEQ ID NOs: 2, 4, 6, 8, 10, 12, 14, 16, 80, or 83, or any variant thereof.

8. An antibody, or antigen binding fragment thereof, wherein the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 20, 26, 32, 38, 44, 50, or 56; the heavy chain CDR2 has the amino acid sequence of SEQ ID NO: 21, 27, 33, 39, 45, 51, or 57; and the heavy chain CDR3 sequence has the amino acid sequence of SEQ ID NO: 22, 28, 34, 40, 46, 52, or 58; or variants of any of the foregoing; and (ii) a light chain variable region comprising light chain CDR1, CDR2, and CDR3 sequences, wherein the light chain CDR1 sequence has the amino acid sequence SEQ ID NO: 17, 23, 29, 35, 41, 47, or 53; the light chain CDR2 sequence has the amino acid sequence of SEQ ID NO: 18, 24, 30, 36, 42, 48, or 54; and the light chain CDR3 sequence has the amino acid sequence of SEQ ID NO: 19, 25, 31, 37, 43, 49, 55, or 81; or variants of any of the foregoing.

9. An antibody, or antigen binding fragment thereof, wherein the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 20; the heavy chain CDR2 has the amino acid sequence of SEQ ID NO: 21; and the heavy chain CDR3 sequence has the amino acid sequence of SEQ ID NO: 22; or variants of any of the foregoing; and (ii) a light chain variable region comprising light chain CDR1, CDR2, and CDR3 sequences, wherein the light chain CDR1 sequence has the amino acid sequence SEQ ID NO: 17; the light chain CDR2 sequence has the amino acid sequence of SEQ ID NO: 18; and the light chain CDR3 sequence has the amino acid sequence of SEQ ID NO: 19; or variants of any of the foregoing.

10. An antibody, or antigen binding fragment thereof, wherein the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 26; the heavy chain CDR2 has the amino acid sequence of SEQ ID NO: 27; and the heavy chain CDR3 sequence has the amino acid sequence of SEQ ID NO: 28; or variants of any of the foregoing; and (ii) a light chain variable region comprising light chain CDR1, CDR2, and CDR3 sequences, wherein the light chain CDR1 sequence has the amino acid sequence SEQ ID NO: 23; the light chain CDR2 sequence has the amino acid sequence of SEQ ID NO: 24; and the light chain CDR3 sequence has the amino acid sequence of SEQ ID NO: 25; or variants of any of the foregoing.

11. An antibody, or antigen binding fragment thereof, wherein the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 32; the heavy chain CDR2 has the amino acid sequence of SEQ ID NO: 33; and the heavy chain CDR3 sequence has the amino acid sequence of SEQ ID NO: 34; or variants of any of the foregoing; and (ii) a light chain variable region comprising light chain CDR1, CDR2, and CDR3 sequences, wherein the light chain CDR1 sequence has the amino acid sequence SEQ ID NO: 29; the light chain CDR2 sequence has the amino acid sequence of SEQ ID NO: 30; and the light chain CDR3 sequence has the amino acid sequence of SEQ ID NO: 31; or variants of any of the foregoing.

12. An antibody, or antigen binding fragment thereof, wherein the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 38; the heavy chain CDR2 has the amino acid sequence of SEQ ID NO: 39; and the heavy chain CDR3 sequence has the amino acid sequence of SEQ ID NO: 40; or variants of any of the foregoing; and (ii) a light chain variable region comprising light chain CDR1, CDR2, and CDR3 sequences, wherein the light chain CDR1 sequence has the amino acid sequence SEQ ID NO: 35; the light chain CDR2 sequence has the amino acid sequence of SEQ ID NO: 36; and the light chain CDR3 sequence has the amino acid sequence of SEQ ID NO: 37; or variants of any of the foregoing.

13. An antibody, or antigen binding fragment thereof, wherein the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 44; the heavy chain CDR2 has the amino acid sequence of SEQ ID NO: 45; and the heavy chain CDR3 sequence has the amino acid sequence of SEQ ID NO: 46; or variants of any of the foregoing; and (ii) a light chain variable region comprising light chain CDR1, CDR2, and CDR3 sequences, wherein the light chain CDR1 sequence has the amino acid sequence SEQ ID NO: 41; the light chain CDR2 sequence has the amino acid sequence of SEQ ID NO: 42; and the light chain CDR3 sequence has the amino acid sequence of SEQ ID NO: 43; or variants of any of the foregoing.

14. An antibody, or antigen binding fragment thereof, wherein the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 50; the heavy chain CDR2 has the amino acid sequence of SEQ ID NO: 51; and the heavy chain CDR3 sequence has the amino acid sequence of SEQ ID NO: 52; or variants of any of the foregoing; and (ii) a light chain variable region comprising light chain CDR1, CDR2, and CDR3 sequences, wherein the light chain CDR1 sequence has the amino acid sequence SEQ ID NO: 47; the light chain CDR2 sequence has the amino acid sequence of SEQ ID NO: 48; and the light chain CDR3 sequence has the amino acid sequence of SEQ ID NO: 49; or variants of any of the foregoing.

15. An antibody, or antigen binding fragment thereof, wherein the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 56; the heavy chain CDR2 has the amino acid sequence of SEQ ID NO: 57; and the heavy chain CDR3 sequence has the amino acid sequence of SEQ ID NO: 58; or variants of any of the foregoing; and (ii) a light chain variable region comprising light chain CDR1, CDR2, and CDR3 sequences, wherein the light chain CDR1 sequence has the amino acid sequence SEQ ID NO: 53; the light chain CDR2 sequence has the amino acid sequence of SEQ ID NO: 54; and the light chain CDR3 sequence has the amino acid sequence of SEQ ID NO: 55; or variants of any of the foregoing.

16. An antibody, or antigen binding fragment thereof, wherein the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 62; the heavy chain CDR2 has the amino acid sequence of SEQ ID NO: 63; and the heavy chain CDR3 sequence has the amino acid sequence of SEQ ID NO: 64; or variants of any of the foregoing; and (ii) a light chain variable region comprising light chain CDR1, CDR2, and CDR3 sequences, wherein the light chain CDR1 sequence has the amino acid sequence SEQ ID NO: 59; the light chain CDR2 sequence has the amino acid sequence of SEQ ID NO: 60; and the light chain CDR3 sequence has the amino acid sequence of SEQ ID NO: 61; or variants of any of the foregoing.

17. An antibody, or antigen binding fragment thereof, wherein the antibody or antibody fragment comprises: (i) a heavy chain variable region comprising heavy chain CDR1, CDR2, and CDR3 sequences, wherein the heavy chain CDR1 sequence has the amino acid sequence of SEQ ID NO: 38; the heavy chain CDR2 has the amino acid sequence of SEQ ID NO: 39; and the heavy chain CDR3 sequence has the amino acid sequence of SEQ ID NO: 40; or variants of any of the foregoing; and (ii) a light chain variable region comprising light chain CDR1, CDR2, and CDR3 sequences, wherein the light chain CDR1 sequence has the amino acid sequence SEQ ID NO: 35; the light chain CDR2 sequence has the amino acid sequence of SEQ ID NO: 36; and the light chain CDR3 sequence has the amino acid sequence of SEQ ID NO: 81; or variants of any of the foregoing.

18. The antibody of any one of embodiments 6-17, wherein the heavy chain variable region and the light chain variable region are not linked by a linker.

19. The antibody of any one of embodiments 6-17, wherein the heavy chain variable region and the light chain variable region are linked with a peptide linker.

20. The antibody of embodiment 19, wherein the peptide linker comprises a sequence of: $(GGGGS)_n$ (SEQ ID NO: 73) $(GGGGA)_n$ (SEQ ID NO: 74), or any combination thereof, wherein each n is independently 1-5.

21. The antibody of any one of embodiments 1-20, wherein the antibody comprises a sequence of SEQ ID NO: 65-72, 78, 82, or 85, or a variant thereof.

22. The antibody of any one of embodiments 1-21, wherein the antibody comprises a $V_L$ sequence as set forth in SEQ ID NO: 1, 3, 5, 7, 9, 11, 13, 15, 79, or 86, or a variant thereof.

23. The antibody of any one of embodiments 1-21, wherein the antibody comprises a $V_H$ sequence as set forth in SEQ ID NO: 2, 4, 6, 8, 10, 12, 14, 16, 80, or 83, or a variant thereof.

24. The isolated antibody of any one of embodiments 1-21, wherein the antibody comprises a sequence of SEQ ID NO: 65-72, 78, 82, or 85, or a variant thereof.

25. The antibody of any one of embodiments 1-24, wherein the variant has 1-10 substitutions, deletions, or insertions.

26. The antibody of any one of embodiments 1-24, wherein the variant has 1-10 conservative substitutions.

27. The antibody of any one of embodiments 1-26, wherein the variant has at least 85% homology to a sequence of SEQ ID NO: 1-72, 78-83, or 85-86.

28. The antibody of any one of embodiments 1-26, wherein the variant has at least 90%, 91%, 92%, 93%, 94%, 95%, 96%, 97%, 98%, or 99% homology to a sequence of SEQ ID NO: 1-72, 78-83, or 85-86.

29. The antibody of any one of embodiments 1-26, wherein the variant has at least 85% identity to a sequence of SEQ ID NO: 1-72, 78-83, or 85-86.

30. The antibody of any one of embodiments 1-26, wherein the variant has at least 90%, 91%, 92%, 93%, 94%, 95%, 96%, 97%, 98%, or 99% identify to a sequence of SEQ ID NO: 1-72, 78-83, or 85-86.

31. The antibody of any one of embodiments 1-26, wherein the antibody is a scFv antibody.

32. The antibody of any one of embodiments 1-26, wherein the antibody is a monoclonal antibody.

33. The antibody of any one of embodiments 1-26, wherein the antibody is a humanized antibody.

34. The antibody of any one of the preceding embodiments, wherein the antibody comprises a Fc region.

35. The antibody of embodiment 34, wherein the Fc region is as set forth in SEQ ID NO: 75-77, or 84.

36. The antibody of any one of the preceding embodiments, wherein the Fc region comprises a mutation that extends the half-life of the antibody when linked to the Fc region.

37. The antibody of embodiment 36, wherein the Fc region comprises a S228P, L235E, M252Y, S254T, T256E, M428L, N434S, L234F, P331S mutation, or any combination thereof.

38. The antibody of embodiment 36, wherein the Fc region comprises a M252Y, S254T, and T256E mutation.

39. The antibody of embodiment 36, wherein the Fc region comprises a S228P and a L235E mutation.

40. The antibody of embodiment 36, wherein the Fc region comprises a L234F, L235E, and P331S mutation.

41. The antibody of embodiment 36, wherein the Fc region comprises M252Y, S254T, T256E, S228P and L235E mutations.

42. The antibody of embodiment 36, wherein the Fc region comprises S228P, L235E, M428L, and N434S mutations.

43. The antibody of embodiment 36, wherein the Fc region comprises M428L and N434S mutations.

44. The antibody of embodiment 36, wherein the Fc region comprises L234F, L235E, P331S, M252Y, S254T, and T256E mutations.

45. A nucleic acid molecule encoding an antibody, or antigen binding fragment thereof, of any of the preceding embodiments.

46. A vector comprising the nucleic acid molecule of embodiment 45.

47. A cell comprising the nucleic comprising the nucleic acid molecule of embodiment 46 or the vector of embodiment 46.

48. A pharmaceutical composition comprising the antibody of any one of embodiments 1-44 or a nucleic acid molecule encoding the same.

49. The pharmaceutical composition of embodiment 48, wherein the composition is an injectable pharmaceutical composition.

50. A method of treating or reducing the severity of, thyroid-associated ophthalmopathy (TAO), or a symptom thereof, comprising administering to a subject an antibody of any one of embodiments 1-44 or a pharmaceutical composition comprising the same.

51. A method of reducing proptosis in an eye in a subject with thyroid-associated ophthalmopathy (TAO) comprising administering to a subject an antibody of any one of embodiments 1-44 or a pharmaceutical composition comprising the same.

52. A method of treating thyroid eye disease in a subject comprising administering to a subject an antibody of any one of embodiments 1-44 or a pharmaceutical composition comprising the same.

53. A method of reducing Clinical Activity Score (CAS) of thyroid-associated ophthalmopathy (TAO) in a subject comprising administering to a subject an antibody of any one of embodiments 1-44 or a pharmaceutical composition comprising the same.

54. A method of a) reducing proptosis by at least 2 mm and b) reducing the clinical activity score (CAS) in a subject with thyroid-associated ophthalmopathy (TAO) comprising administering to a subject an antibody of any one of embodiments 1-44 or a pharmaceutical composition comprising the same.

55. The method of any of embodiments 50-54, wherein proptosis is reduced by at least 2 mm.

56. The method of any of embodiments 50-54, wherein proptosis is reduced by at least 3 mm.

57. The method of any of embodiments 50-54, wherein proptosis is reduced by at least 4 mm.

58. The method of any of embodiments 50-54, wherein the clinical activity score (CAS) of the subject is reduced by at least 2 points.

59. The method of any of embodiments 50-54, wherein the clinical activity score (CAS) of the subject is reduced to one (1).

60. The method of any of embodiments 50-54, wherein the clinical activity score (CAS) of the subject is reduced to zero (0).

61. A method of treating or reducing the severity of thyroid-associated ophthalmopathy (TAO) in a subject comprising administering to a subject an antibody of any one of embodiments 1-44 or a pharmaceutical composition comprising the same, wherein treatment with said antibody (i) reduces proptosis by at least 2 mm in an eye; (ii) is not accompanied by a deterioration of 2 mm or more in the other (or fellow eye); and (iii) reduces the CAS in said subject to either one (1) or zero (0).

62. A method of improving the quality of life in a subject with thyroid-associated ophthalmopathy (TAO, also called Graves' Ophthalmopathy/Graves' Orbitopathy) comprising administering to a subject an antibody of any one of embodiments 1-44 or a pharmaceutical composition comprising the same.

63. The method of embodiment 62, wherein the quality of life is measured by the Graves' Ophthalmopathy Quality of Life (GO-QoL) assessment, or either the Visual Functioning or Appearance subscale thereof.

64. The method of embodiment 63, wherein the treatment results in an improvement of greater than or equal to 8 points on the GO-QoL.

65. The method of embodiment 63, wherein the treatment results in an improvement on the Functioning subscale of the GO-QoL.

66. The method of embodiment 63, wherein the treatment results in an improvement on the Appearance subscale of the GO-QoL.

67. A method of treating or reducing the severity of diplopia in a subject with thyroid-associated ophthalmopathy (TAO) comprising administering to a subject an antibody of any one of embodiments 1-44 or a pharmaceutical composition comprising the same.

68. The method of embodiment 67, wherein the diplopia is constant diplopia.

69. The method of embodiment 67, wherein the diplopia is inconstant diplopia.

70. The method of embodiment 67, wherein the diplopia is intermittent diplopia.

71. The method of embodiment 67, wherein the improvement in or reduction in severity of diplopia is sustained at least 20 weeks after discontinuation of antibody administration.

72. The method of embodiment 67, wherein the improvement in or reduction in severity of diplopia is sustained at least 50 weeks after discontinuation of antibody administration.

73. The method of any one of embodiments 50-72, wherein said antibody is administered at a dosage of about 1 mg/kg to about 5 mg/kg antibody as a first dose.

74. The method of any one of embodiments 50-72, wherein said antibody is administered at a dosage of about 5 mg/kg to about 10 mg/kg antibody as a first dose.

75. The method of any one of embodiments 50-72, wherein said antibody is administered at a dosage of about 5 mg/kg to about 20 mg/kg antibody in subsequent doses.

76. The method of any one of embodiments 50-72, wherein said antibody is administered in the following amounts: about 10 mg/kg antibody as a first dose; and about 20 mg/kg antibody in subsequent doses.

77. The method of embodiment 76, wherein said subsequent doses are administered every three weeks for at least 21 weeks.

78. The method of any one of embodiments 50-77, wherein the antibody, or an antigen binding fragment thereof, is a human antibody, a monoclonal antibody, a human monoclonal antibody, a purified antibody, a diabody, a single-chain antibody, a multi-specific antibody, Fab, Fab', F(ab')2, Fv or scFv.

79. The method of any one of embodiments 50-78, wherein the antibody, or an antigen binding fragment thereof, is administered in a pharmaceutical composition that additionally comprises a pharmaceutically acceptable diluent or excipient or carrier.

80. The method of embodiment 79, wherein the pharmaceutical composition further comprises one or more pharmaceutically active compounds for the treatment of TAO.

81. The method of embodiment 79 or 80, wherein the pharmaceutical composition further comprises corticosteroids; rituximab or other anti-CD20 antibodies; tocilizumab or other anti-IL-6 antibodies; or selenium, infliximab or other anti-TNFalpha antibodies or a thyroid-stimulating hormone receptor (TSHR) inhibitor.

82. The method of any of the preceding embodiments, wherein the antibody or an antigen binding fragment thereof is administered directly to the eye, the anterior chamber of the eye, the vitreous chamber of the eye, the suprachoroidal space, or the retro-orbital sinus.

83. The method of embodiment 82, wherein the antibody or an antigen binding fragment thereof is administered via an injection.

84. The method of embodiment 83, wherein the injection is a intravitreal injection, intraorbital injection, retro-orbital injection, suprachoroidal injection, or intracameral injection.

85. A method of increasing the internalization of IGF-1R on a cell, the method comprising contacting the cell with an antibody of any one of embodiments 1-44 or a pharmaceutical composition comprising the same.

86. The method of embodiment 85, wherein the contacting comprises administering to a subject an antibody of any one of embodiments 1-44 or a pharmaceutical composition comprising the same.

87. The method of embodiment 86, wherein the subject has or is at risk of thyroid eye disease (TED).

88. A method of inhibiting IGF-1 stimulated receptor phosphorylation on a cell, the method comprising contacting the cell with an antibody of any one of embodiments 1-44 or a pharmaceutical composition comprising the same.

89. The method of embodiment 88, wherein the contacting comprises administering to a subject an antibody of any one of embodiments 1-44 or a pharmaceutical composition comprising the same.

90. The method of embodiment 89, wherein the subject has or is at risk of thyroid eye disease (TED).

91. The method of any one of embodiments 88-90, wherein the antibody has an IC50 of less than, or equal to, about 0.2 nm, 0.15 nm, 0.10 nm, 0.09 nm.

92. The method of embodiment 91, wherein the IC50 is measured in an in vitro assay, such as an assay as provided for herein.

93. The method of any one of embodiments 88-92, wherein the cell is an A549 cell or a HOCF cell.

94. A method of treating thyroid eye disease in a subject, the method comprising administering an antibody of any one of embodiments 1-44 or as otherwise provided for herein, or a pharmaceutical composition comprising the same to the subject, wherein the antibody has a serum concentration in the subject of at least, or about, 70 μg/ml, 75 μg/ml, 80 μg/ml, 85 μg/ml, 90 μg/ml, 95 μg/ml, 100 μg/ml, or 105 μg/ml at least 1, 2, or 3 week after administration.

95. The method of embodiment 94, wherein the antibody or the pharmaceutical composition is administered intravenously.

96. The method of embodiments 94 or 96, wherein the antibody or the pharmaceutical composition is administered at a dose of about 20 mg/kg.

97. The method of any one of embodiments 94-96, wherein the antibody or the pharmaceutical composition is administered at least, or about, once a week, once every two weeks, once every 3 weeks, or once every 4 weeks.

98. A method of inhibiting IGF-1 induced receptor autophosphorylation in a cell by at least 95%, 96%, 97%, 98%, or 99% or by 100%, the method comprising contacting the cell with an antibody of any one of embodiments 1-44 or as otherwise provided for herein, or a pharmaceutical composition comprising the same.

99. The method of embodiment 98, wherein the inhibition of the IGF-1 induced receptor autophosphorylation is measured as compared to the induced receptor autophosphorylation in the absence of the antibody or the pharmaceutical composition.

100. The method of embodiments 98 or 99, wherein the contacting comprises administering to a subject the antibody or the pharmaceutical composition comprising the same.

101. The method of embodiment 100, wherein the subject has or is at risk of thyroid eye disease (TED).

102. A method of inhibiting IGF-1 induced receptor autophosphorylation by at least 95%, 96%, 97%, 98%, or 99% or by 100% in a subject in need thereof, the method comprising administering to the subject an antibody of any one of embodiments 1-44 or as otherwise provided for herein, or a pharmaceutical composition comprising the same.

103. The method of embodiment 102, wherein the subject has or is at risk of thyroid eye disease (TED).

104. The method of any one of embodiments 102 or 103, wherein the antibody or the pharmaceutical composition is administered intravenously.

105. The method of any one of embodiments 98-104, wherein the antibody comprises the CDRs of VRDN-1100.

106. The method of any one of embodiments 98-104, wherein the antibody comprises the CDRs of the antibody of VRDN-1100 or the CDRs of VRDN-2700.

107. An isolated antibody comprising a light chain having the amino acid sequence of SEQ ID NO: 3 and a heavy chain comprising the amino acid sequence of SEQ ID NO: 83.

108. An isolated antibody comprising a light chain variable region having the amino acid sequence of SEQ ID NO: 13 and a heavy chain variable region having the amino acid sequence of SEQ ID NO: 14.

109. The isolated antibody of embodiment 108, wherein antibody comprises a light chain having a an amino acid sequence of SEQ ID NO: 93 and a heavy chain amino acid sequence of SEQ ID NO: 92.

110. The isolated antibody of embodiment 108, wherein antibody comprises a light chain having a an amino acid sequence of SEQ ID NO: 93 and a heavy chain amino acid sequence of SEQ ID NO: 94.

111. The isolated antibody of embodiment 108, wherein antibody comprises a light chain having a an amino acid sequence of SEQ ID NO: 93 and a heavy chain amino acid sequence of SEQ ID NO: 95.

112. A pharmaceutical composition comprising the antibody of any one of embodiments 107-111.

113. A pharmaceutical composition suitable for intravenous administration comprising the antibody of any one of embodiments 107-111.

114. A pharmaceutical composition suitable for subcutaneous administration comprising the antibody of any one of embodiments 107-111.

115. A method of treating thyroid eye disease in a subject, the method comprising administering a pharmaceutical composition comprising the antibody of any one of embodiments 107-111.

116. The method of embodiment 115, wherein the pharmaceutical composition is administered intravenously.

117. The method of embodiment 115, wherein the pharmaceutical composition is administered subcutaneously.

118. A method of treating or reducing the severity of, thyroid-associated ophthalmopathy (TAO), or a symptom thereof, comprising administering to a subject an antibody of any one of embodiments 107-111 or a pharmaceutical composition comprising the same.

119. A method of reducing proptosis in an eye in a subject with thyroid-associated ophthalmopathy (TAO) comprising administering to a subject an antibody of an antibody of any one of embodiments 107-111 or a pharmaceutical composition comprising the same.

120. A method of treating thyroid eye disease in a subject comprising administering to a subject an antibody of any one of embodiments 107-111 or a pharmaceutical composition comprising the same.

121. A method of reducing Clinical Activity Score (CAS) of thyroid-associated ophthalmopathy (TAO) in a subject comprising administering to a subject an antibody of any one of embodiments 107-111 or a pharmaceutical composition comprising the same.

122. A method of a) reducing proptosis by at least 2 mm and b) reducing the clinical activity score (CAS) in a subject with thyroid-associated ophthalmopathy (TAO) comprising administering to a subject an antibody of any one of embodiments 107-111 or a pharmaceutical composition comprising the same.

123. The method of any of embodiments 118-122, wherein proptosis is reduced by at least 2 mm.

124. The method of any of embodiments 118-122, wherein proptosis is reduced by at least 3 mm.

125. The method of any of embodiments 118-122, wherein proptosis is reduced by at least 4 mm.

126. The method of any of embodiments 118-122, wherein the clinical activity score (CAS) of the subject is reduced by at least 2 points.

127. The method of any of embodiments 118-122, wherein the clinical activity score (CAS) of the subject is reduced to one (1).

128. The method of any of embodiments 118-122, wherein the clinical activity score (CAS) of the subject is reduced to zero (0).

129. A method of treating or reducing the severity of thyroid-associated ophthalmopathy (TAO) in a subject comprising administering to a subject an antibody of any one of embodiments 107-111, or a pharmaceutical composition comprising the same, wherein treatment with said antibody (i) reduces proptosis by at least 2 mm in an eye; (ii) is not accompanied by a deterioration of 2 mm or more in the other (or fellow eye); and (iii) reduces the CAS in said subject to either one (1) or zero (0).

130. A method of improving the quality of life in a subject with thyroid-associated ophthalmopathy (TAO, also called Graves' Ophthalmopathy/Graves' Orbitopathy) comprising administering to a subject an antibody of any one of embodiments 107-111, or a pharmaceutical composition comprising the same.

131. The method of embodiment 130, wherein the quality of life is measured by the Graves' Ophthalmopathy Quality of Life (GO-QoL) assessment, or either the Visual Functioning or Appearance subscale thereof.

132. The method of embodiment 130, wherein the treatment results in an improvement of greater than or equal to 8 points on the GO-QoL.

133. The method of embodiment 130, wherein the treatment results in an improvement on the Functioning subscale of the GO-QoL.

134. The method of embodiment 130, wherein the treatment results in an improvement on the Appearance subscale of the GO-QoL.

135. A method of treating or reducing the severity of diplopia in a subject with thyroid-associated ophthalmopathy (TAO) comprising administering to a subject an antibody of any one of embodiments 107-111 or a pharmaceutical composition comprising the same.

136. The method of embodiment 135, wherein the diplopia is constant diplopia.

137. The method of embodiment 135, wherein the diplopia is inconstant diplopia.

138. The method of embodiment 135, wherein the diplopia is intermittent diplopia.

139. The method of embodiment 135, wherein the improvement in or reduction in severity of diplopia is sustained at least 20 weeks after discontinuation of antibody administration.

140. The method of embodiment 135, wherein the improvement in or reduction in severity of diplopia is sustained at least 50 weeks after discontinuation of antibody administration.

141. The method of any one of embodiments 115-140, wherein said antibody is administered at a dosage of about 1 mg/kg to about 5 mg/kg antibody as a first dose.

142. The method of any one of embodiments 115-140, wherein said antibody is administered at a dosage of about 5 mg/kg to about 10 mg/kg antibody as a first dose.

143. The method of any one of embodiments 115-140, wherein said antibody is administered at a dosage of about 5 mg/kg to about 20 mg/kg antibody in subsequent doses.

144. The method of any one of embodiments 115-140, wherein said antibody is administered in the following amounts: about 10 mg/kg antibody as a first dose; and about 20 mg/kg antibody in subsequent doses.

145. The method of embodiment 144, wherein said subsequent doses are administered every three weeks for at least 21 weeks.

146. The method of any one of embodiments 115-140, wherein the antibody is administered in a pharmaceutical composition that comprises a pharmaceutically acceptable diluent, excipient, or carrier.

147. The method of embodiment 146, wherein the pharmaceutical composition further comprises one or more pharmaceutically active compounds for the treatment of TAO.

148. The method of embodiment 146 or 147, wherein the pharmaceutical composition further comprises corticosteroids; rituximab or other anti-CD20 antibodies; tocilizumab or other anti-IL-6 antibodies; or selenium, infliximab or other anti-TNFalpha antibodies or a thyroid-stimulating hormone receptor (TSHR) inhibitor.

149. A method of increasing the internalization of IGF-1R on a cell, the method comprising contacting the cell with an antibody of any one of embodiments 107-111 or a pharmaceutical composition comprising the same.

150. The method of embodiment 149, wherein the contacting comprises administering to a subject the antibody, or a pharmaceutical composition comprising the same.

151. The method of embodiment 150, wherein the subject has or is at risk of thyroid eye disease (TED).

152. A method of inhibiting IGF-1 stimulated receptor phosphorylation on a cell, the method comprising contacting the cell with an antibody of any one of embodiments 107-111, or a pharmaceutical composition comprising the same.

153. The method of embodiment 152, wherein the contacting comprises administering to a subject an antibody of any one of embodiments 1-44 or a pharmaceutical composition comprising the same.

154. The method of embodiment 153, wherein the subject has or is at risk of thyroid eye disease (TED).

155. The method of embodiments 153 or 154, wherein the antibody has an IC50 of less than, or equal to, about 0.2 nm, 0.15 nm, 0.10 nm, 0.09 nm.

156. The method of embodiment 155, wherein the IC50 is measured in an in vitro assay, such as an assay as provided for herein.

157. The method of any one of embodiments 152-157, wherein the cell is an A549 cell or a HOCF cell.

158. A method of treating thyroid eye disease in a subject, the method comprising administering an antibody of any one of embodiments 107-111, or a pharmaceutical composition comprising the same to the subject, wherein the antibody has a serum concentration in the subject of at least, or about, 70 µg/ml, 75 µg/ml, 80 µg/ml, 85 µg/ml, 90 µg/ml, 95 µg/ml, 100 µg/ml, or 105 µg/ml at least 1, 2, or 3 weeks after administration.

159. The method of embodiment 158, wherein the antibody or the pharmaceutical composition is administered intravenously.

160. The method of embodiments 158 or 159, wherein the antibody or the pharmaceutical composition is administered at a dose of about 1 mg/kg to about 5 mg/kg (mg antibody/kg subject), of about 5 mg/kg to about 10 mg/kg antibody, or about 5 mg/kg to about 20 mg/kg in a first dose or subsequent dose.

161. The method of any one of embodiments 158-160, wherein said antibody is administered in the following amounts: about 1, 2, 3, 4, 5, 6, 7, 8, 9, or 10 mg/kg antibody as a first dose; and about 1, 2, 3, 4, 5, 6, 7, 8, 9, 10, 11, 12, 13, 14, 15, 16, 17, 18, 19, or 20 mg/kg antibody in subsequent doses.

162. The method of any one of embodiments 158-161, wherein the antibody or the pharmaceutical composition is administered at least, or about, once a week, once every two weeks, once every 3 weeks, or once every 4 weeks.

163. A method of inhibiting IGF-1 induced receptor autophosphorylation by at least 95%, 96%, 97%, 98%, or 99% or by 100% in a subject in need thereof, the method comprising administering to the subject an antibody of any one of embodiments 107-111, or a pharmaceutical composition comprising the same.

164. A pharmaceutical composition comprising an antibody for treating thyroid eye disease in a subject, wherein the antibody comprises a light chain variable region having the amino acid sequence of SEQ ID NO: 13 and a heavy chain variable region having the amino acid sequence of SEQ ID NO: 14.

165. The pharmaceutical composition of embodiment 164, wherein the antibody comprises a Fc region with M428L and N434S substitutions.

166. The pharmaceutical composition of embodiment 164, wherein the antibody comprises a Fc region with M428L, N434S, M252Y, S254T, and T256E substitutions.

167. The pharmaceutical composition of embodiment 164, wherein the antibody comprises a Fc region with M252Y, S254T, and T256E substitutions.

168. The pharmaceutical composition of embodiment 164, wherein antibody comprises a light chain having an amino acid sequence of SEQ ID NO: 93 and a heavy chain amino acid sequence of SEQ ID NO: 92.

169. The pharmaceutical composition of embodiment 164, wherein antibody comprises a light chain having a an amino acid sequence of SEQ ID NO: 93 and a heavy chain amino acid sequence of SEQ ID NO: 94.

170. The pharmaceutical composition of embodiment 164, wherein antibody comprises a light chain having a an amino acid sequence of SEQ ID NO: 93 and a heavy chain amino acid sequence of SEQ ID NO: 95.

171. A method of treating thyroid eye disease in a subject, the method comprising administering the pharmaceutical composition comprising the antibody of any one of embodiments 164-170.

172. The method of embodiment 171, wherein the pharmaceutical composition is administered intravenously.

173. The method of embodiment 171, wherein the pharmaceutical composition is administered subcutaneously.

174. A method of treating or reducing the severity of, thyroid-associated ophthalmopathy (TAO), or a symptom thereof, the method comprising administering to a subject the pharmaceutical composition of any one of embodiments 164-170.

175. A method of reducing proptosis in an eye in a subject with thyroid-associated ophthalmopathy (TAO), the method comprising administering to a subject the pharmaceutical composition of any one of embodiments 164-170.

176. A method of treating thyroid eye disease in a subject, the method comprising administering to a subject the pharmaceutical composition of any one of embodiments 2-4.

177. A method of reducing Clinical Activity Score (CAS) of thyroid-associated ophthalmopathy (TAO) in a subject, the method comprising administering to a subject the pharmaceutical composition of any one of embodiments 164-170.

178. A method of a) reducing proptosis by at least 2 mm and b) reducing the clinical activity score (CAS) in a subject with thyroid-associated ophthalmopathy (TAO), the method comprising administering to a subject the pharmaceutical composition of any one of embodiments 164-170.

179. The method of any of embodiments 174-178, wherein proptosis is reduced by at least 2 mm.

180. The method of any of embodiments 174-178, wherein proptosis is reduced by at least 3 mm.

181. The method of any of embodiments 174-178, wherein proptosis is reduced by at least 4 mm.

182. The method of any of embodiments 174-178, wherein the clinical activity score (CAS) of the subject is reduced by at least 2 points.

183. The method of any of embodiments 174-178, wherein the clinical activity score (CAS) of the subject is reduced to one (1).

184. The method of any of embodiments 174-178, wherein the clinical activity score (CAS) of the subject is reduced to zero (0).

185. A method of treating or reducing the severity of thyroid-associated ophthalmopathy (TAO) in a subject comprising administering to a subject a pharmaceutical composition of any one of embodiments 164-170, wherein treatment with said antibody (i) reduces proptosis by at least 2 mm in an eye; (ii) is not accompanied by a deterioration of 2 mm or more in the other (or fellow eye); and (iii) reduces the CAS in said subject to either one (1) or zero (0).

186. A method of improving the quality of life in a subject with thyroid-associated ophthalmopathy (TAO, also called Graves' Ophthalmopathy/Graves' Orbitopathy), the method comprising administering to a subject the pharmaceutical composition of any one of embodiments 164-170.

187. The method of embodiment 186, wherein the quality of life is measured by the Graves' Ophthalmopathy Quality of Life (GO-QoL) assessment, or either the Visual Functioning or Appearance subscale thereof.

188. The method of embodiment 186, wherein the treatment results in an improvement of greater than or equal to 8 points on the GO-QoL.

189. The method of embodiment 186, wherein the treatment results in an improvement on the Functioning subscale of the GO-QoL.

190. The method of embodiment 186, wherein the treatment results in an improvement on the Appearance subscale of the GO-QoL.

191. A method of treating or reducing the severity of diplopia in a subject with thyroid-associated ophthalmopathy (TAO), the method comprising administering to a subject the pharmaceutical composition of any one of embodiments 164-170.

192. The method of embodiment 191, wherein the diplopia is constant diplopia.

193. The method of embodiment 191, wherein the diplopia is inconstant diplopia.

194. The method of embodiment 191, wherein the diplopia is intermittent diplopia.

195. The method of embodiment 191, wherein the improvement in or reduction in severity of diplopia is sustained at least 20 weeks after discontinuation of antibody administration.

196. The method of embodiment 191, wherein the improvement in or reduction in severity of diplopia is sustained at least 50 weeks after discontinuation of antibody administration.

197. The method of any one of embodiments 171-196, wherein said pharmaceutical composition is administered at a dosage of about 1 mg/kg to about 5 mg/kg, about 5 mg/kg to about 10 mg/kg, about 10 mg/kg to about 20 mg/kg, about 20 mg/kg to about 30 mg/kg, about 5 mg/kg, about 10 mg/kg, about 15 mg/kg, about 20 mg/kg, about 25 mg/kg, or about 30 mg/kg of the antibody as a first dose.

198. The method of any one of embodiments 171-196, wherein said pharmaceutical composition is administered at a dosage of about 10 mg/kg to about 20 mg/kg of antibody as a first dose.

199. The method of any one of embodiments 171-196, wherein said pharmaceutical composition is administered at a dosage of about 1 mg/kg to about 10 mg/kg, about 2 mg/kg to about 5 mg/kg, or about 5 mg/kg to about 20 mg/kg of antibody in subsequent doses.

200. The method of any one of embodiments 171-196, wherein said pharmaceutical composition is administered in the following amounts: about 10 mg/kg antibody as a first dose; and about 20 mg/kg antibody in subsequent doses.

201. The method of embodiment 200, wherein said subsequent doses are administered every three weeks, every four weeks, every five weeks, every six weeks, every seven weeks, or every eight weeks for at least 21-52 weeks or longer.

202. A method of increasing the internalization of IGF-1R on a cell, the method comprising contacting the cell with the pharmaceutical composition of any one of embodiments 164-170.

203. The method of embodiment 202, wherein the contacting comprises administering to a subject the pharmaceutical composition of any one of embodiments 164-170.

204. The method of embodiment 203, wherein the subject has or is at risk of thyroid eye disease (TED).

205. A method of inhibiting IGF-1 stimulated receptor phosphorylation on a cell, the method comprising contacting the cell with the pharmaceutical composition of any one of embodiments 164-170.

206. The method of embodiment 205, wherein the contacting comprises administering to a subject the pharmaceutical composition of any one of embodiments 164-170.

207. The method of embodiment 206, wherein the subject has or is at risk of thyroid eye disease (TED).

208. The method of any one of embodiments 205-207, wherein the antibody has an IC50 of less than, or equal to, about 0.2 nm, 0.15 nm, 0.10 nm, 0.09 nm.

209. A method of treating thyroid eye disease in a subject, the method comprising administering the pharmaceutical composition of any one of embodiments 164-170 to the subject, wherein the antibody has a serum concentration in the subject of at least, or about, 10 µg/ml or 20 µg/ml or 50 µg/ml, 70 µg/ml, 75 µg/ml, 80 µg/ml, 85 µg/ml, 90 µg/ml, 95 µg/ml, 100 µg/ml, or 105 µg/ml at least 1, 2, or 3 weeks after administration.

210. The method of embodiment 209, wherein the pharmaceutical composition is administered intravenously or subcutaneously.

211. An isolated antibody comprising a light chain having the amino acid sequence of SEQ ID NO: 3 and a heavy chain comprising the amino acid sequence of SEQ ID NO: 83.

212. An isolated antibody comprising variable light chain comprising the sequence of SEQ ID NO: 98 and a variable heavy chain comprising the sequence of SEQ ID NO: 99 and a Fc region comprising M252Y, S254T, and T256E mutations.

213. An isolated antibody comprising variable light chain comprising the sequence of SEQ ID NO: 98 and a variable heavy chain comprising the sequence of SEQ ID NO: 99 and a Fc region comprising M428L and N434S mutations.

214. A pharmaceutical composition comprising the antibody of any one of embodiments 211-213.

215. A pharmaceutical composition suitable for intravenous administration comprising the antibody of any one of embodiments 211-213.

216. A pharmaceutical composition suitable for subcutaneous administration comprising the antibody of any one of embodiments 211-213.

217. A method of treating thyroid eye disease in a subject, the method comprising administering a pharmaceutical composition comprising the antibody of any one of embodiments 211-213.

218. The method of embodiment 217, wherein the pharmaceutical composition is administered intravenously.

219. The method of embodiment 217, wherein the pharmaceutical composition is administered subcutaneously.

220. A method of treating or reducing the severity of, thyroid-associated ophthalmopathy (TAO), or a symptom thereof, comprising administering to a subject an antibody of any one of embodiments 211-213 or a pharmaceutical composition comprising the same.

221. A method of reducing proptosis in an eye in a subject with thyroid-associated ophthalmopathy (TAO) comprising administering to a subject an antibody of any one of embodiments 211-213, or a pharmaceutical composition comprising the same.

222. A method of treating thyroid eye disease in a subject comprising administering to a subject an antibody of any one of embodiments 211-213, or a pharmaceutical composition comprising the same.

223. A method of reducing Clinical Activity Score (CAS) of thyroid-associated ophthalmopathy (TAO) in a subject comprising administering to a subject an antibody of any one of embodiments 211-213, or a pharmaceutical composition comprising the same.

224. A method of a) reducing proptosis by at least 2 mm and b) reducing the clinical activity score (CAS) in a subject with thyroid-associated ophthalmopathy (TAO) comprising administering to a subject an antibody of any one of embodiments 211-213, or a pharmaceutical composition comprising the same.

225. The method of any of embodiments 220-224, wherein proptosis is reduced by at least 2 mm.

226. The method of any of embodiments 220-224, wherein proptosis is reduced by at least 3 mm.

227. The method of any of embodiments 220-224, wherein proptosis is reduced by at least 4 mm.

228. The method of any of embodiments 220-224, wherein the clinical activity score (CAS) of the subject is reduced by at least 2 points.

229. The method of any of embodiments 220-224, wherein the clinical activity score (CAS) of the subject is reduced to one (1).

230. The method of any of embodiments 220-224, wherein the clinical activity score (CAS) of the subject is reduced to zero (0).

231. A method of treating or reducing the severity of thyroid-associated ophthalmopathy (TAO) in a subject comprising administering to a subject an antibody of any one embodiments 1-3, or a pharmaceutical composition comprising the same, wherein treatment with said antibody (i) reduces proptosis by at least 2 mm in an eye; (ii) is not accompanied by a deterioration of 2 mm or more in the other (or fellow eye); and (iii) reduces the CAS in said subject to either one (1) or zero (0).

232. A method of improving the quality of life in a subject with thyroid-associated ophthalmopathy (TAO, also called Graves' Ophthalmopathy/Graves' Orbitopathy) comprising administering to a subject an antibody of any one of embodiments 211-213, or a pharmaceutical composition comprising the same.

233. The method of embodiment 232, wherein the quality of life is measured by the Graves' Ophthalmopathy Quality of Life (GO-QoL) assessment, or either the Visual Functioning or Appearance subscale thereof.

234. The method of embodiment 232, wherein the treatment results in an improvement of greater than or equal to 8 points on the GO-QoL.

235. The method of embodiment 232, wherein the treatment results in an improvement on the Functioning subscale of the GO-QoL.

236. The method of embodiment 232, wherein the treatment results in an improvement on the Appearance subscale of the GO-QoL.

237. A method of treating or reducing the severity of diplopia in a subject with thyroid-associated ophthalmopathy (TAO) comprising administering to a subject an antibody of any one of embodiments 211-213, or a pharmaceutical composition comprising the same.

238. The method of embodiment 237, wherein the diplopia is constant diplopia.

239. The method of embodiment 237, wherein the diplopia is inconstant diplopia.

240. The method of embodiment 237, wherein the diplopia is intermittent diplopia.

241. The method of embodiment 237, wherein the improvement in or reduction in severity of diplopia is sustained at least 20 weeks after discontinuation of antibody administration.

242. The method of embodiment 237, wherein the improvement in or reduction in severity of diplopia is sustained at least 50 weeks after discontinuation of antibody administration.

243. The method of any one of embodiments 217-242, wherein said antibody is administered at a dosage of about 1 mg/kg to about 5 mg/kg, about 5 mg/kg to about 10 mg/kg, about 10 mg/kg to about 20 mg/kg, about 20 mg/kg to about 30 mg/kg, about 5 mg/kg, about 10 mg/kg, about 15 mg/kg, about 20 mg/kg, about 25 mg/kg, or about 30 mg/kg of the antibody as a first dose.

244. The method of any one of embodiments 217-242, wherein said antibody is administered at a dosage of about 10 mg/kg to about 20 mg/kg of antibody as a first dose.

245. The method of any one of embodiments 217-242, wherein said antibody is administered at a dosage of about 1 mg/kg to about 10 mg/kg, about 2 mg/kg to about 5 mg/kg, or about 5 mg/kg to about 20 mg/kg of antibody in subsequent doses.

246. The method of any one of embodiments 217-242, wherein said antibody is administered in the following amounts: about 10 mg/kg antibody as a first dose; and about 20 mg/kg antibody in subsequent doses.

247. The method of embodiment 246, wherein said subsequent doses are administered every three weeks, every four weeks, every five weeks, every six weeks, every seven weeks, or every eight weeks for at least 21-52 weeks or longer.

248. A method of increasing the internalization of IGF-1R on a cell, the method comprising contacting the cell with an antibody of any one of embodiments 211-213, or a pharmaceutical composition comprising the same.

249. The method of embodiment 248, wherein the contacting comprises administering to a subject the antibody, or a pharmaceutical composition comprising the same.

250. The method of embodiment 249, wherein the subject has or is at risk of thyroid eye disease (TED).

251. A method of inhibiting IGF-1 stimulated receptor phosphorylation on a cell, the method comprising contacting the cell with an antibody of any one of embodiments 211-213, or a pharmaceutical composition comprising the same.

252. The method of embodiment 251, wherein the contacting comprises administering to a subject an antibody of any one of embodiments 211-213 or a pharmaceutical composition comprising the same.

253. The method of embodiment 252, wherein the subject has or is at risk of thyroid eye disease (TED).

254. The method of any one of embodiments 251-253, wherein the antibody has an IC50 of less than, or equal to, about 0.2 nm, 0.15 nm, 0.10 nm, 0.09 nm.

255. A method of treating thyroid eye disease in a subject, the method comprising administering an antibody of any one of embodiments 211-213, or a pharmaceutical composition comprising the same to the subject, wherein the antibody has a serum concentration in the subject of at least, or about, 10 µg/ml or 20 µg/ml or 50 µg/ml, 70 µg/ml, 75 µg/ml, 80 µg/ml, 85 µg/ml, 90 µg/ml, 95 µg/ml, 100 µg/ml, or 105 µg/ml at least 1, 2, or 3 weeks after administration.

256. The method of embodiment 255, wherein the antibody or the pharmaceutical composition is administered intravenously or subcutaneously.

The subject matter is now described with reference to the following examples. These examples are provided for the purpose of illustration only and the claims should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

EXAMPLES

Example 1: IGF-1R Antibodies Block IGF-1 Stimulation

Blockage of IGF-1 stimulation is measured by secretion of hyaluronan, in the presence of IGF-1R antibodies VRDN-2700, VRDN-03100, VRDN-02100, VRDN-02200, VRDN-02300, VRDN-02400, VRDN-02500, VRDN-01100, VRDN-02600, and VRDN-02301, all of which are disclosed herein. Immunoglobulins are purified from the sera of patients with Graves' ophthalmopathy (GO) and tested for their ability to activate TSHR and/or IGF-1R directly, and TSHR/IGF-1R cross talk in primary cultures of GO fibroblasts. Cells are treated with M22 or GO-Igs with or without IGF-1R inhibitory antibodies such as those provided for herein, including but not limited to, VRDN-2700, VRDN-03100, VRDN-02100, VRDN-02200, VRDN-02300, VRDN-02400, VRDN-02500, VRDN-01100, VRDN-02600, and VRDN-02301, all of which are disclosed herein. Hyaluronan (hyaluronic acid; HA) secretion is measured as a major biological response for GO fibroblast stimulation. IGF-1R autophosphorylation is used as a measure of direct IGF-1R activation. TSHR activation is determined through cyclic-AMP (cAMP) production. The IGF-1R antibodies, as disclosed herein, are found to effectively block HA secretion and, therefore, are found to block IGF stimulation.

Example 2: Treatment of Patients with Thyroid Eye Disease and Clinical Assessment of IGF-1R Antibodies on Thyroid Eye Disease Infusions of IGF-1R inhibitory antibodies such as those provided for herein, including but not limited to, VRDN-2700, VRDN-03100, VRDN-02100, VRDN-02200, VRDN-02300, VRDN-02400, VRDN-02500, VRDN-01100, VRDN-02600, and VRDN-02301, all of which are disclosed herein, are provided to the subjects. The number of infusions is individualized for each subject and is based on the investigator's clinical judgment. The Day 1 Visit occurs within 14 days after the final visit of the prior trial. Visit windows are ±1 day for Weeks 1 and 4, ±3 days for Weeks 3, 6, 9, 12, 15, 18, 21, and 24. The Follow-up period is meant for subjects who were proptosis non-responders in the prior trial only; subjects who relapsed in the prior trial did not participate in the Follow-Up Period. Visit windows during the Follow-up period are ±7 days.

Treatment Period is 24 weeks (6 months), during which 8 infusions of teprotumumab are administered.

Subjects who are proptosis non-responders are scheduled to participate in a 6-month Follow-Up Period in this extension study; subjects who relapsed in the lead-in study and are retreated in this extension study will not participate in the Follow-Up Period.

Efficacy assessments are performed for both eyes at each assessment time point. The "study eye" (i.e., the more severely affected eye) will remain the same as that identified at the Baseline (Day 1) Visit of the prior study. Both eyes are assessed for efficacy but the study eye is used to assess the primary outcome measure.

Efficacy is assessed by proptosis (measured as exophthalmos evaluation of the Clinical Measures of Severity using a Hertel instrument for consistency in measurement), CAS (7-item scale), diplopia (measured as part of the Clinical Measures of Severity) and Clinical Measures of Severity (including motility restriction assessments).

Quality of life is assessed using the GO-QoL questionnaire.

Safety is assessed via AE and concomitant medication use monitoring, immunogenicity testing, physical and ophthalmic examinations, vital signs, clinical safety laboratory evaluations (complete blood count, chemistry (including thyroid panel and HbA1C), and urinalysis), pregnancy testing (if applicable), and electrocardiograms (ECG). The study is also monitored by a Data Safety Monitoring Board (DSMB).

Proptosis assessments is performed using a Hertel exophthalmometer for consistency in measurement, and (except when strictly unavoidable) the same Hertel instrument and same observer is used at each evaluation for the full duration of the study. Additionally, the same intercanthal distance (ICD) is used on each occasion.

Proptosis is measured for each eye on Day 1 and Weeks 6, 12, 18, and 24 (or premature withdrawal (PW)) during the Treatment Period, and at Months 7, 9, and 12 (or PW) during the Follow-Up Period. Measurements is recorded on the Clinical Measures of Severity eCRF under exophthalmos.

The antibodies are found to be effective in treating thyroid eye disease and also improving quality of life as provided for herein.

Example 3: Antibody with Increased pK

Cynomolgus monkeys were dosed with an antibody comprising the CDRs of VRDN-2700 with the YTE mutation in the Fc domain in an amount of 10 mg/kg by either intravenous or subcutaneous route, and samples were collected at 0.5 hr, 2 hr, 8 hr and days 1, 3, 7, 10, 14, 21, and 28 time points for PK analysis by ELISA. Teprotumumab was also administered at 10 mg/kg IV as a comparator. The results illustrated in FIG. 1 demonstrate that the antibody had a significantly higher PK as compared to Teprotumumab.

This result demonstrates an antibody comprising the CDRs of VRDN-2700 can likely be given at a lower dose as compared to Teprotumumab, even when administered subcutaneously. These results could not have been predicted.

Example 4

VRDN-1100 is an antagonist antibody to insulin-like growth factor-1 receptor (IGF-1R) under development for treatment of Thyroid Eye Disease (TED). TED is driven by Thyroid Stimulating Hormone Receptor (TSHR) agonistic autoantibodies and crosstalk between TSHR and IGF-1R. TED is characterized by recruitment of fibrocytes that express IGF-1R and TSHR in orbital tissues, where they mediate deposition of hyaluronan and expansion of orbital muscle and fat1. IGF-1R antagonism has been found to reverse this orbital tissue expansion and robustly relieve symptoms in TED patients2.

VRDN-1100 is a humanized monoclonal antibody targeting IGF-1R. The IGF-1R binding and antagonist characteristics of VRDN-1100 was analyzed.

Methods

Surface Plasmon Resonance (SPR):
Antibodies were captured by immobilized anti-Fc, and recombinant IGF-1R extracellular domain (ECD) was flowed as analyte. Association and dissociation rate constants (ka and kd, respectively), and equilibrium dissociation constant KD were derived by global fit of data to single site model.
Epitope Binning:
VRDN-1100 was immobilized on a chip surface by amine coupling and used to capture IGF-1R-ECD, after which teprotumumab was flowed over the chip.
Cell Binding:
A549 human lung adenocarcinoma cells or primary human ocular choroid fibroblasts (HOCF) were incubated with varying concentrations of VRDN-1100 or teprotumumab. A single dose 50 nM IgG1 isotype control was used as negative control. Unbound antibody was removed by washing, and the cells were incubated with an Alexa Fluor 488™_goat anti-human antibody (fluorescently labeled antibody) and a cell impermeable dye to gate live cells. The median fluorescence intensity (MFI) of viable cells was measured by flow cytometry and the data were analyzed using FlowJo™ software. Dose curves were fitted using a non-linear regression model; log(agonist) vs response-variable slope (four parameters).
Internalization:
Cells were incubated with various concentrations of antibodies of interest at 4° C. and 37° C. for 60 minutes. Cells were then washed 3× and incubated with FITC-labeled goat anti-human Fc secondary antibody for 30 minutes at 4° C. The MFI of viable cells was measured by flow cytometry and the data were analyzed using FlowJo™ software.
Cell Surface Marker Expression:
HOCF cells were incubated with directly labeled antibodies or IgG isotype control at 10 ug/mL. The median fluorescence intensity (MFI) was measured by flow cytometry and the data were analyzed using FlowJo™ software.
Antagonism:
Serum starved A549 or HOCF cells were preincubated with varying concentrations of test antibody for one hour at 37° C., then stimulated by addition of 100 ng/mL (A549s) or 200 ng/mL (HOCFs) IGF-1 for 7 minutes at 37° C. Phosphorylated IGF-1R (pIGF1R) of biological duplicates was measured using the R&D Systems pIGF-1R ELISA according to the manufacturer's protocol and pIGF-1R concentrations were normalized to the lowest test antibody concentration. Dose curves were fit using a non-linear regression model; log(inhibitor) vs response-variable slope (four parameters)).

Results

Figure 2A:
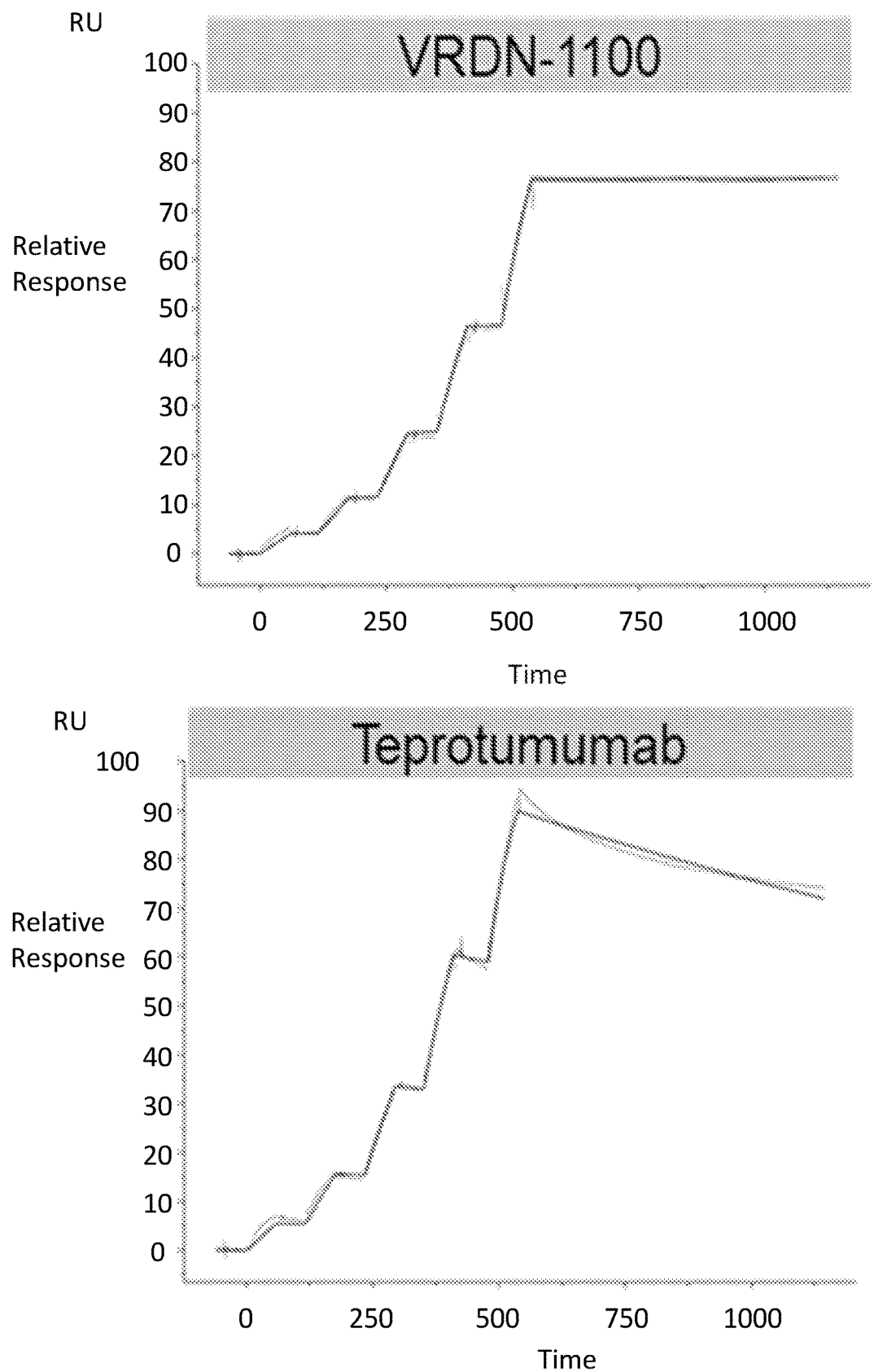
FIG. 2A and FIG. 2B illustrate that increasing concentrations of IGF-1R-ECD bound to anti-FC captured VRDN-1100 or teprotumumab reveal a stepwise increase in SPR signal, enabling a global fit to a binding mode.
Figure 2B:
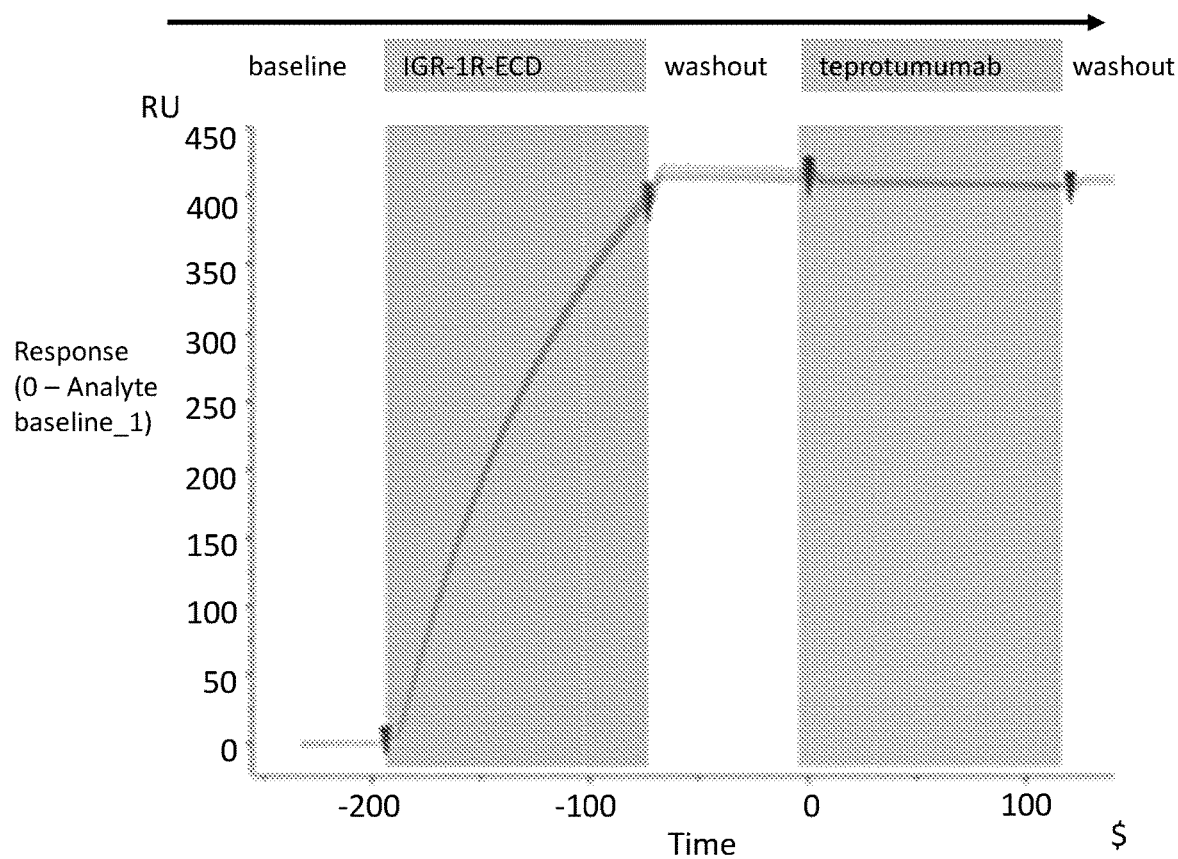
Figure 3A:
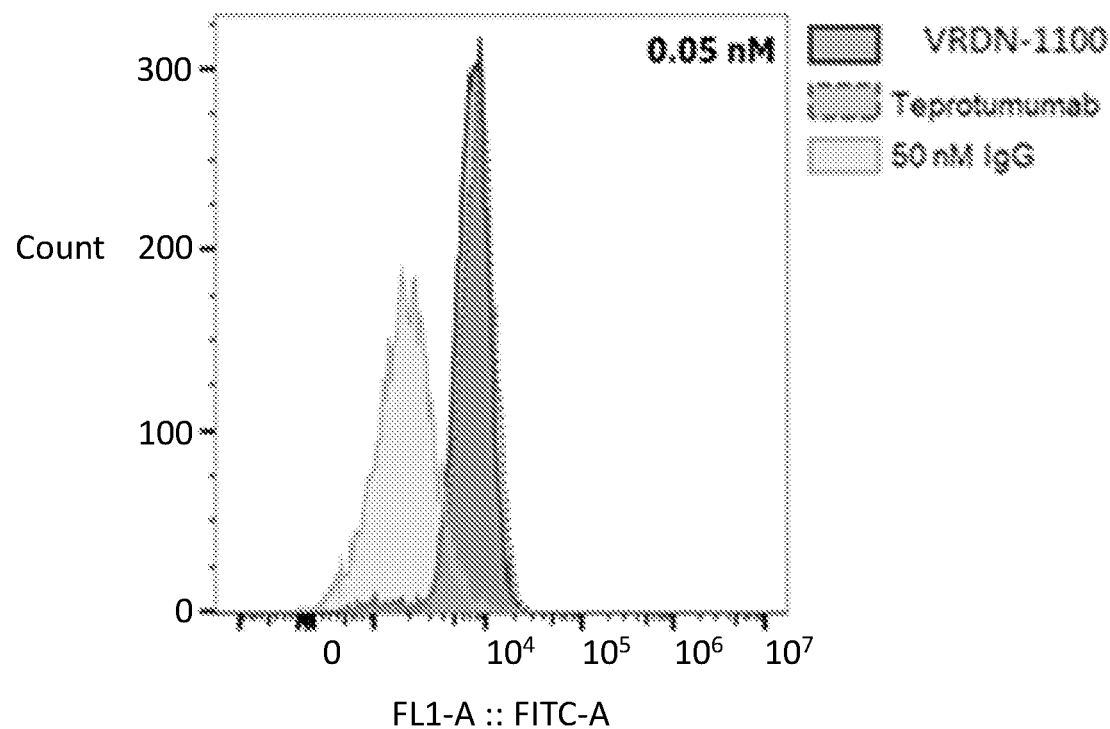
FIG. 3A-F illustrate various properties of antibodies as provided for herein, such as VRDN-1100 binding to A549 cells that was assessed by flow cytometry and found to have similar binding distribution as teprotumumab at three different concentrations and binding dose response curve demonstrating VRDN-1100 EC50=0.1 nM, and that the antibodies indicated therein show comparable binding at temperatures that block IGF-1R receptor internalization.
Figure 3B:
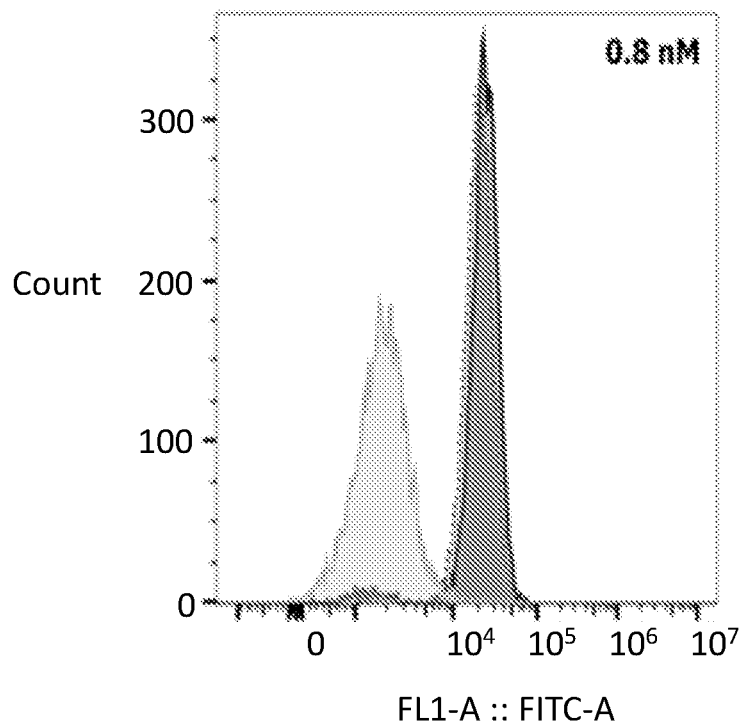
Figure 3C:
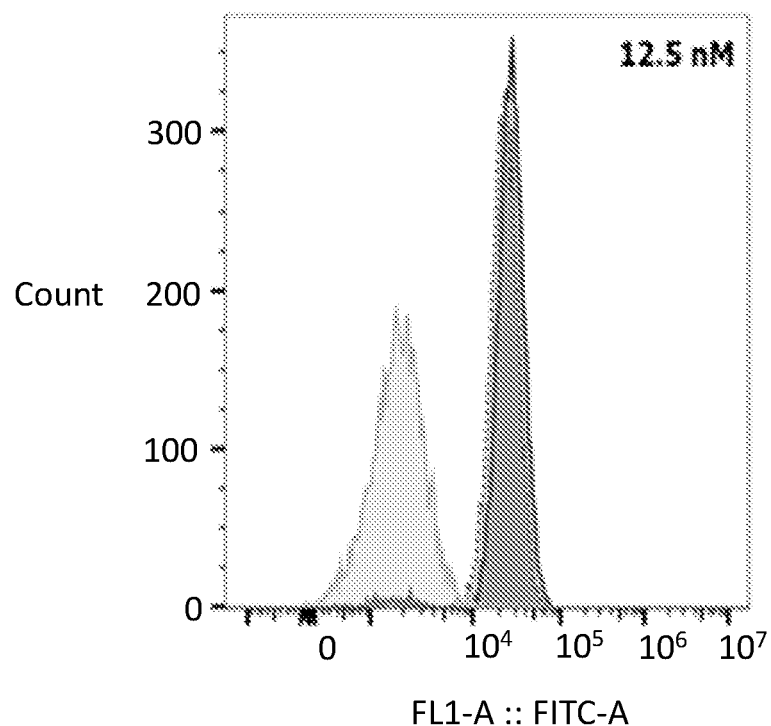
Figure 3D:
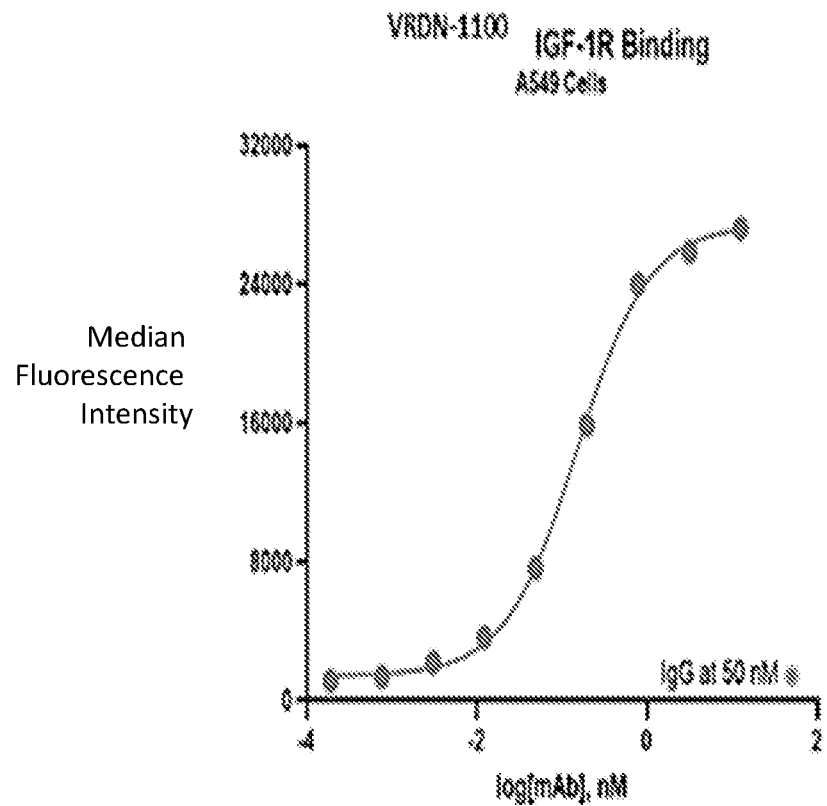
Figure 3E:
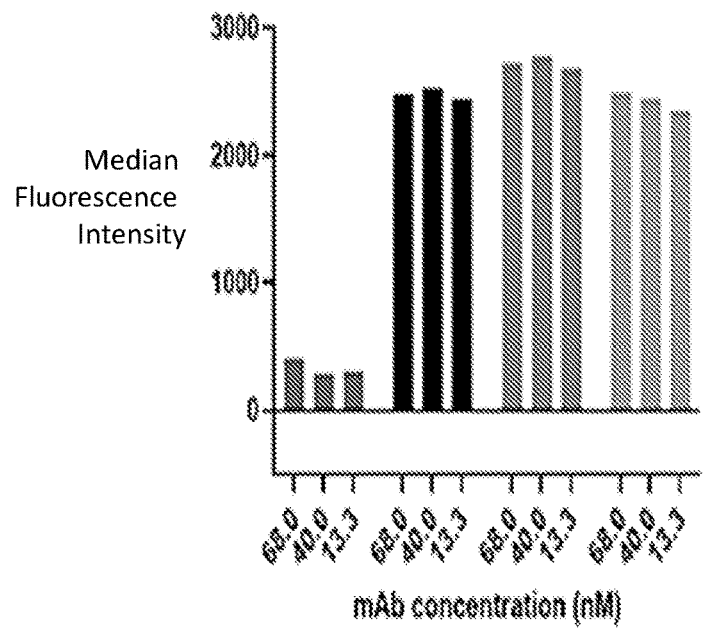
Figure 3F:
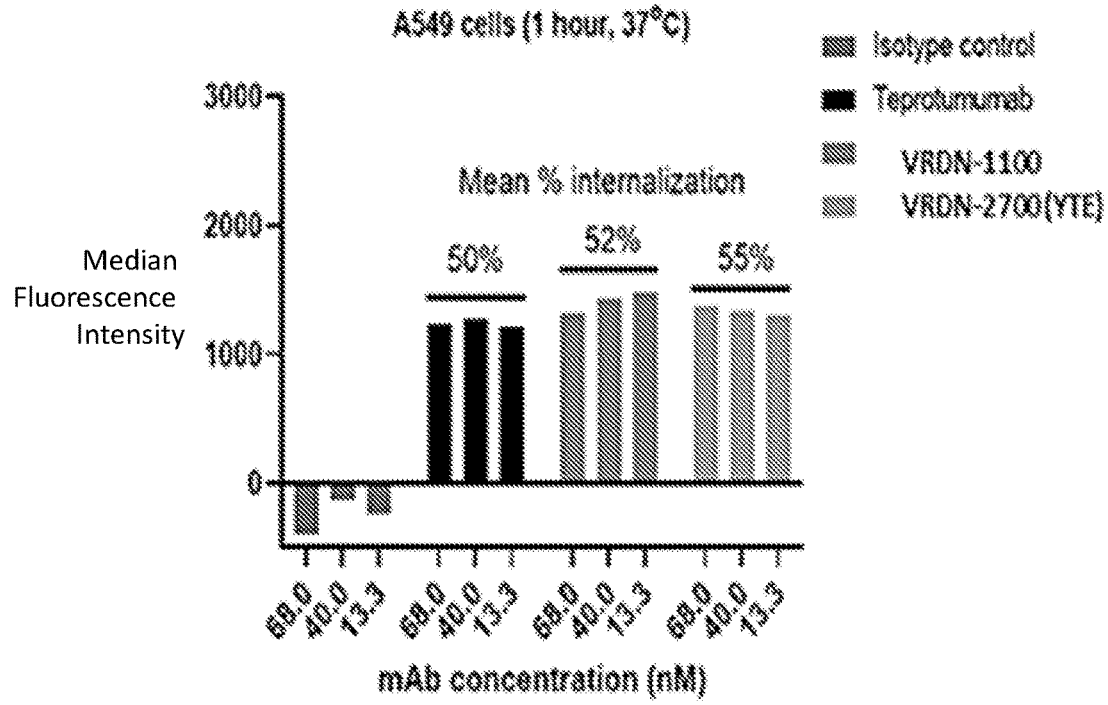
Figure 4A:
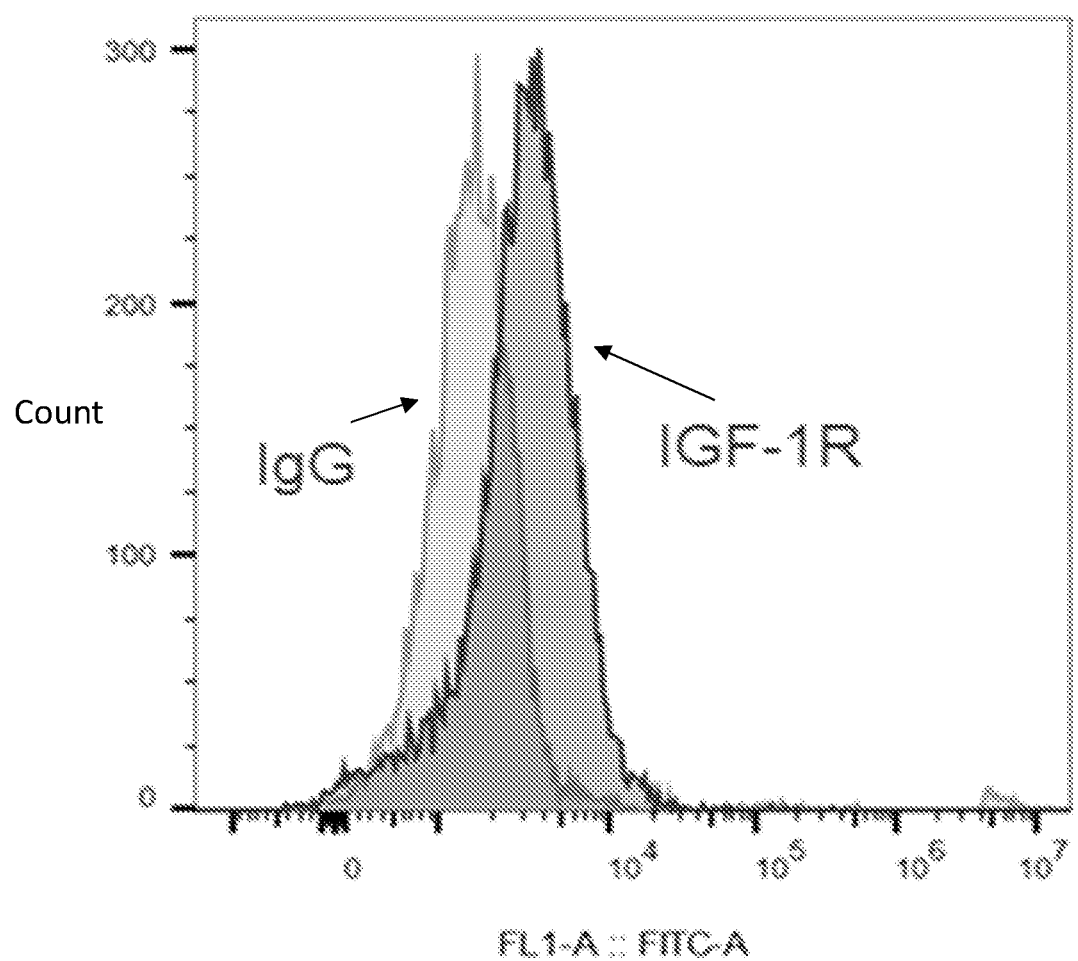
FIG. 4A-C illustrate that HOFCs were shown to express (Panel A) IGF-1R and (Panel B) TSHR, as well as (Panel C) CD34 and Thy-1.
Figure 4B:
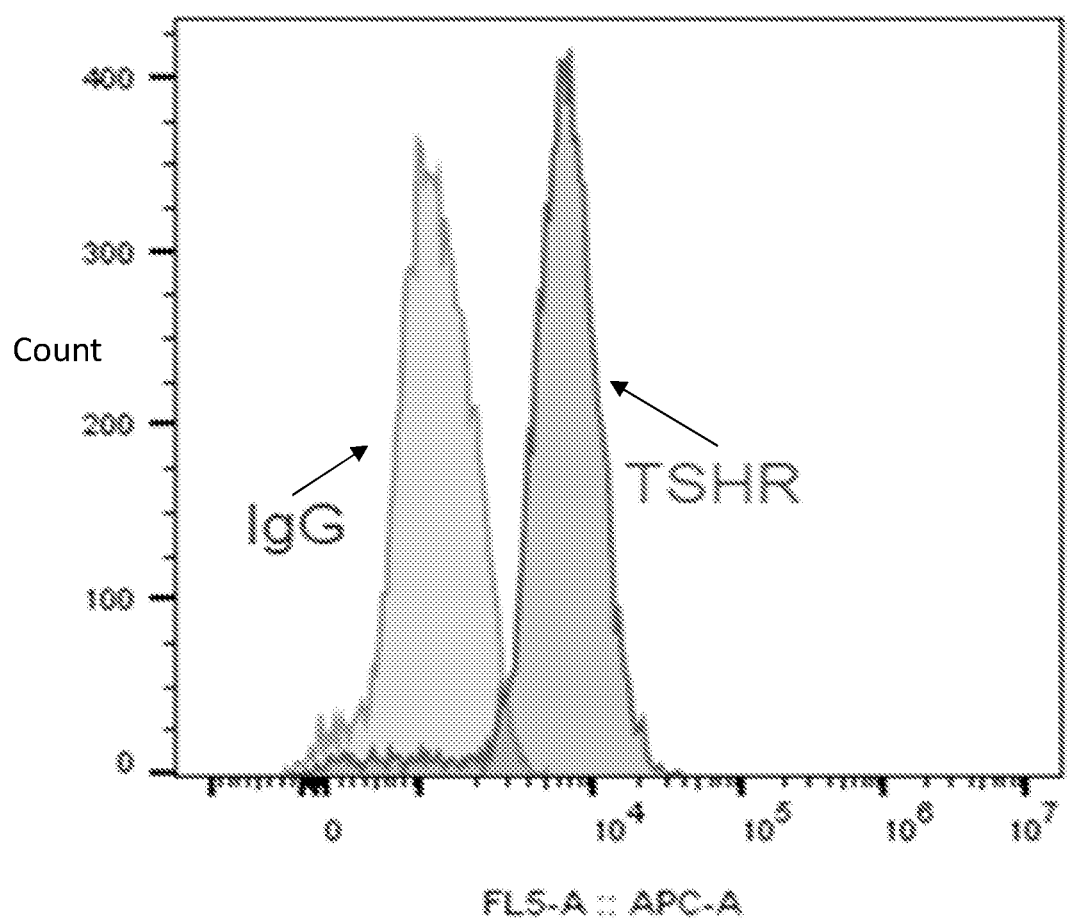
Figure 4C:
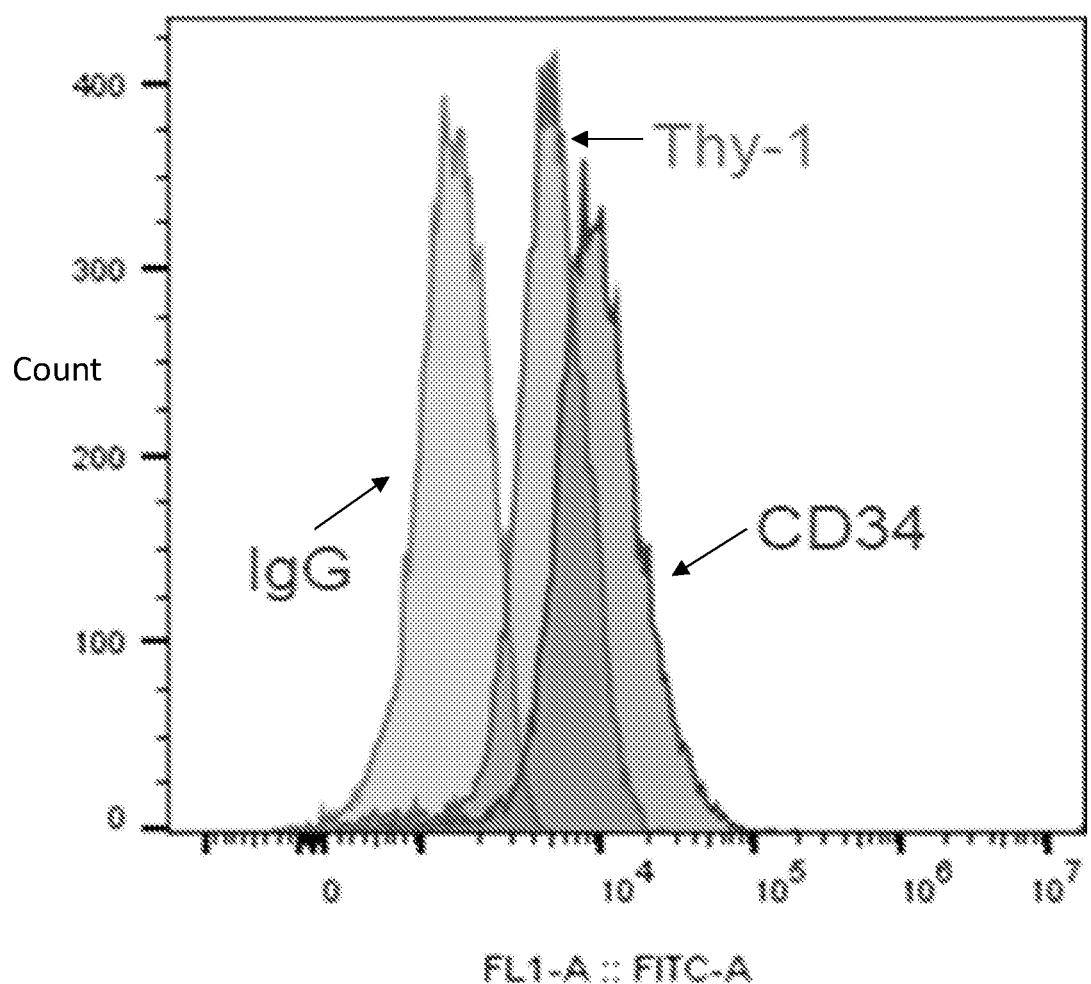

VRDN-1100 Binds IGF-1R with Sub-Nanomolar Affinity.
FIG. 2A illustrates that increasing concentrations of IGF-1R-ECD bound to anti-FC captured VRDN-1100 or teprotumumab reveal a stepwise increase in SPR signal, enabling a global fit to a binding model. Following IGF-1R washout, VRDN-1100 shows a more sustained binding interaction. FIG. 2B illustrates IGF-1R-ECD bound robustly to immobilized VRDN-1100. Teprotumumab showed no binding to the IGF-1R:VRDN-1100 complex, suggesting that teprotumumab and VRDN-1100 have overlapping epitopes. The data is also illustrated in the table as shown in FIG. 2B.
VRDN-1100 Binds with High Affinity to IGF-1R on A549 Cells.
As illustrated in FIG. 3A-C, VRDN-1100 binding to A549 cells was assessed by flow cytometry and found to have similar binding distribution as teprotumumab at three different concentrations. As also illustrated in FIG. 3D, in, the binding dose response curve demonstrated VRDN-1100 EC50=0.1 nM. As illustrated in FIG. 3E-F, VRDN-1100, VRDN-2700 with M252Y, S254T, and T256E mutation in the Fc domain, and teprotumumab show comparable binding at temperatures that block IGF-1R receptor internalization. FIG. 3F illustrates that VRDN-1100, VRDN-2700 with a M252Y, S254T, and T256E mutation in the Fc domain, and teprotumumab cause comparable levels of internalization (~50%) measured by reduction in membrane IGF-1R receptor levels at 37° C. vs 4° C. In FIG. 3E-F bar graphs the left most bars are the isotype control, the second to left set of bars are teprotumumab, the second from the right set of bars are VRDN-1100 and the right most set of bars are VRDN-2700.
HOCFs as an In Vitro Model for TED Pathology.
CD34+, Thy-1+ orbital fibroblasts are implicated in extracellular matrix deposition and pathogenic fibrosis in TED5. As illustrated in FIG. 4A-C, HOFCs were shown to express (Panel A) IGF-1R and (Panel B) TSHR, as well as (Panel C)

CD34 and Thy-1, which demonstrates their ability to be used as an in vitro model system for IGF-1R function in TED.

VRDN-1100 Binds with High Affinity to IGF-1R on HOCF Cells.

Figure 5A:
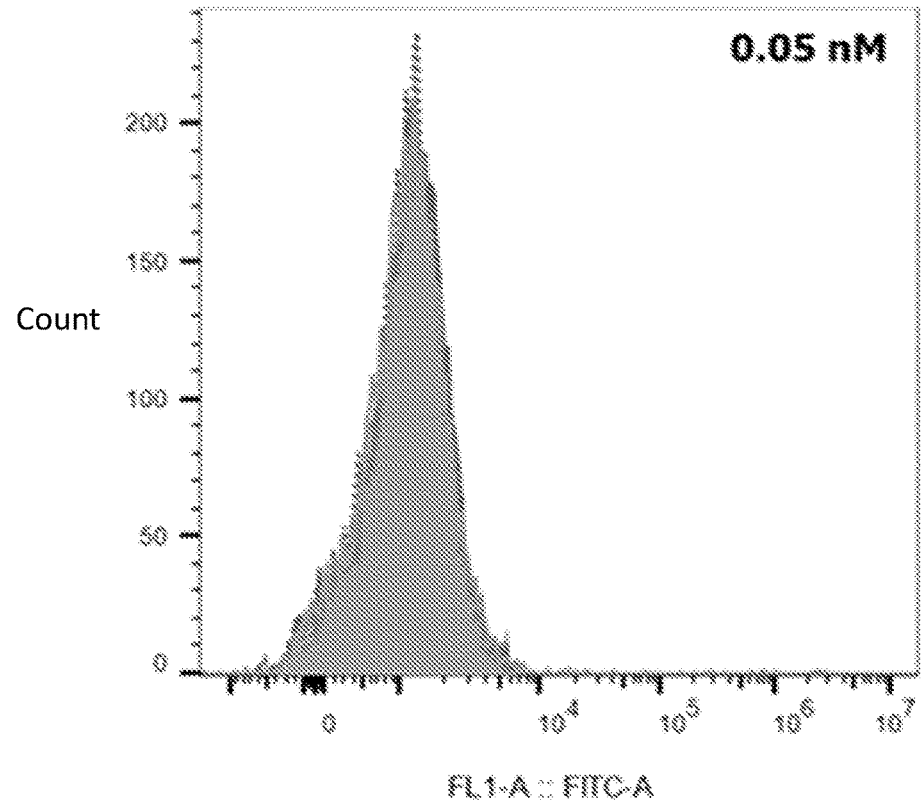
FIG. 5A and FIG. 5B illustrate VRDN-110 binding to HOCF cells, which was assessed by flow cytometry.
Figure 5A:
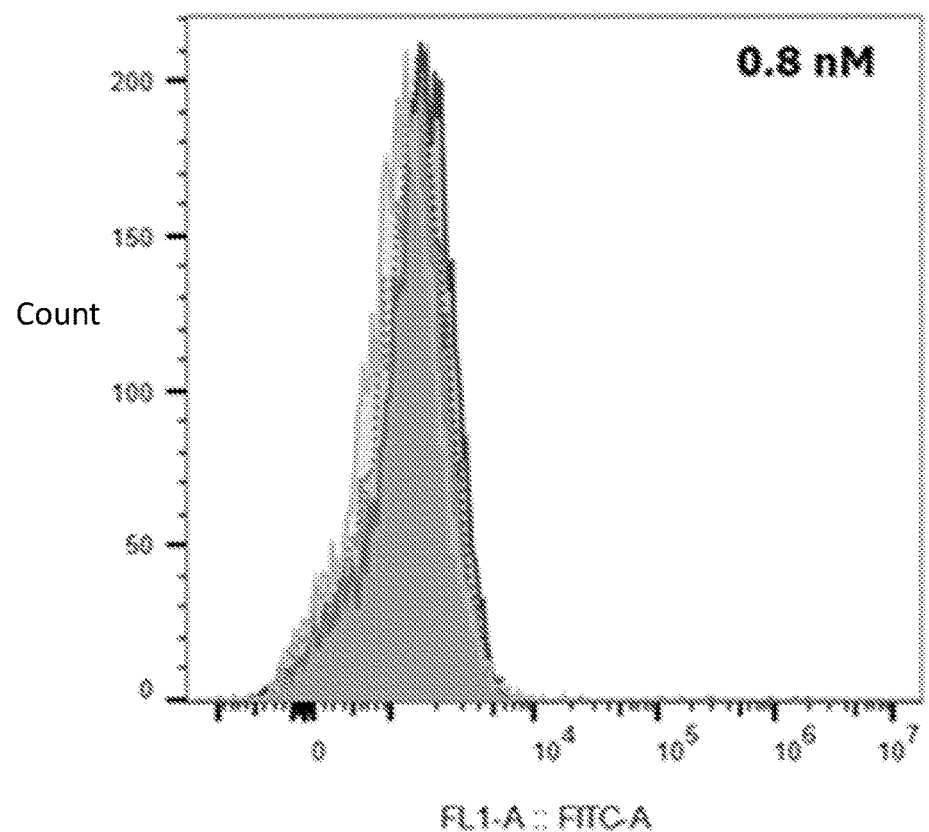
Figure 5B:
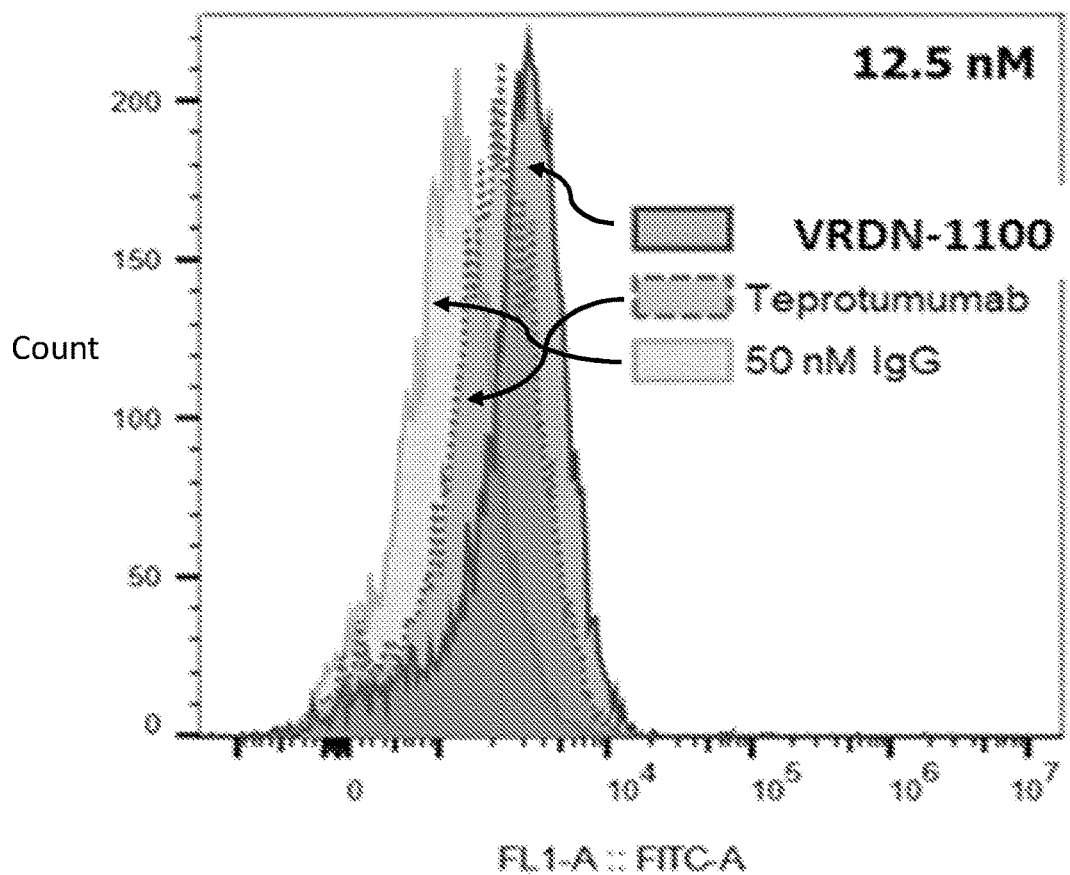
Figure 5B:
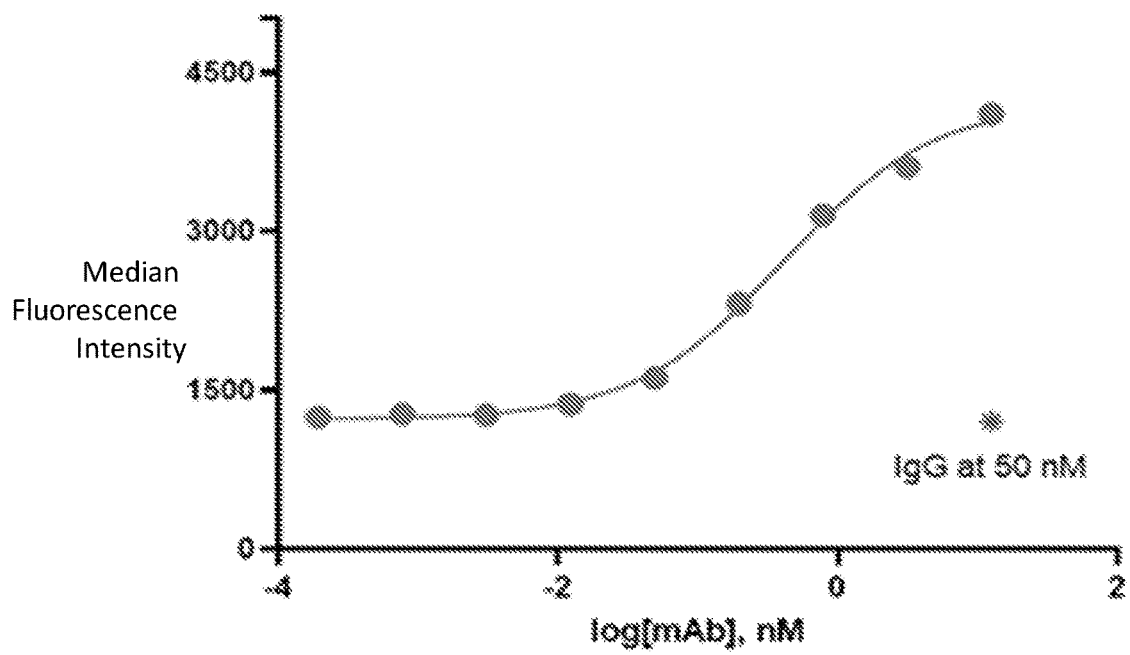

FIG. 5A and FIG. 5B illustrate VRDN-1100 binding to HOCF cells, which was assessed by flow cytometry and found to have largely similar binding as teprotumumab at three different concentrations. The lower panel of FIG. 5B illustrates a binding dose response curve, which demonstrated VRDN-1100 having an EC50=0.4 nM.

VRDN-1100 is a Sub-Nanomolar IGF-1R Antagonist.

Figure 6A:
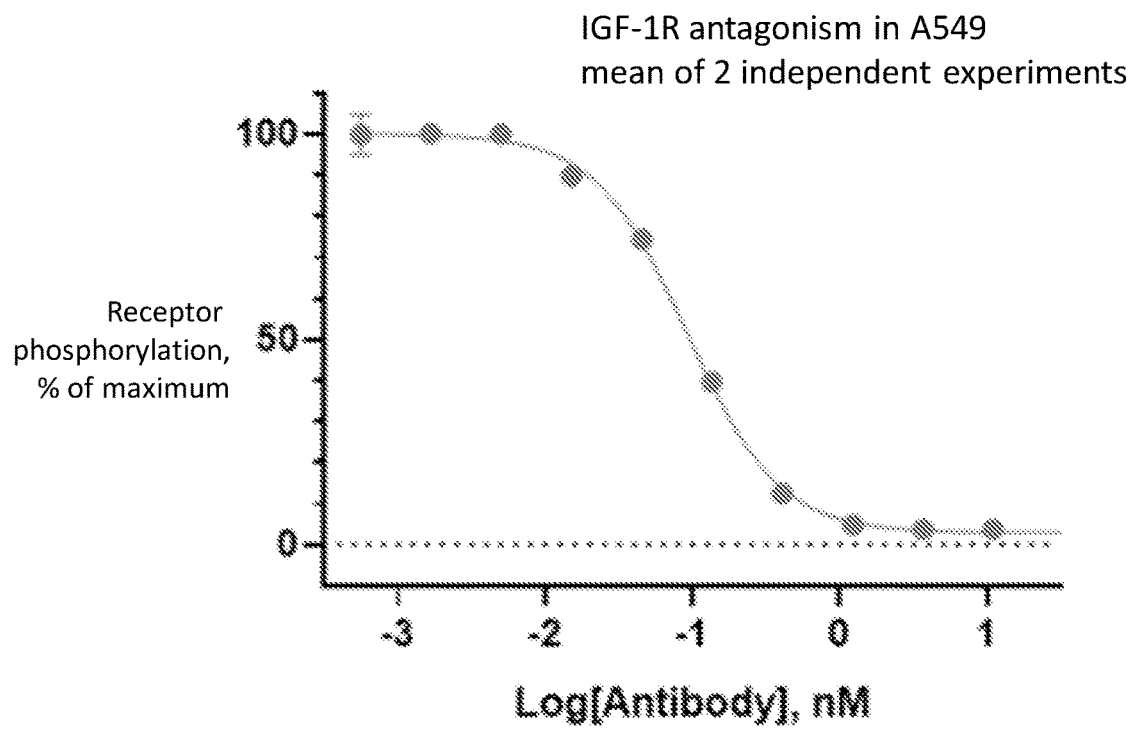
FIG. 6A and FIG. 6B illustrate that VRDN-1100 potently inhibits IGF-1R stimulated receptor phosphorylation on A549 cells (IC50=0.09 nM) and HOCF cells (IC50=0.09 nM).
Figure 6B:
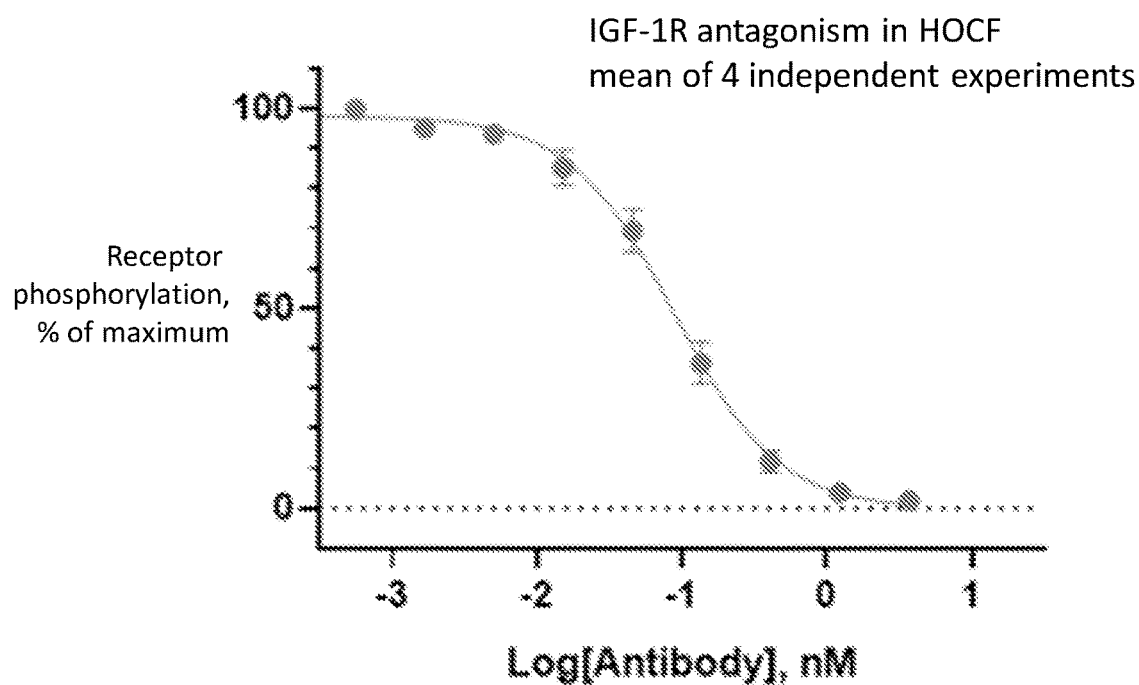

VRDN-1100 potently inhibits IGF-1 stimulated receptor phosphorylation on A549 cells (IC50=0.09 nM) and HOCF cells (IC50=0.09 nM), which is illustrated in FIG. 6A and FIG. 6B.

These results demonstrate that VRDN-1100 and teprotumumab epitopes on IGF-1R overlap, that VRDN-1100 binds to IGF-1R on cells with sub-nanomolar EC50, VRDN-1100 promotes IGF-1R internalization, and that VRDN-1100 inhibits IGF-1R phosphorylation with sub-nanomolar IC50. Accordingly, VRDN-1100 binds, antagonizes, and internalizes IGF-1R at sub-nanomolar concentrations, suggesting that VRDN-1100 should be a able to be used for the potential, potent inhibition of the pathophysiology driving TED.

Example 4

VRDN-2700, which has a M252Y, S254T, and T256E mutation in the Fc domain is a novel anti-IGF-1R antibody incorporating half-life extension modifications in its Fc region as described herein and can be used for the treatment of Thyroid Eye Disease (TED). The pharmacokinetic (PK) parameters of VRDN-2700 with such Fc mutations was measured in cynomolgus monkeys to the marketed IGF-1R antibody, teprotumumab, and a PK model was constructed to project potential human dosing regimens.

TED is an autoimmune condition most commonly associated with Graves' disease and hyperthyroidism but can also be found in patients who are euthyroid or hypothyroid. Orbitopathy in TED is driven by Thyroid Stimulating Hormone Receptor (TSHR) agonistic autoantibodies and crosstalk between TSHR and IGF-1R. Pathological remodeling of the orbit and periorbital tissues results in varied presentations which may include dry eyes, increased lacrimation, local irritation, eyelid retraction and eventually proptosis, diplopia, and optic nerve compression, with ensuing vision loss.

The underlying pathology of TED is the activation of an inflammatory cascade within the orbit, primarily due to recruitment of fibrocytes and immune cells. Over-expression of IGF-1R has been demonstrated within the orbit of TED patients, and it has been surmised that IGF-1R inhibitory antibodies may disrupt the IGF-1R and TSHR cross-talk and dampen the inflammatory cascade. Indeed, IGF-1R antagonism has been demonstrated to robustly relieve much of the inflammatory symptomology that affects TED patients.

VRDN-2700 is a monoclonal antibody that inhibits IGF-1 mediated signaling via IGF-1R with subnanomolar potency and incorporates clinically validated Fc modifications (M252Y, S254T, and T256E) to extend half-life. This antibody was found to have a more favorable PK profile with the potential for a less burdensome treatment paradigm for patients than conventional IgG therapeutic antibodies.

VRDN-2700 with the Fc mutations was administered to cynomolgus monkeys by 30 min intravenous (IV) infusions at 2, 10, and 50 mg/kg, and by subcutaneous (SC) injection at 2 and 10 mg/kg. Teprotumumab at 10 mg/kg was likewise administered by 30 min IV infusion. VRDN-2700 and teprotumumab levels in serum were measured using a human IgG specific ELISA assay. Data were analyzed using the WinNonlin™ non-compartmental model. A semi-mechanistic model incorporating target mediated drug disposition was constructed using available human and cynomolgus data. The data is illustrated below.

Figure 7:
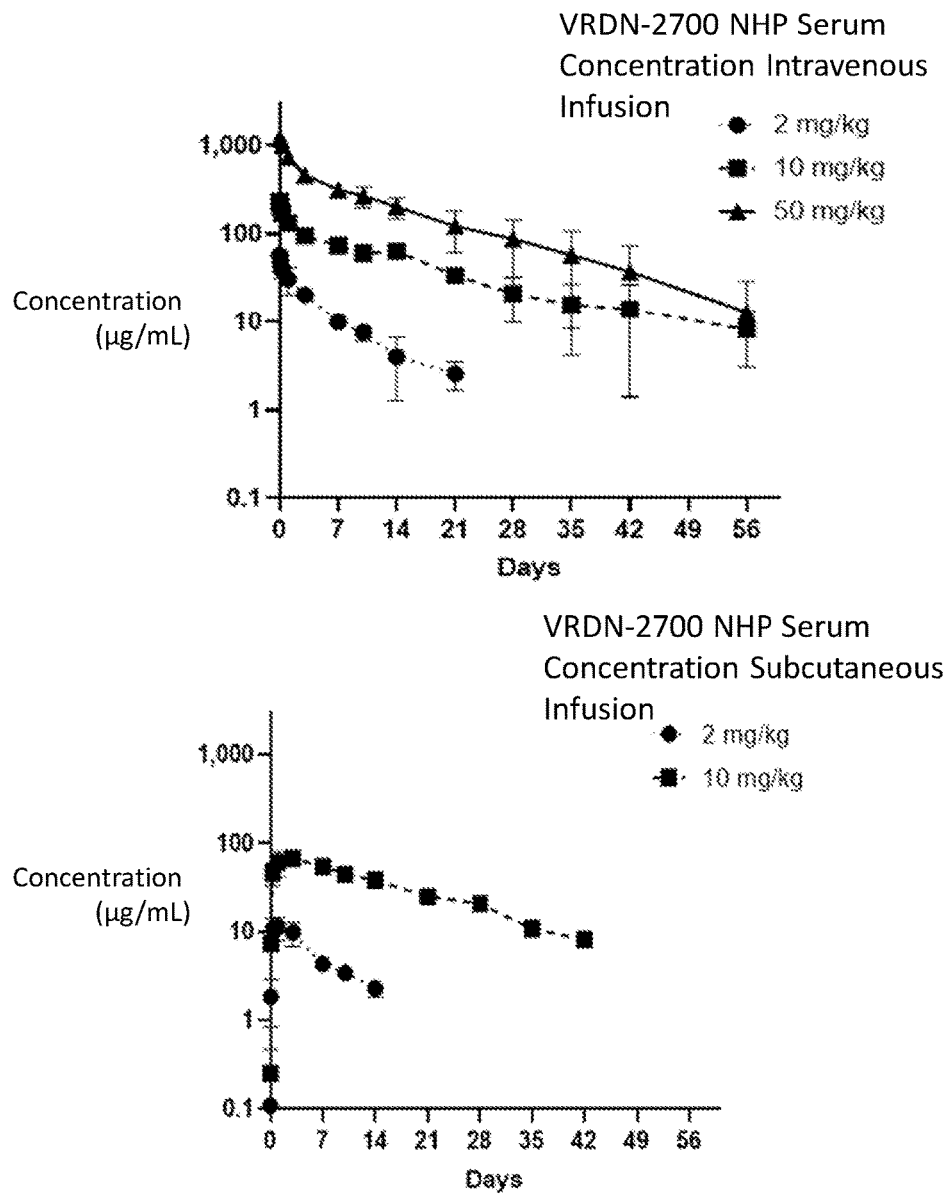
FIG. 7 illustrates non-human primate (NHP) serum concentrations and other properties of VRDN-2700 at various doses following either intravenous or subcutaneous administration.

The table and graphs illustrate of FIG. 7 the more favorable PK profile.

The table shows PK parameters+/−SD. Evidence of target mediated drug disposition (TMDD) was observed at 2 mg/kg, but not at 10 and 50 mg/kg doses, in line with teprotumumab and other IGF-1R antibodies that have reported saturation of TMDD at higher doses.

VRDN-2700 Half-Life Extension Modifications Prolong Exposure

Figure 8:
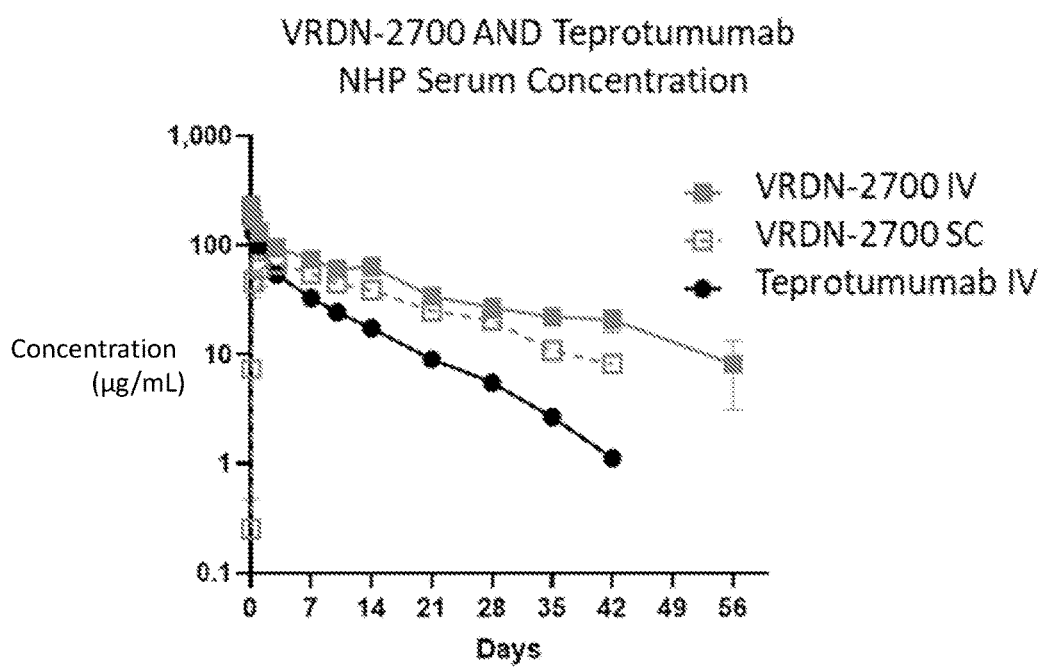
FIG. 8 illustrates various properties of VRDN-2700 with the YTE mutations after intravenous or subcutaneous administration to non-human primates as compared to teprotumumab administered intravenously to non-human primates.

At equivalent doses, SC dosed VRDN-2700 with the YTE mutations has greater exposure than intravenously infused teprotumumab and achieves ~2× half-life of teprotumumab in NHPs Estimated 62% bioavailability (F) of VRDN-2700 from SC dosing using preliminary discovery-stage formulation. Parameter estimates+/−SD shown in FIG. 8.

Model simulations predict that dosing of VRDN-2700 at 10 mg/kg every 3 weeks or 20 mg/kg every 6 weeks will result in Cmin of >100 ug/mL, similar to the approved teprotumumab regimen (10 mg/kg first dose followed by seven 20 mg/kg doses q3w). The 10 mg/kg q3w regimen will with lower Cmax values. A longer dosing interval would increase patient convenience and reduce treatment costs, while lower dose and Cmax values may potentially mitigate toxicities. Furthermore, the model predicts that weekly subcutaneous dosing of VRDN-2700 at 300 mg fixed dose could achieve a steady-state Cmin of ~130 ug/mL, enabling at home self-administration. In the event that lower Cmin values are efficacious, subcutaneous administration of VRDN-2700 at 300 mg fixed dose every other week is predicted to achieve ~50 ug/mL steady-state Cmin levels. Taken together, the extended half-life of VRDN-2700 is predicted to provide patients with a wider range of options for more convenient dosing interval and route of administration.

Example 5: VRDN2700 Properties

During the evaluation of the antibodies, expression of VRDN-2700 was compared to other antibodies having mutations in the Fc domain, such as the L/S mutations that are described herein. Unexpectedly, the yield for the antibody with the YTE mutation in the Fc domain (VRDN2700) was approximately 80% higher than the yield of a similar antibody except that it has a L/S mutation. This was surprising and unexpected as other antibodies that have been tested that target IGF-1R with the YTE or LS mutations had similar expressions regardless of the Fc mutations. The YTE version had fewer lower molecular weight species as compared to the LS version. Thus, indicating that the YTE antibody has fewer impurities and is a more homogenous composition, which provides advantages over the antibody with the LS mutation. This was also not predictable as another antibody that was evaluated showed the opposite effect on such species. Furthermore, during purification, it was found that the LS mutant formed more aggregates when being purified on a cation exchange column as compared VRDN-2700. The aggregation of the LS mutant would cause significant manufacturing issues, which were not observed for VRDN-2700. Therefore, this difference in the Fc mutants for this antibody could not have been predicted or expected and leads to significant and unexpected advantages for the antibody that is referenced herein as VRDN-2700.

The prolonged half-life of VRDN-2700 (YTE) demonstrates that it can be used in a convenient SC injection, or as an IV infusion requiring fewer and/or less frequent treatments vs. conventional therapeutic IgG antibodies and has superior properties as compared to other Fc mutant versions of the same antibody (same variable regions).

Example 6: VRDN-1100 with YTE or YTE/C22S Mutations Bind to IGF-1R and Inhibits IGF-1R Autophosphorylation The binding of VRDN-1100 with the Fc YTE mutations in the heavy chain (SEQ ID NO: 94) or C22S mutation and Fc YTE mutations in the heavy chain (SEQ ID NO: 95) to IGF-1R was evaluated in a cell based binding assay (A549 cells). The light chains have a sequence of SEQ ID NO: 93. The YTE Fc mutant version of VRDN1100 was found to bind to A549 cells with an EC50 of 0.30 nm and the C22S and Fc YTE mutant had an EC50 of 0.36 nm. The antibodies were also evaluated for their ability to inhibit IGF-1R autophosphorylation. The YTE only mutant had an IC50 of 0.40 nm and the C22S plus YTE mutations had an IC50 of 0.37 nm. Thus, the antibodies were found to be able to both bind to IGF-1R and inhibit its autophosphorylation.

Example 7: VRDN-1100 with a C22S Mutation Binds to IGF-1R

A mutant of VRDN-1100 with a C22S mutation in the heavy chain (SEQ ID NO: 96) and a VL comprising a sequence of SEQ ID NO: 97 was evaluated for its binding to IGF-1R in a surface plasma resonance assay. Using this assay, the antibody was found to bind to IGF-1R with a $k_a$ (1/Ms) of $1.04 \times 10^5$, a kd (1/s) of $2.18 \times 10^{-5}$, and a $K_D(M)$ of $2.10 \times 10^{-10}$ at a pH of 7.4.

Each of these examples and the embodiments provided herein demonstrate that the antibodies provided for herein can be used to treat TED and their associate symptoms.

All references cited herein are incorporated by reference to the same extent as if each individual publication, database entry (e.g. Genbank® sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank® sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present embodiments are not to be limited in scope by the specific embodiments described herein. Indeed, various modifications in addition to those described herein will become apparent to those skilled in the art from the foregoing description. Such modifications are intended to fall within the scope of the embodiments and any appended claims.

The present specification is considered to be sufficient to enable one skilled in the art to practice the embodiments. Various modifications in addition to those shown and described herein will become apparent to those skilled in the art from the foregoing description and fall within the scope of the present disclosure and any appended claims.

What is claimed is:

1. An antibody comprising a light chain and a heavy chain, wherein:
   the light chain comprises a light chain variable region comprising a LCDR1 of SEQ ID NO: 53, a LCDR2 of SEQ ID NO: 54, and a LCDR3 of SEQ ID NO: 55; and
   the heavy chain comprises a heavy chain variable region comprising a HCDR1 of SEQ ID NO: 56, a HCDR2 of SEQ ID NO: 57, and a HCDR3 of SEQ ID NO: 58, and an Fc region comprising an amino acid sequence of SEQ ID NO: 89.

2. A pharmaceutical composition comprising the antibody of claim 1.

3. The antibody of claim 1, wherein the antibody has an IC50 of less than or equal to 0.4 nM.

4. An antibody comprising a light chain and a heavy chain, wherein the light chain comprises an amino acid sequence of SEQ ID NO: 93 and the heavy chain comprises an amino acid sequence of SEQ ID NO: 94.

5. A pharmaceutical composition comprising the antibody of claim 4.

6. The antibody of claim 4, wherein the antibody has an IC50 of less than or equal to 0.4 nM.

7. An antibody comprising a light chain and a heavy chain, wherein
   the light chain comprises a light chain variable region comprising an amino acid sequence of SEQ ID NO: 13, and
   the heavy chain comprises a heavy chain variable region comprising an amino acid sequence of SEQ ID NO: 14, and an Fc region comprising an amino acid sequence of SEQ ID NO: 89.

8. A pharmaceutical composition comprising the antibody of claim 7.

9. The antibody of claim 7, wherein the antibody has an IC50 of less than or equal to 0.4 nM.

* * * * *